(12) United States Patent
Bielawska et al.

(10) Patent No.: US 8,592,419 B2
(45) Date of Patent: Nov. 26, 2013

(54) CERAMIDES AND APOPTOSIS-SIGNALING LIGAND

(75) Inventors: Alicja Bielawska, Charleston, SC (US); Yusuf A. Hannun, Sullivan's Island, SC (US); James Norris, Mount Pleasant, SC (US); Zdzislaw M. Szulc, Charleston, SC (US); Jian-yun Dong, Mount Pleasant, SC (US); Jacek Bielawski, Charleston, SC (US); David A. Schwartz, Summerville, SC (US); David H. Holman, Charleston, SC (US); Ahmed M. El-Zawahry, Charleston, SC (US); John McKillop, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 845 days.

(21) Appl. No.: 11/666,519

(22) PCT Filed: Oct. 31, 2005

(86) PCT No.: PCT/US2005/039272
§ 371 (c)(1),
(2), (4) Date: Aug. 16, 2007

(87) PCT Pub. No.: WO2006/050265
PCT Pub. Date: May 11, 2006

(65) Prior Publication Data
US 2008/0045470 A1 Feb. 21, 2008

Related U.S. Application Data

(60) Provisional application No. 60/623,293, filed on Oct. 29, 2004.

(51) Int. Cl.
*A61K 31/40* (2006.01)
*A61K 31/44* (2006.01)
*A61K 31/415* (2006.01)
*A61K 31/445* (2006.01)
*A61K 31/497* (2006.01)
*A61K 31/535* (2006.01)
*C07D 211/00* (2006.01)
*C07D 213/06* (2006.01)
*C07D 207/00* (2006.01)
*C07D 233/00* (2006.01)
*C07D 295/00* (2006.01)

(52) U.S. Cl.
USPC ............... 514/237.8; 514/252.12; 514/315; 514/357; 514/399; 514/408; 544/162; 544/402; 546/246; 546/251; 548/335.1; 548/400

(58) Field of Classification Search
USPC ......... 514/357, 252.12, 237.8, 315, 399, 408; 546/93, 246, 251; 544/162, 402; 548/335.1, 400
See application file for complete search history.

(56) References Cited

U.S. PATENT DOCUMENTS

| | | | |
|---|---|---|---|
| 2,515,465 A | 7/1950 | Mozingo et al. | |
| 3,044,936 A | 7/1962 | Daniel et al. | |
| 3,466,292 A | 9/1969 | Paquette et al. | |
| 4,016,287 A | 4/1977 | Eberhardt et al. | |
| 4,151,198 A | 4/1979 | Halmos | |
| 4,474,977 A * | 10/1984 | Lambelin et al. | 560/1 |
| 4,544,670 A | 10/1985 | Studt et al. | |
| 4,622,325 A | 11/1986 | Fujii et al. | |
| 4,859,761 A | 8/1989 | Flury et al. | |
| 4,897,355 A | 1/1990 | Eppstein et al. | |
| 4,937,232 A | 6/1990 | Bell et al. | |
| 5,369,030 A | 11/1994 | Hannun et al. | |
| 5,559,154 A | 9/1996 | Weber et al. | |
| 5,679,350 A | 10/1997 | Jankun et al. | |
| 5,830,916 A | 11/1998 | Hannun et al. | |
| 5,851,782 A | 12/1998 | Hannun et al. | |
| 5,916,911 A | 6/1999 | Shayman et al. | |
| 6,284,798 B1 | 9/2001 | Amtmann et al. | |
| 6,610,835 B1 | 8/2003 | Liotta et al. | |
| 6,696,081 B2 | 2/2004 | Grinstaff et al. | |
| 6,756,504 B2 * | 6/2004 | Dagan et al. | 554/52 |
| 7,172,879 B2 | 2/2007 | Gamble et al. | |
| 8,093,393 B2 | 1/2012 | Bielawska et al. | |
| 2003/0133904 A1 | 7/2003 | Dagan et al. | |
| 2005/0209260 A1 | 9/2005 | Broka et al. | |
| 2008/0146640 A1 | 6/2008 | Glinka | |

| | | | |
|---|---|---|---|
| 2008/0167352 | A1 | 7/2008 | Smith et al. |
| 2008/0268073 | A1 | 10/2008 | Sano et al. |
| 2011/0071099 | A1 | 3/2011 | Bielawska et al. |
| 2011/0251197 | A1 | 10/2011 | Bielawska et al. |
| 2012/0035268 | A1 | 2/2012 | Szulc et al. |

FOREIGN PATENT DOCUMENTS

| | | |
|---|---|---|
| GB | 630 712 | 10/1949 |
| GB | 1 487 283 | 9/1977 |
| WO | WO00/27883 | 5/2000 |
| WO | WO01/79152 | 10/2001 |
| WO | WO02/22175 | 3/2002 |
| WO | WO03/005965 | 1/2003 |
| WO | WO2004/074247 | 9/2004 |
| WO | WO2006/050264 | 5/2006 |
| WO | WO2006/050265 | 5/2006 |
| WO | WO2006/138660 | 12/2006 |
| WO | WO2010/054223 | 5/2010 |
| WO | WO2010/078247 | 7/2010 |

OTHER PUBLICATIONS

Speer et al, Some Nucleus alkyl derivatives of phenethylamine, 1937, J. of Organic chemistry , 2, p. 139-147(abstract page).*  Feng et al, Some Derivatives of ephedrine , 1930, 4, p. 231-246(abstract page).*

Chen et al, Relationship between the pharmacological action and the chemical constitution and configuration of the optical isomers of epherine andrelated compounds, J. Pharmacol. , 1929, 36, p. 363-400 (abstract page).*

Emerson, Syntheses with Styrene Oxide, Journal of the American chemical society , 1945, 67, p. 516-518.*

Oggenfuss et al , Transport of Ions through Neutral Carrier Membranes, 1981, Analytical Chemistry Symposium Seires, 8,(Ion-Sel,. Electrodes, 3 ), p. 73-86, abstract page (1 page).*

Notification concerning Transmittal of International Preliminary Report on Patentability (Chapter 1 of the Patent Cooperation Treaty) corresponding to PCT Application No. PCT/US05/39272 dated May 10, 2007.

Lutz et al. Antimalarials. α-phenyl-β-dialkylamino alcohols. *Journal of Organic Chemistry*, vol. 12, (1947), pp. 617-703.

Notification of Transmittal of the International Search Report and The Written Opinion of the International Searching Authority, or the Declaration corresponding to the PCT Application No. PCT/US05/39272 dated Jan. 30, 2007.

Lutz et al. Antimalarials. α-phenyl-β-dialkylamino alcohols. *Journal of Organic Chemistry*, (1947), pp. 617-703.

Agrawal et al., "Cell-cycle kinetics and VSV-G pseudotyped retrovirus-mediated gene transfer in blood-derived CD34+ cells," Experimental Hematology. vol. 24 pp. 738-747 (1996).

Ardail et al., "Subcellular distribution and metabolic fate of exogenous ceramides taken up by HL-60 cells," Biochimica et Biophysica Acta. vol. 1583 pp. 305-310 (2002).

Ashkenazi, A., and Dixit, V.M., "Apoptosis control by death and decoy receptors," Current Opinion in Cell Biology. vol. 11 pp. 255-260 (1999).

Ashkenazi, A., and Dixit, V.M., "Death Receptors: Signaling and Modulation," Science. vol. 281 pp. 1305-1308 (1998).

Bai et al., poster (SERLC, Sep. 11, 2008) titled "Synthesis and Bioevaluation of ω-Amino Analogs of B13 as Potential Anticancer Agents Targeting Acid Ceramidase."

Bai et al. "Synthesis and bioevaluation of ω-N-amino analogs of B13," Bioorganic & Medicinal Chemistry. vol. 17 pp. 1840-1848 (2009).

Bernatowicz et al., "Urethane Protected Derivatives of 1-Guanylpyrazole for the Mild and Efficient Preparation of Guanidines," Tetradhedron Letters. vol. 34, No. 21 pp. 3389-3392 (1993).

Bieberich et al., "N-Acylated Serinol Is a Novel Ceramide Mimic Inducing Apoptosis in Neuroblastoma Cells," The Journal of Biological Chemistry. vol. 275, No. 1 pp. 177-181 (2000).

Bieberich et al., "Synthesis and characterization of novel ceramide analogs for induction of apoptosis in human cancer cells," Cancer Letters. vol. 181 pp. 55-64 (2002).

Bielawska et al., "(1S,2R)-D-erythro-2-(N-Myristoylamino)-1-phenyl-1-propanol as an Inhibitor of Ceramidase," The Journal of Biological Chemistry. vol. 271, No. 21 pp. 12646-12654 (1996).

Bielawska et al., "Ceramide-mediated Biology," The Journal of Biological Chemistry. vol. 267, No. 26 pp. 18493-18497 (1992).

Bielawska et al., "Novel analogs of D-e-MAPP and B13. Part 2: Signature effects on bioactive sphingolipids," Bioorganic & Medicinal Chemistry. vol. 16 pp. 1032-1045 (2008).

Bielawska et al., "Selectivity of Ceramide-mediated Biology," The Journal of Biological Chemistry. vol. 268, No. 35 pp. 26226-26232 (1993).

Bielawska et al., "Synthesis of Key Precursors of Radiolabeled Sphingolipids," Methods in Enzymology. vol. 311 pp. 518-535 (1999).

Bielawski et al., "Simultaneous quantitative analysis of bioactive sphingolipids by high-performance liquid chromatography-tandem mass spectrometry," Methods. vol. 39 pp. 82-91 (2006).

Birbes et al., "Selective hydrolysis of a mitochondrial pool of sphingomyelin induces apoptosis," FASEB Journal. vol. 14 pp. 2669-2679 (2001).

Black, W.C., and Percival, M.D., "The Consequences of Lysosomotropism on the Design of Selective Cathepsin K Inhibitors," ChemBioChem. vol. 7 pp. 1525-1535 (2006).

Bose et al., "Ceramide Synthase Mediates Daunorubicin-lnduced Apoptosis: An Alternative Mechanism for Generating Death Signals," Cell. vol. 82 pp. 405-414 (1995).

Boya et al., "Mitochondrial membrane permeabilization is a critical step of lysosome-initiated apoptosis induced by hydroxychloroquine," Oncogene. vol. 22 pp. 3927-3936 (2003).

Brown et al., "Mechanism of action of a dominant-negative mutant of c-Jun," Oncogene. vol. 9 pp. 791-799 (1994).

Buchwald et al., "Long-term, continuous intravenous heparin administration by an implantable infusion pump in ambulatory patients with recurrent venous thrombosis," Surgery. vol. 88, No. 4 pp. 507-516 (1980).

Buttle et al., "CA074 Methyl Ester: A Proinhibitor for Intracellular Cathepsin B, Archives of Biochemistry and Biophysics," Archives of Biochemistry & Biophysics. vol. 299, No. 2 pp. 377-380 (1992).

Chad et al., "Site-Directed Mutagenesis of UDP-Galactopyranose Mutase Reveals a Critical Role for the Active-Site, Conserved Arginine Residues," Biochemistry. vol. 46 pp. 6723-6732 (2007).

Chalfant et al., "FAS Activation Induced Dephosphorylation of SR Proteins," The Journal of Biological Chemistry. vol. 276, No. 48 pp. 44848-44855 (2001).

Chalfant et al., "The structural requirements for ceramide activation of serine-threonine protein phosphatases," J. Lipid Res. vol. 45 pp. 496-506 (2004).

Charles et al., "Ceramide-Coated Balloon Catheters Limit Neointimal Hyperplasia After Stretch Injury in Carotid Arteries," Circ Res. vol. 87 pp. 282-288 (2000).

Cherioux, F., and Audebert, P., "New Star-Shaped Molecules with Extended Electronic Delocalization," Chem. Mater. vol. 10 pp. 1984-1989 (1998).

Cremesti et al., "Ceramide Enables Fas to Cap and Kill," The Journal of Biological Chemistry. vol. 276, No. 26 pp. 23954-23961 (2001).

Dagan et al., "Synthetic, non-natural sphingolipid analogs inhibit the biosynthesis of cellular sphingolipids, elevate ceramide and induce apoptotic cell death," Biochimica et Biophysica Acta. vol. 1633 pp. 161-169 (2003).

Database Beilstein Beilstein Institute for Organic Chemistry, Frankfurt-Main, DE; 1932, Database Accession No. BRN: 3854595 & Slotta, Justus Liebigs Annalen der Chemie. vol. 497 pp. 171-178 (1932).

Database Beilstein Beilstein Institute for Organic Chemistry, Frankfurt-Main, DE; 1933, Database Accession No. BRN: 3684371 & Abderhalden, Schweitzer: Fermentforschung. vol. 13 pp. 128-133 (1933) [Abstract].

Database Beilstein Beilstein Institute for Organic Chemistry, Frankfurt-Main, DE; 1949, Database Accession No. BRN: 3814715 & Cornforth, Chem. Penicillin. pp. 688 and 798 (1949) [Abstract].

Database Beilstein Beilstein Institute for Organic Chemistry, Frankfurt-Main, DE; 1958, Database Accession No. BRN: 3805955 & Kratzl, Berger: Monatshefte fuer Chemie. vol. 89 pp. 160-164 (1958) [Abstract].
Database Beilstein Beilstein Institute for Organic Chemistry, Frankfurt-Main, DE; 1966, Database Accession No. BRN: 4138625 & Ciusa, Barbiroli: Annali di Chimica. vol. 56 pp. 3-6 (1966) [Abstract].
Database Beilstein Beilstein Institute for Organic Chemistry, Frankfurt-Main, DE; 1982, Database Accession No. BRN: 4628299 & Katritzky et al., Journal of Heterocyclic Chemistry. vol. 19 pp. 741-745 (1982) [Abstract].
Davis et al., "Mitochondrial and Plasma Membrane Potentials Cause Unusual Accumulation and Retention of Rhodamine 123 by Human Breast Adenocarcinoma-derived MCF-7 Cells," The Journal of Biological Chemistry. vol. 260, No. 25 pp. 13844-13850 (1985).
Di Paola et al., "Ceramide Interaction with the Respiratory Chain of Heart Mitochondria," Biochemistry. vol. 39 pp. 6660-6668 (2000).
El Bawab et al., "Biochemical Characterization of the Reverse Activity of Rat Brain Ceramidase," The Journal of Biological Chemistry. vol. 276, No. 20 pp. 16758-16766 (2001).
El Bawab et al., "Purification and Characterization of a Membrane-bound Nonlysosomal Ceramidase from Rat Brain," The Journal of Biological Chemistry. vol. 274, No. 39 pp. 27946-27955 (1999).
El Bawab et al., "Substrate specificity of rat brain ceramidase," J. Lipid Res. vol. 43 pp. 141-148 (2002).
Elojeimy et al., "Role of Acid Ceramidase in Resistance to FasL: Therapeutic Approaches Based on Acid Ceramidase Inhibitors and FasL Gene Therapy," Molecular Therapy. vol. 15, No. 7 pp. 1259-1263 (2007).
English et al., "Sphingosine 1-phosphate released from platelets during clotting accounts for the potent endothelial cell chemotactic activity of blood serum and provides a novel link between hemostasis and angiogenesis," FASEB Journal. vol. 14 pp. 2255-2265 (2000).
Extended European Search Report corresponding to European Patent Application No. 05820909.9-2101 dated Jul. 3, 2009.
Fantin et al., "A novel mitochondriotoxic small molecule that selectively inhibits tumor cell growth," Cancer Cell. vol. 2 pp. 29-42 (2002).
Felgner et al., "Lipofection: A highly efficient, lipid-mediated DNA-transfection procedure," PNAS. vol. 84 pp. 7413-7417 (1987).
French et al., "Antitumor Activity of Sphingosine Kinase Inhibitors," The Journal of Pharmacology and Experimental Therapeutics. vol. 318, No. 2 pp. 596-603 (2006).
French et al., "Discovery and Evaluation of Inhibitors of Human Sphingosine Kinase," Cancer Research. vol. 63 pp. 5962-5969 (2003).
García-Ruiz et al., "Direct Effect of Ceramide on the Mitochondrial Electron Transport Chain Leads to Generation of Reactive Oxygen Species," The Journal of Biological Chemistry. vol. 272, No. 17 pp. 11369-11377 (1997).
Garner et al., "A Stereodivergent Synthesis of D-*erthyro*-Sphingosine and D-*threo*-. Sphingosine from L-Serine," J. Org. Chem. vol. 53, No. 18 pp. 4395-4398 (1988).
Ghafourifar et al., "Ceramide Induces Cytochrome *c* Release from Isolated Mitochondria," The Journal of Biological Chemistry. vol. 274, No. 10 pp. 6080-6084 (1999).
Ghosh et al., "Probing the function(s) of active-site arginine residue in *Leishmania donovani* adenosine kinase," Biochem. J. vol. 298 pp. 295-301 (1994).
Goodman et al., "Recombinant Adeno-Associated Virus-Mediated Gene Transfer Into Hematopoietic Progenitor Cells," Blood. vol. 84, No. 5 pp. 1492-1500 (1994).
Grether-Beck et al., "Mitochondrial Cytochrome c Release Mediates Ceramide-induced Activator Protein 2 Activation and Gene Expression," The Journal of Biological Chemistry. vol. 278, No. 48 pp. 47498-47507 (2003).
Gu et al., "Induction of p53-regulated genes in lung cancer cells: implications of the mechanism for adenoviral p53-mediated apoptosis," Oncogene. vol. 23 pp. 1300-1307 (2004).
Hakogi et al., "Synthesis of Fluorescence-Labeled Sphingosine and Sphingosine 1-Phosphate; Effective Tools for Sphingosin and Sphingosine 1-Phosphate Behavior," Bioorganic & Medicinal Chemistry Letters. vol. 13 pp. 661-664 (2003).
Hann, B., and Balmain, A., "Building 'validated' mouse models of human cancer," Current Opinion in Cell Biology. vol. 13 pp. 778-784 (2001).
Hannun, Y.A., and Luberto, C., "Ceramide in the eukaryotic stress response," Trends in Cell Biology. vol. 10 pp. 73-80 (2000).
Hannun, "Functions of ceramide in coordinating cellular responses to stress," Science. vol. 274, No. 5294 pp. 1855-1859 (1996).
Hansen et al., "Re-examination and further development of a precise and rapid dye method for measuring cell growth/cell kill," Journal of Immunological Methods. vol. 119 pp. 203-210 (1989).
Hayter et al., "TNFα-induced glutathione depletion lies downstream of cPLA$_2$ in L929 cells," FEBS Letters. vol. 507 pp. 151-156 (2000).
He et al., "Purification and Characterization of Recombinant, Human Acid Ceramidase," The Journal of Biological Chemistry. vol. 278, No. 35 pp. 32978-32986 (2003).
Hla, "Signaling and biological actions of sphingosine 1-phosphate," Pharmacological Research. vol. 47 pp. 401-407 (2003).
Holman et al., "Lysosomotropic acid ceramidase inhibitor induces apoptosis in prostate cancer cells," Cancer Chemother. Pharmacol. vol. 61 pp. 231-242 (2008).
Howard et al., "Intracerebral drug delivery in rats with lesion induced memory deficits," J. Neurosurg. vol. 71 pp. 105-112 (1989).
Huwiler, A., and Zangemeister-Wittke, U., "Targeting the conversion of ceramide to sphingosine 1-phosphate as a novel strategy for cancer therapy," Oncology Hematol. vol. 63 pp. 150-159 (2007).
Hyer et al., "Downregulation of c-FLIP Sensitizes DU145 Prostate Cancer Cells to Fas-Mediated Apoptosis," Cancer Biology & Therapy. vol. 1, No. 4 pp. 401-406 (2002).
Hyer et al., "Quantification and characterization of the bystander effect in prostate cancer cells following adenovirus-mediated FasL expression," Cancer Gene Therapy. vol. 10 pp. 330-339 (2003).
Inaba et al., "Evaluation of Antitumor Activity in a Human Breast Tumor/Nude Mouse Model With a Special Emphasis on Treatment Dose," Cancer. vol. 64 pp. 1577-1582 (1989).
Johnson et al., "Role of Human Sphingosine-1-phosphate Phosphatase 1 in the Regulation of Intra- and Extracellular Sphingosine-1-phosphate Levels and Cell Viability," The Journal of Biological Chemistry. vol. 278, No. 36 pp. 34541-34547 (2003).
Jones et al., "Ceramide Induces Caspase-Independent Apoptosis in Rat Hepatocytes Sensitized by Inhibition of RNA Synthesis," Hepatology. vol. 30 pp. 215-222 (1999).
Jones-Bolin et al., "The effects of the oral, pan-VEGF-R kinase inhibitor CEP-7055 and chemotherapy in orthotopic models of glioblastoma and colon carcinoma in mice," Molecular Cancer Therapeutics. vol. 4, No. 7 pp. 1744-1753 (2006).
Jursic, "An Enantiomeric Discrimination in Aqueous Mixed Chiral Micelles Through Hydrogen Bonding," Tetrahedron Letters. vol. 34, No. 6 pp. 963-966 (1993).
Kamo et al., "Membrane Potential of Mitochondria Measured with an Electrode Sensitive to Tetraphenyl Phosphonium and Relationship between Proton Electrochemical Potential and Phosphorylation Potential in Steady State," J. Membrane Biology. vol. 49 pp. 105-121 (1979).
Karahatay et al., "Clinical relevance of ceramide metabolism in the pathogenesis of human head and neck squamous cell carcinoma (HNSCC): Attenuation of $C_{18}$-ceramide in HNSCC tumors correlates with lymphovascular invasion and nodal metastasis," Cancer Letters. vol. 256 pp. 101-111 (2007).
Kaufmann, A.M., and Krise, J.P., "Lysosomal Sequestration of Amine-Containing Drugs: Analysis and Therapeutic Implications," Journal of Pharmaceutical Sciences. vol. 96, No. 4 pp. 729-746 (2007).
Kim et al., "Synthesis and evaluation of sphingoid analogs as inhibitors of sphingosine kinases," Bioorganic & Medicinal Chemistry. vol. 13 pp. 3475-3485 (2005).
Klymchenko et al., "Ultrasensitive two-color fluorescence probes for dipole potential in phospholipid membranes," PNAS. vol. 100, No. 20 pp. 11219-11224 (2003).

Koch et al., "Molecular Cloning and Characterization of a Full-length Complementary DNA Encoding Human Acid Ceramidase," The Journal of Biological Chemistry. vol. 271, No. 51 pp. 33110-33115 (1996).

Kornfeld, "The Biogenesis of Lysosomes," Annu. Rev. Cell Biol. vol. 5 pp. 483-525 (1989).

Koybasi et al., "Defects in Cell Growth Regulation by $C_{18:0}$-Ceramide and Longevity Assurance Gene 1 in Human Head and Neck Squamous Cell Carcinomas," The Journal of Biological Chemistry. vol. 279, No. 43 pp. 44311-44319 (2004).

Langer, "New methods of drug delivery," Science. vol. 249, No. 4976 pp. 1527-1533 (1990).

Lee et al., "Sphingosine-1-Phosphate as a Ligand for the G Protein-Coupled Receptor EDG-1," Science. vol. 279 pp. 1552-1555 (1998).

Levy et al., "Inhibition of calcification of bioprosthetic heart valves by local controlled-release diphosphonate," Science. vol. 228 p. 190 (1985).

Liu et al., "Acid ceramidase inhibition: a novel target for cancer therapy," Frontiers in Bioscience. vol. 13 pp. 2293-2298 (2008).

Liu et al., "Glutathione Regulation of Neutral Sphingomyelinase in Tumor Necrosis Factor-α-induced Cell Death," The Journal of Biological Chemistry. vol. 273, No. 18 pp. 11313-11320 (1998).

Lowe et al., "Prostate-specific expression of Bax delivered by an adenoviral vector induces apoptosis in LNCaP prostate cancer cells," Gene Therapy. vol. 8 pp. 1363-1371 (2001).

Macchia et al., "Design, Synthesis, and Characterization of the Antitumor Activity of Novel Ceramide Analogues," J. Med. Chem. vol. 44 pp. 3994-4000 (2001).

Maceyka et al., "Sphingosine kinase, sphingosine-1-phosphate, and apoptosis," Biochimica et Biohysica Acta. vol. 1585 pp. 193-201 (2002).

Makino et al., "Comparative study betvieen daily and 5-days-a-week administration of oral 5-fluorouracil chemotherapy in mice: determining the superior regimen," Cancer Chemother. Pharmacol. vol. 48 pp. 370-374 (2001).

Mao et al., "Cloning and Characterization of a Novel Human Alkaline Ceramidase," The Journal of Biological Chemistry. vol. 276, No. 28 pp. 36577-35688 (2001).

Medema et al., "FLICE is activated by association with the CD95 death-inducing signaling complex (DISC)," The EMBO Journal. vol. 16, No. 10 pp. 2794-2804 (1997).

Miller, A.D., and Buttimore, C., "Redesign of Retrovirus Packaging Cell Lines to Avoid Recombination Leading to Helper Virus Production," Molecular and Cellular Biology. vol. 6, No. 8 pp. 2895-2902 (1986).

Mimeault, "New advances on structural and biological functions of ceramide in apoptotic/necrotic cell death and cancer," FEBS Letters. vol. 530 pp. 9-16 (2002).

Miyashita, T., and Reed, J.C., "Tumor Suppressor p53 Is a Direct Transcriptional Activator of the Human *bax* Gene," Cell. vol. 80 pp. 293-299 (1995).

Modica-Napolitano, J.S., and Aprille, J.R., "Delocalized lipophilic cations selectively target the mitochondria of carcinoma cells," Advanced Drug Delivery Reviews. vol. 49 pp. 63-70 (2001).

Muzio et al., "FLICE Induced Apoptosis in a Cell-free System," The Journal of Biological Chemistry. vol. 272, No. 5 pp. 2952-2956 (1997).

Nakano, K., and Vousden, K.H., "*PUMA*, a Novel Proapoptotic Gene, Is Induced by p53," Molecular Cell. vol. 7 pp. 683-694 (2001).

Naldini et al., "In Vivo Gene Delivery and Stable Transduction of Nondividing Cells by a Lentiviral Vector," Science. vol. 272 pp. 263-267 (1996).

Nechushtan et al., "Bax and Bak Coalesce into Novel Mitochondria-associated Clusters during Apoptosis," The Journal of Cell Biology. vol. 153, No. 6 pp. 1265-1276 (2001).

Nimkar et al., "A Stereoselective Synthesis of Sphingosine, A Protein Kinase C Inhibitor," Tetrahedron Letters. vol. 29, No. 25 pp. 3037-3040 (1988).

Notification of Transmittal of the International Search Report and the Written Opinion of the International Searching Authority, or the Declaration corresponding to International Application No. PCT/US2009/063586 dated Mar. 5, 2010.

Notification of Transmittal of the International Search Report and the Written Opinion of the International Searching Authority, or the Declaration corresponding to International Application No. PCT/US2009/069583 dated Mar. 22, 2010.

Novgorodov et al., "Activation of sphingosine-1-phosphate receptor S1P5 inhibits oligodendrocyte progenitor migration," The FASEB Journal. vol. 21 pp. 1503-1514 (2007).

Novgorodov et al., "Positively Charged Ceramide Is a Potent Inducer of Mitochondrial Permabilization," Journal of Biological Chemistry. vol. 280, No. 16 pp. 16096-16105 (2005).

Obeid et al. "Programmed cell death induced by ceramide," Science. vol. 259, No. 5102 pp. 1769-1771 (1993).

Official Action corresponding to European Patent Application No. 05820909.9-2101 dated Oct. 2, 2009.

Official Action corresponding to U.S. Appl. No. 11/666,518 dated Aug. 5, 2010.

Ogretmen, B., and Hannun, Y.A., "Biologically Active Sphingolipids in Cancer Pathogenesis and Treatment," Nature. vol. 4 pp. 604-616 (2004).

Ogretmen et al., "Role of Ceramide in Mediating the Inhibition of Telomerase Activity in A549 Human Lung Adenocarcinoma Cells," The Journal of Biological Chemistry. vol. 276, No. 27 pp. 24901-24910 (2001).

Onda et al., "Molecular Recognition of Nucleotides by the Guanidinium Unit at the Surface of Aqueous Micelles and Bilayers. A Comparision of Microscopic and Macroscopic Interfaces," J. Am. Chem. Soc. vol. 118 pp. 8524-8530 (1996).

Orlinick, J.R., and Chao, M.V., "TNF-Related Ligands and Their Receptors," Cell. Signal. vol. 10, No. 8 pp. 543-551 (1998).

Papucci et al., Coenzyme Q10 Prevents Apoptosis by Inhibiting Mitochrondrial Depolarization Independently of Its Free Radical Scavenging Property, The Journal of Biological Chemistry. vol. 278, No. 30 pp. 28220-28228 (2003).

Pastan et al., "A retrovirus carrying an *MDR1* cDNA confers multidrug resistance and polarized expression of P-glycoprotein in MDCK cells," PNAS. vol. 85 pp. 4486-4490 (1988).

Paugh et al., "A selective sphingosine kinase 1 inhibitor integrates multiple molecular therapeutic targets in human leukemia," Blood. vol. 112, No. 4 pp. 1382-1391 (2008).

Perry, D.K., and Hannun, Y.A., "The role of ceramide in cell signaling," Biochimica et Biophysica Acta. vol. 1436 pp. 233-243 (1998).

Pettus et al., "The sphingosine kinase 1/sphingosine-1-phospate pathway mediates COX-2 induction and $PGE_2$ production in response to TNF-α," FASEB Journal. vol. 17 pp. 1411-1421 (2003).

Radin, "Designing Anticancer Drugs Via the Achilles Heel: Ceramide, Allylic Ketones, and Mitochondria," Bioorganic & Medicinal Chemistry. vol. 11 pp. 2123-2142 (2003).

Raisova et al., "Bcl-2 overexpression prevents apoptosis induced by ceramidase inhibitors in malignant melanoma and HaCaT keratinocytes," FEBS Letters. vol. 516 pp. 47-52 (2002).

Raisova et al., "Resistance to CD95/Fas-induced and ceramide-mediated apoptosis of human melanoma cells is caused by a defective mitochondrial cytochrome *c* release," FEBS Letters. vol. 473 pp. 27-32 (2000).

Rao et al., "$^{31}$P NMR Studies of the Arginine Kinase Reaction," The Journal of Biological Chemistry. vol. 251, No. 22 pp. 6981-6986 (1976).

Rautio et al., "Prodrugs: design and clinical applications," Nature Reviews. vol. 7 pp. 255-270 (2008).

Rebbaa et al., "Doxorubicin-induced apoptosis in caspase-8-deficient neuroblastoma cells in mediated through direct action on mitochondria," Cancer Chemother. Pharmacol. vol. 48 pp. 423-428 (2001).

Robbins and Angell, *Basic Pathology*, $2^{nd}$ Ed., W.B. Saunders Co., Philadelphia (1976), pp. 68-78 and 112-113.

Roberg et al., "Lysosomal Release of Cathepsin D Precedes Relocation of Cytochrome C and Loss of Mitochondrial Transmembrane Potential During Apoptosis Induced by Oxidative Stress," Free Radical Biology & Medicine. vol. 27, Nos. 11-12 pp. 1228-1237 (1999).

Rosania et al., "Combinatorial Approach to Organelle-Targeted Fluorescent Library Based on the Styryl Scaffold," Journal of the American Chemical Society. vol. 125 pp. 1130-1131 (2003).

Rossi et al., "Inhibition of growth and telomerase activity by novel cationic ceramide analogs with high solubility in human head and neck squamous cell carcinoma cells," Otolaryngology—Head and Neck Surgery. vol. 132, No. 1 pp. 55-62 (2005).

Rubinchik et al., "A Complex Adenovirus Vector That Delivers FASL-GFP with Combined Prostate-Specific and Tetracycline-Regulated Expression," Molecular Therapy. vol. 4, No. 5 pp. 416-426 (2001).

Sage et al., "Inhibition of Endothelial Cell Proliferation by SPARC Is Mediated Through a $Ca^{2+}$ -Binding EF-Hand Sequence," Journal of Cellular Biochemistry. vol. 57 pp. 127-140 (1995).

Samsel et al., "The Ceramide Analog, B13, Induces Apoptosis in Prostate Cancer Cell Lines and Inhibits Tumor Growth in Prostate Cancer Xenografts," The Prostate. vol. 58 pp. 382-393 (2004).

Scaffidi et al., "Two CD95 (APO-1/Fas) signaling pathways," The EMBO Journal. vol. 17, No. 6 pp. 1675-1687 (1998).

Schotte et al., "Non-specific effects of methyl ketone peptide inhibitors of caspases," FEBS Letters. vol. 442 pp. 117-121 (1999).

Schulze-Osthoff et al., "Apoptosis signaling by death receptors," Eur. J. Biochem. vol. 254 pp. 439-459 (1998).

Schwandner et al., "TNF Receptor Death Domain-associated Proteins TRADD and FADD Signal Activation of Acid Sphingomyelinase," The Journal of Biological Chemistry. vol. 273, No. 10 pp. 5916-5922 (1998).

Schwarzenberger et al., "Targeted Gene Transfer to Human Hematopoietic Progenitor Cell Lines Through the c-kit Receptor," Blood. vol. 87, No. 2 pp. 472-478 (1996).

Seelan et al., "Human Acid Ceramidase Is Overexpressed But Not Mutated in Prostate Cancer," Genes, Chromosomes & Cancer. vol. 29 pp. 137-146 (2000).

Selzner et al., "Induction of Apoptopic Cell Death and Prevention of Tumor Growth by Ceramide Analogues in Metastatic Human Colon Cancer," Cancer Research. vol. 61 pp. 1233-1240 (2001).

Senchenkov et al., "Targeting Ceramide Metabolism—a Strategy for Overcoming Drug Resistance," J. Natl. Cancer Inst. vol. 93 pp. 347-357 (2001).

Shi et al., "Complex Functions of Mutant *p*53 Alleles From Human Prostate Cancer," The Prostate. vol. 51 pp. 59-72 (2002).

Siskind et al., "Ceramide Channels Increase the Permeability of the Mitochondrial Outer Membrane to Small Proteins," The Journal of Biological Chemistry. vol. 277, No. 30 pp. 26796-26803 (2002).

Sobel, R.E., and Sadar, M.D., "Cell Lines Used in Prostate Cancer Research: A Compendium of Old and New Lines—Part 1," The Journal of Urology. vol. 173 pp. 342-359 (2005).

Song et al., "Kinetics and Mechanisms of Activation of α-Amino Acid Ester Prodrugs of Camptothecins," J. Med. Chem. vol. 49 pp. 4344-4355 (2006).

Sullards, M.C., and Merrill, Jr., A.H., "Analysis of Sphingosine 1-Phosphate, Ceramides, and Other Bioactive Sphingolipids by High-Performance Liquid Chromatography-Tandem Mass Spectrometry," Sci. STKE. vol. 67 pp. 1-11 (2001).

Sundararaj et al., "Rapid Shortening of Telomere Length in Response to Ceramide Involves the Inhibition of Telomere Binding Activity of Nuclear Glyceraldehyde-3-phosphate Dehydrogenase," The Journal of Biological Chemistry. vol. 279, No. 7 pp. 6152-6162 (2004).

Szalai et al., "Apoptosis driven by $IP_3$-linked mitochondrial calcium signals," The EMBO Journal. vol. 18, No. 22 pp. 6349-6361 (1999).

Szulc et al., "Novel analogs of D-*ef*-MAPP and B13. Part 1: Synthesis and evaluation as potential anticancer agents," Bioorganic & Medicinal Chemistry. vol. 16 pp. 1015-1031 (2008).

Szulc et al., "Tailoring structure-function and targeting properties of ceramides by site-specific cationization," Bioorganic & Medicinal Chemistry. vol. 14 pp. 7083-7104 (2006).

Takahashi et al., "Human Fas ligand: gene structure, chromosomal location and species specificity," International Immunology. vol. 6, No. 10 pp. 1567-1574 (1994).

Takeya et al., "Synergistic effect of sphingosine 1-phosphate on thrombin-induced tissue factor expression in endothelial cells," Blood. vol. 102 pp. 1693-1700 (2003).

Tepper et al., "CD95/Fas-induced Ceramide Formation Proceeds with Slow Kinetics and Is Not Blocked by Caspase-3/CPP32 Inhibition," The Journal of Biological Chemistry. vol. 272, No. 39 pp. 24308-24312 (1997).

Tepper et al., "Role for ceramide as an endogenous mediator of Fas-induced cytotoxicity," PNAS. vol. 92 pp. 8443-8447 (1995).

Thornberry, N.A., and Lazebnik, Y., "Caspases: Enemies Within," Science. vol. 281 pp. 1312-1316 (1998).

Tolsma et al., "Peptides Derived from Two Separate Domains of the Matrix Protein Thrombospondin-1 Have Anti-Angiogenic Activity," The Journal of Cell Biology. vol. 122, No. 2 pp. 497-511 (1993).

Trnka, T.M., and Grubbs, R.H., "The Development of $L_2X_2Ru=CHR$ Olefin Metathesis Catalysts: An Organometallic Success Story," Acc. Chem. Res. vol. 34 pp. 18-29 (2001).

Usta et al., "Structural Requirements of Ceramide and Sphingosine Based Inhibitors of Mitochondrial Ceramidase," Biochemistry. vol. 40 pp. 9657-9668 (2001).

van Moorsel et al., "Scheduling of Gemcitabine and Cisplatin in Lewis Lung Tumour Bearing Mice," European Journal of Cancer. vol. 35, No. 5 pp. 808-814 (1999).

Veerman et al., "Antitumor activity of prolonged as compared with bolus administration of 2',2'-difluorodeoxycytidine in vivo against murine colon tumors," Cancer Chemother. Pharmacol. pp. 335-342 (1996).

Vig et al., "Amino Acid Ester Prodrugs of Floxuridine: Synthesis and Effects of Structure, Stereochemistry, and Site of Esterification on the Rate of Hydrolysis," Pharmaceutical Research. vol. 20, No. 9 pp. 1381-1388 (2003).

Volk, C.A., and Köck, M., "Viscosamine: The First Naturally Occurring Trimeric 3-Alkyl Pyridinium Alkaloid," Organic Letters. vol. 5, No. 20 pp. 3567-3569 (2003).

von Haefen et al., "Ceramide induces mitochondrial activation and apoptosis via a Bax-dependent pathway in human carcinoma cells," Oncogene. vol. 21 pp. 4009-4019 (2002).

Wagenknecht et al., "C2-ceramide signaling in glioma cells: synergistic enhancement of CD95-mediated, caspase-dependent apoptosis," Cell Death and Differentiation. vol. 8 pp. 595-602 (2001).

Watterson et al., "Pleiotropic actions of sphingosine-1-phosphate," Progress in Lipid Research. vol. 42 pp. 344-357 (2003).

Weissman, "Themes and Variations on Ubiquitylation," Nature Reviews Molecular Cell Biology. vol. 2 pp. 169-178 (2001).

Wyllie et al., "Cell Death: The Significance of Apoptosis," International Review of Cytology. vol. 68 pp. 251-306 (1980).

Yamanaka et al., "Engraftment of Tonsillar Mononuclear Cells in Human Skin/SCID Mouse Chimera—Validation of a Nove Xenogeneic Transplantation Model for Autoimmune Diseases—," Microbiol. Immunol. vol. 45, No. 7 pp. 507-514 (2001).

Yatomi et al., "Sphingosine-1-Phosphate: A Platelet-Activating Sphingolipid Released From Agonist-Stimulated Human Platelets," Blood. vol. 86, No. 1 pp. 193-202 (1995).

Zeidan et al., "Acid Ceramidase but Not Acid Sphingomyelinase Is Required for Tumor Necrosis Factor-α-induced PGE2 Production," The Journal of Biological Chemistry. vol. 281, No. 34 pp. 24695-24703 (2006).

Official Action corresponding to Canadian Patent Application No. 2,585,775 dated Apr. 16, 2012.

Dahm et al., "Mitochondrially targeted ceramide LCL-30 inhibits colorectal cancer in mice," British Journal of Cancer. vol. 98 pp. 98-105 (2008).

Dindo et al., "Cationic long-chain ceramide LCL-30 induces cell death by mitochondrial targeting in SW403 cells," Molecular Cancer Therapeutics. vol. 5, No. 6 pp. 1520-1529 (2006).

Notice of Allowance corresponding to U.S. Appl. No. 11/666,518 dated Aug. 9, 2011.

Senkai et al., "Potent Antitumor Activity of a Novel Cationic Pyridinium-Ceramide Alone or in Combination with Gemcitabine against Human Head and Neck Squamous Cell Carcinomas in Vitro and in Vivo," The Journal of Pharmacology and Experimental Therapeutics. vol. 317, No. 3 pp. 1188-1199 (2006).

"Ceramide," Wikipedia, <http://en.wikipedia.org/wiki/Ceramide> pp. 1-4 (Accessed on Nov. 4, 2010.

Clement, "In-vitro-Untersuchungen zur mikrosomalen N-Oxidation einiger Guanidine," Arch. Pharm. (Weinheim). vol. 319 pp. 961-968 (1986) [ABSTRACT].

Extended European Search Report corresponding to European Patent Application No. 09 825 496.4-2123 dated Mar. 7, 2012.

Extended European Search Report corresponding to European Patent Application No. 09 837 076.0-1211 dated Dec. 14, 2011.
Larsen et al., "Synthesis and Biological Activity of Analogues of the Antidiabetic/antiobesity Agent 3-Guanidinopropionic Acid: Discovery of a Novel Aminoguanidinoacetic Acid Antidiabetic Agent," Journal of Medicinal Chemistry. vol. 44, No. 8 pp. 1217-1230 (2001).
Notification Concerning Transmittal of International Preliminary Report on Patentability (Chapter 1 of the Patent Copperation Treaty) corresponding to International Patent Application No. PCT/US2009/063586 dated May 19, 2011.
Notification Concerning Transmittal of International Preliminary Report on Patentability (Chapter 1 of the Patent Cooperation Treaty) corresponding to International Patent Application No. PCT/US2009/069583 dated Jul. 14, 2011.
Official Action corresponding to Canadian Patent Application No. 2,585,645 dated Mar. 13, 2012.
Official Action corresponding to European Patent Application No. 05 820 909.9-2101 dated Sep. 27, 2011.
Official Action corresponding to European Patent Application No. 05 821 150.9-1211 dated Mar. 28, 2012.
Separovic et al., "C16-Ceramide Analog Combined with Pc 4 Photodynamic Therapy Evokes Enhanced Total Ceramide Accumulation, Promotion of DEVDase Activation in the Absence of Apoptosis, and Augmented Overall Cell Killing," Journal of Lipids. pp. 1-9 (2011).
Shapiro et al., "Hypoglycemic Agents, III. 1-3 N1-Alkyl- and Aralkylbiguanides," Journal of the American Chemical Society. vol. 81 pp. 3728-3736 (1958).
Extended European Search Report corresponding to European Patent Application No. 05821150.9-1211 dated Feb. 10, 2011.
Fujii, A., and Cook, E.S., "Probiotics. Antistaphylococcal and Antifibrinolytic Activities of ω-Guanidino Acids and ω-Guanidinoacyl-L-histidines," Journal of Medicinal Chemistry. vol. 16, No. 12, pp. 1409-1411 (1973).
Interview Summary corresponding to U.S. Appl. No. 11/666,518 dated Nov. 26, 2010.
Interview Summary corresponding to U.S. Appl. No. 11/666,518 dated May 2, 2011.
Lazewska et al., "Piperidine-containing histamine $H_3$-receptor antagonists of the carbamate series: variation of the spacer length," Pharmazie. vol. 56, No. 12 pp. 927-932 (2001).
Libby et al., "A Cascade Model for Restenosis: A Special Case of Atherosclerosis Progression," Circulation. vol. 86, No. 6, Suppl. III-47-III-52 (1992).
Lim et al., "Synthesis and Cytotoxicity of New 3-Alkyl-1-(1-methyl-2-phenylethyl)ureas Related to Ceramide," Archives of Pharmacal Research. vol. 26, No. 4 pp. 270-274 (2003).
Mahboob, S., and Dhar, M.L., "Studies in Potential Amoebicides: Part II—Synthesis of Some Polymethylene Diamines," Journal of Scientific & Industrial Research, vol. 14B pp. 1-6 (1955).
Mathias et al., "Signal transduction of stress via ceramide," Biochem. J. vol. 335 pp. 465-480 (1998).
Mitani et al., "Transduction of Human Bone Marrow by Adenoviral Vector," Human Gene Therapy. vol. 5 pp. 941-948 (1994).
Nussbaumer et al., "One-step labelling of sphingolipids vis a scrambling cross-metathesis reaction," Chem. Commun. vol. 40, pp. 5086-5087 (2005).
Official Action corresponding to U.S. Appl. No. 11/666,518 dated Jan. 6, 2011.
Seebach et al., "Lithiation and Electrophilic Substitution at α-Methylene Groups of Nitrosamines. Reactivity Umpolung of Secondary Amines," Chemische Berichte. vol. 110, No. 5 pp. 1852-1865 (1977) [ABSTRACT].

Taha et al., "A house divided: ceramide, sphingosine, and sphingsine-1-phosphate in programmed cell death," Biochim. Biophys. Acta. vol. 1758, No. 12 pp. 2027-2036 (2006).
Ueoka et al., "Isokinetic Discrimination of Artificial Membrane Systems in the Enantioselective Hydrolysis," Tetrahedron Letters, vol. 25, No. 13 pp. 1363-1366 (1984).
Yamaguchi et al., "Copper(II) Reagent-Promoted Degradation of $N,N'$-dialkyldiazenedicarboxamides," Bulletin of the Chemical Society of Japan, vol. 75, No. 2 pp. 329-333 (2002).
Offical Action corresponding to U.S. Appl. No. 13/127,888 dated Feb. 4, 2013.
Official Action corresponding to Chinese Patent Application Serial No. 200980154007.6 dated Mar. 13, 2013.
Official Action corresponding to U.S. Appl. No. 13/127,888 dated Mar. 14, 2013.
Official Action corresponding to U.S. Appl. No. 13/142,421 dated Apr. 30, 2013.
CommunIcation under Rule 71(3) EPC corresponding to European Patent Application No. 05 820 909.9-2101 dated Nov. 2, 2012.
Official Action corresponding to U.S. Appl. No. 13/127,888 dated Feb. 4, 2013.
Official Action corresponding to Canadian Patent Application No. 2,585,645 dated Jan. 16, 2013.
Communication under Rule 71(3) EPC corresponding to European Patent Application No. 05 820 909.9-2101 dated Jul. 16, 2013.
Interview Summary corresponding to U.S. Appl. No. 13/127,888 dated Jun. 20, 2013.
Kast et al., "Suppressing Glioblastoma Stem Cell Function by Aldehyde Dehydrogenase Inhibition with Chloramphenicol or Disulfiram as a New Treatment Adjunct: A Hypothesis," Current Stem Cell Research and Therapy. vol. 4, No. 4 pp. 314-317 (2009).
Notice of Allowance corresponding to Canadian Patent Application No. 2,585,775 dated Feb. 1, 2013.

\* cited by examiner

*Primary Examiner* — Taylor Victor Oh

(74) *Attorney, Agent, or Firm* — Jenkins, Wilson, Taylor & Hunt, P.A.

(57) ABSTRACT

The invention provides the compounds of formula (): and pharmaceutically acceptable salts thereof, wherein $R_1$, $R_2$, $R_3$, $R_4$, A, X, Y, a, b and n are as defined herein. Also disclosed are methods for making the compounds of formula (I) and their use in treating or preventing diseases associated with cell overproliferation and dysfunctional sphingolipid signal transduction. The invention also encompasses the use of the compounds in combination with an apoptosis-signaling ligand, such as Fas ligand. Preferably, the Fas ligand is administered in the form of a gene therapy agent.

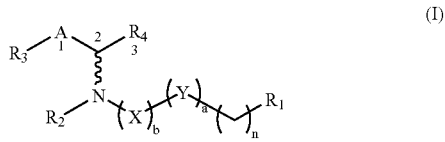

13 Claims, 34 Drawing Sheets

Figure 1:
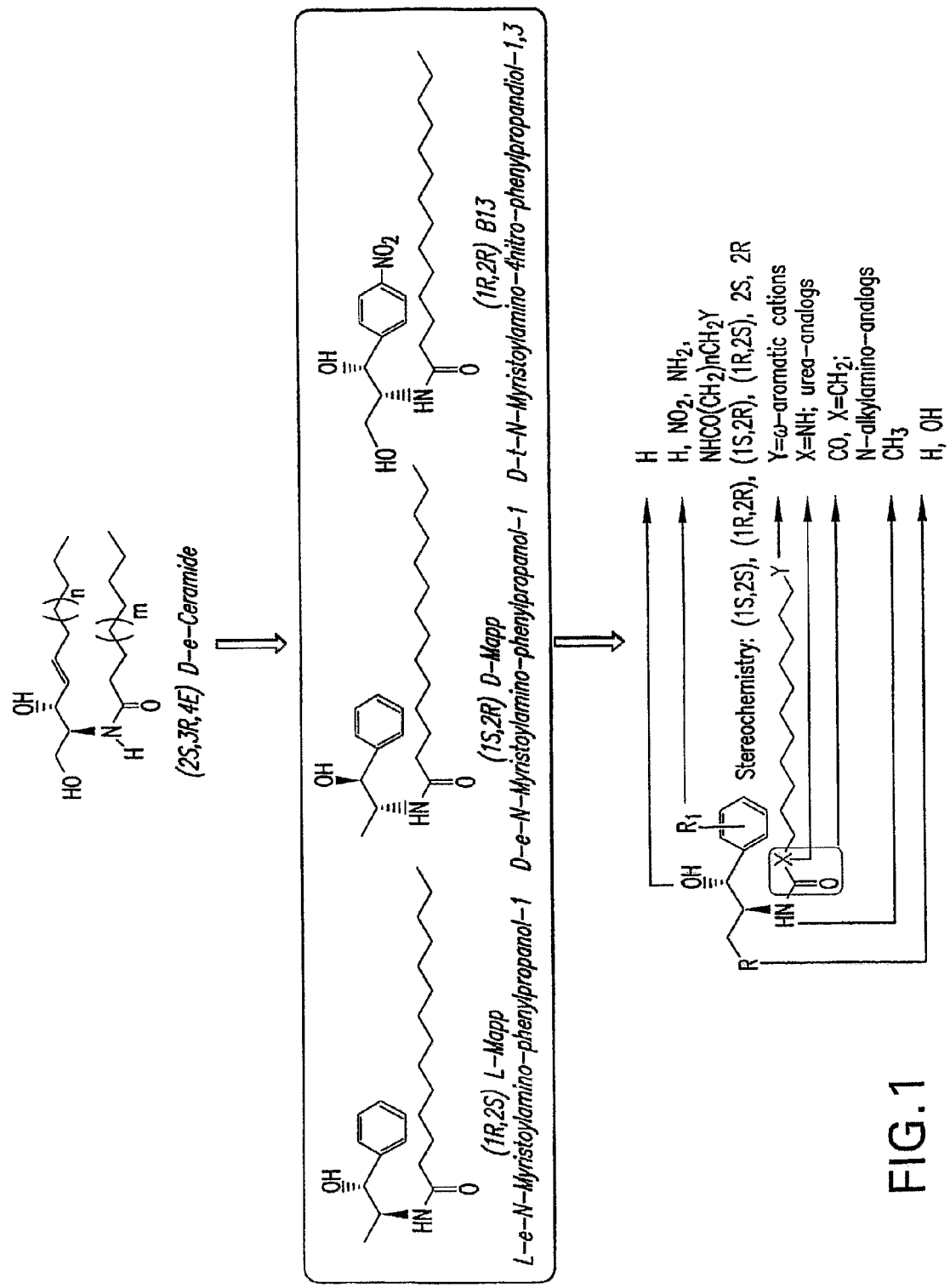

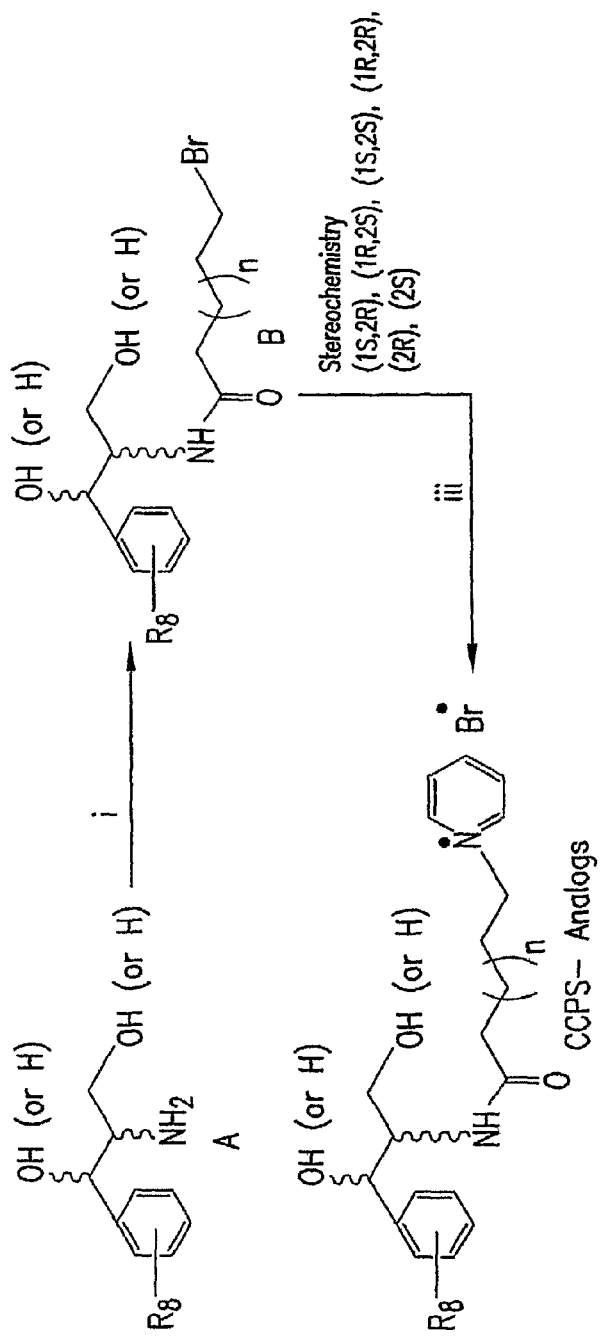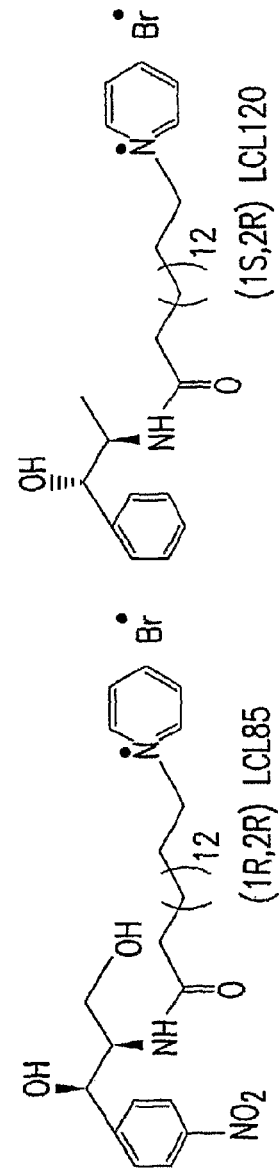
FIG. 2E

* = p>0.01
** = p>0.01

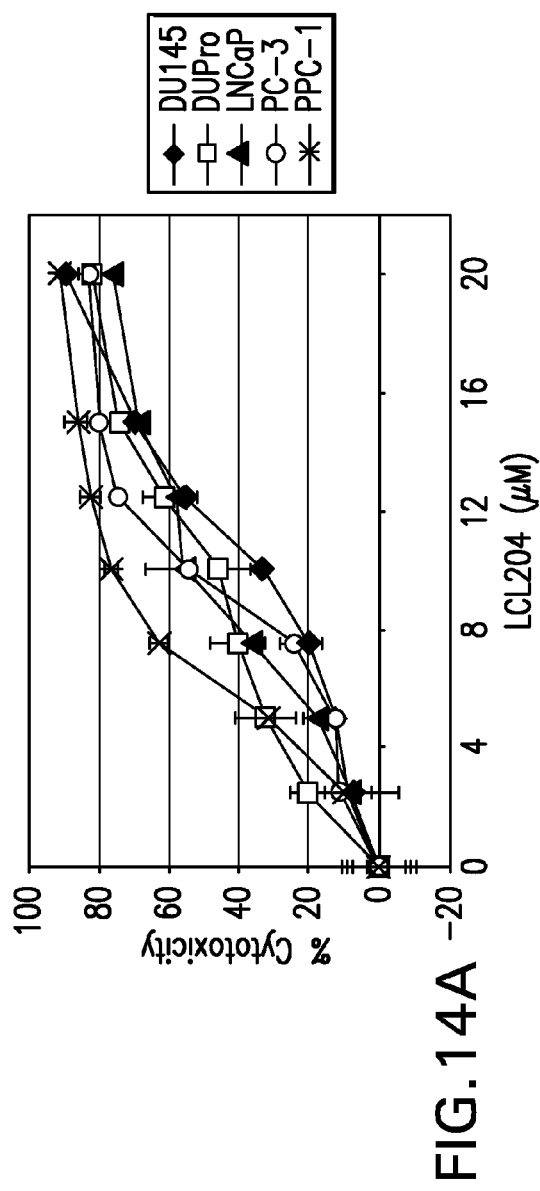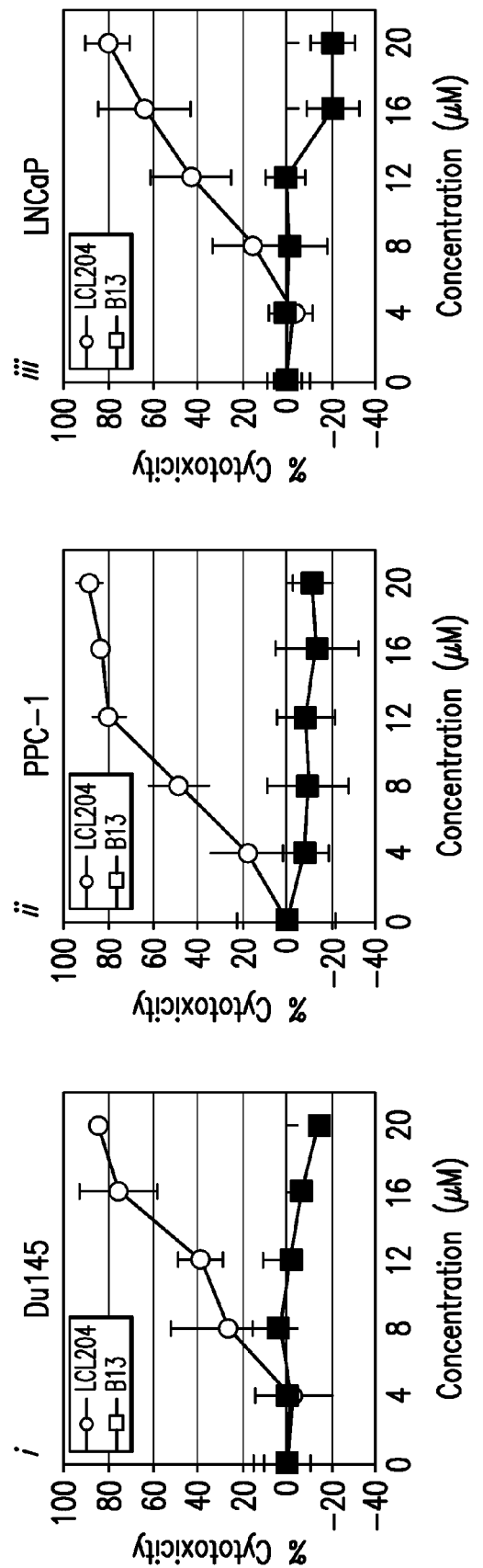
FIG. 14A
FIG. 14B

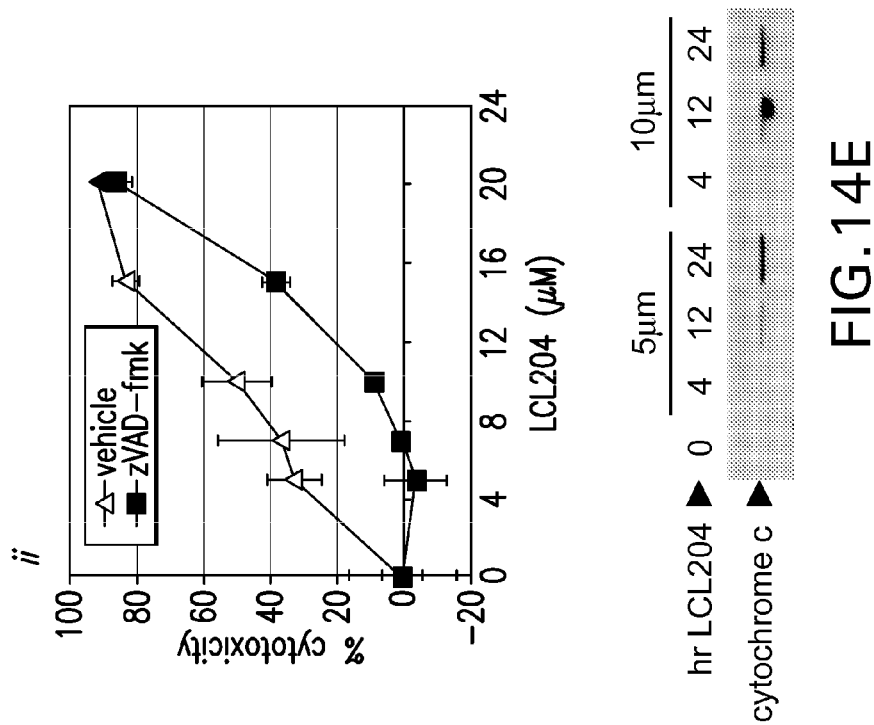
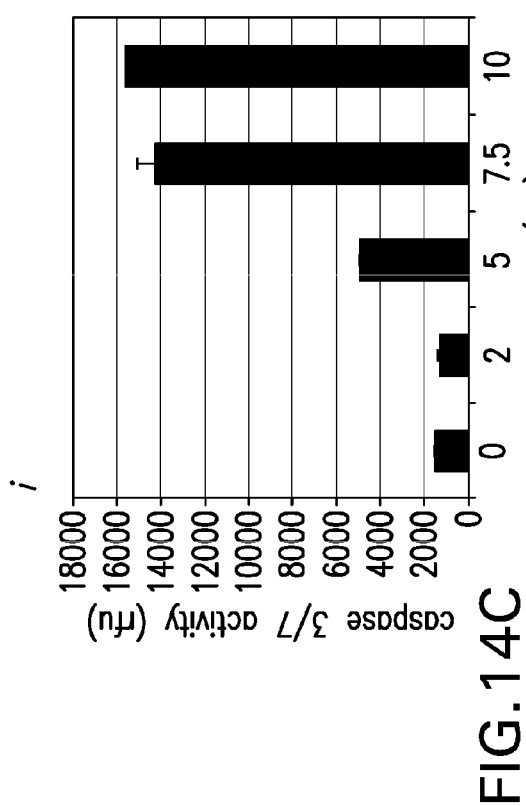
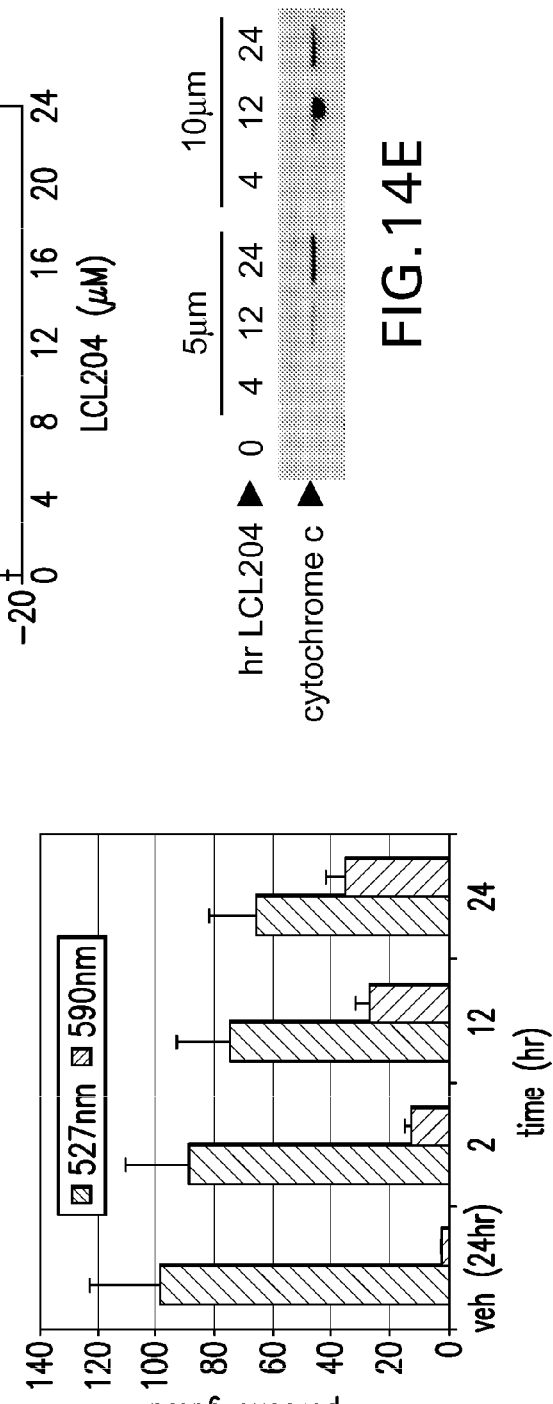
FIG.14C
FIG.14D
FIG.14E

*i*
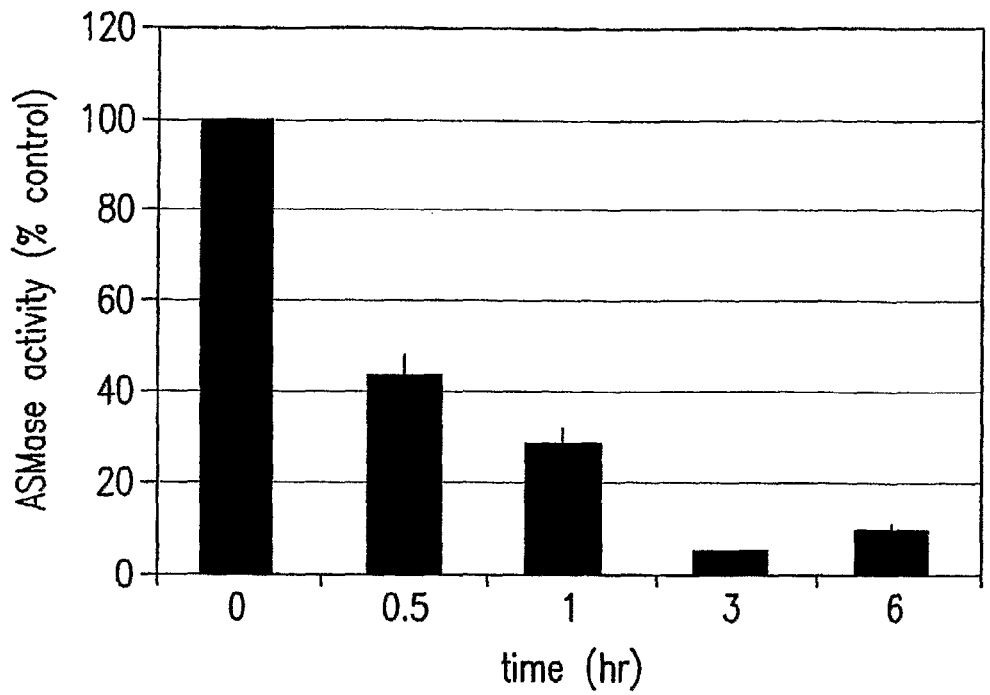
*ii*
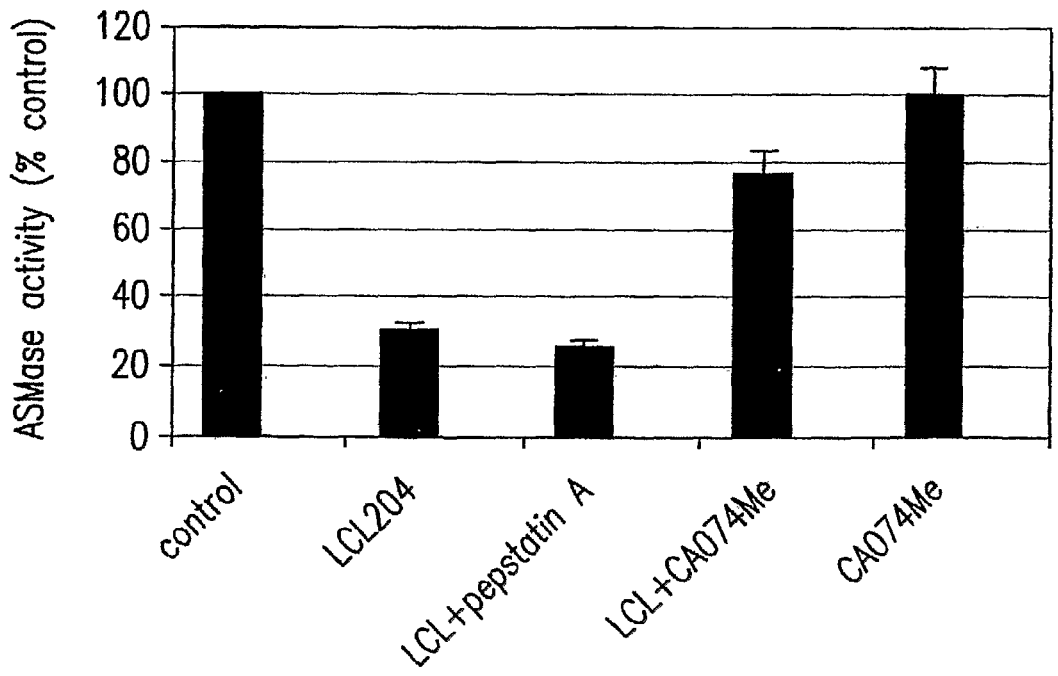
FIG. 16D

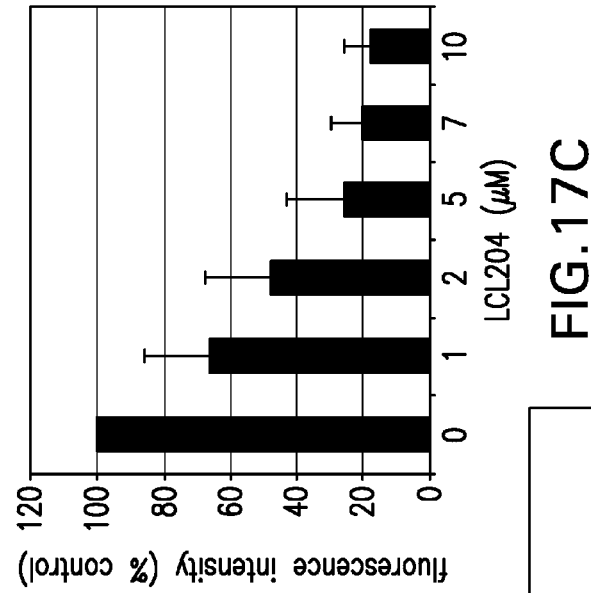
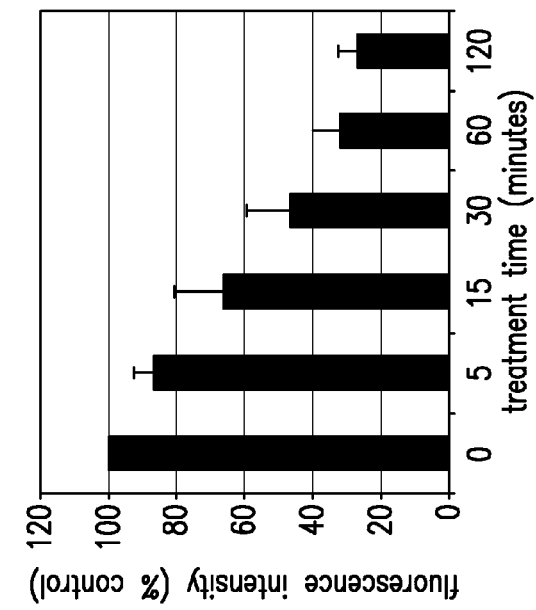
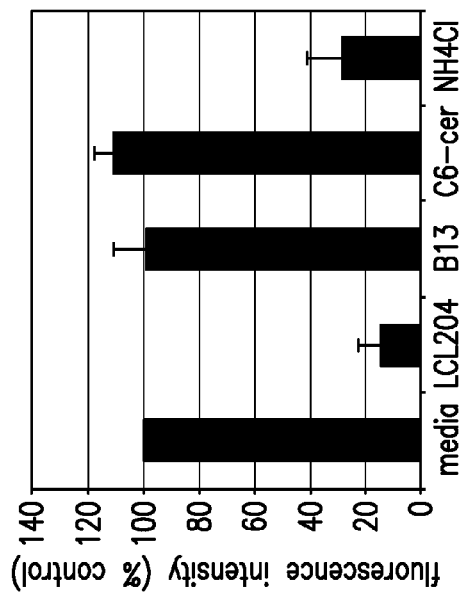
FIG. 17A
FIG. 17B
FIG. 17C

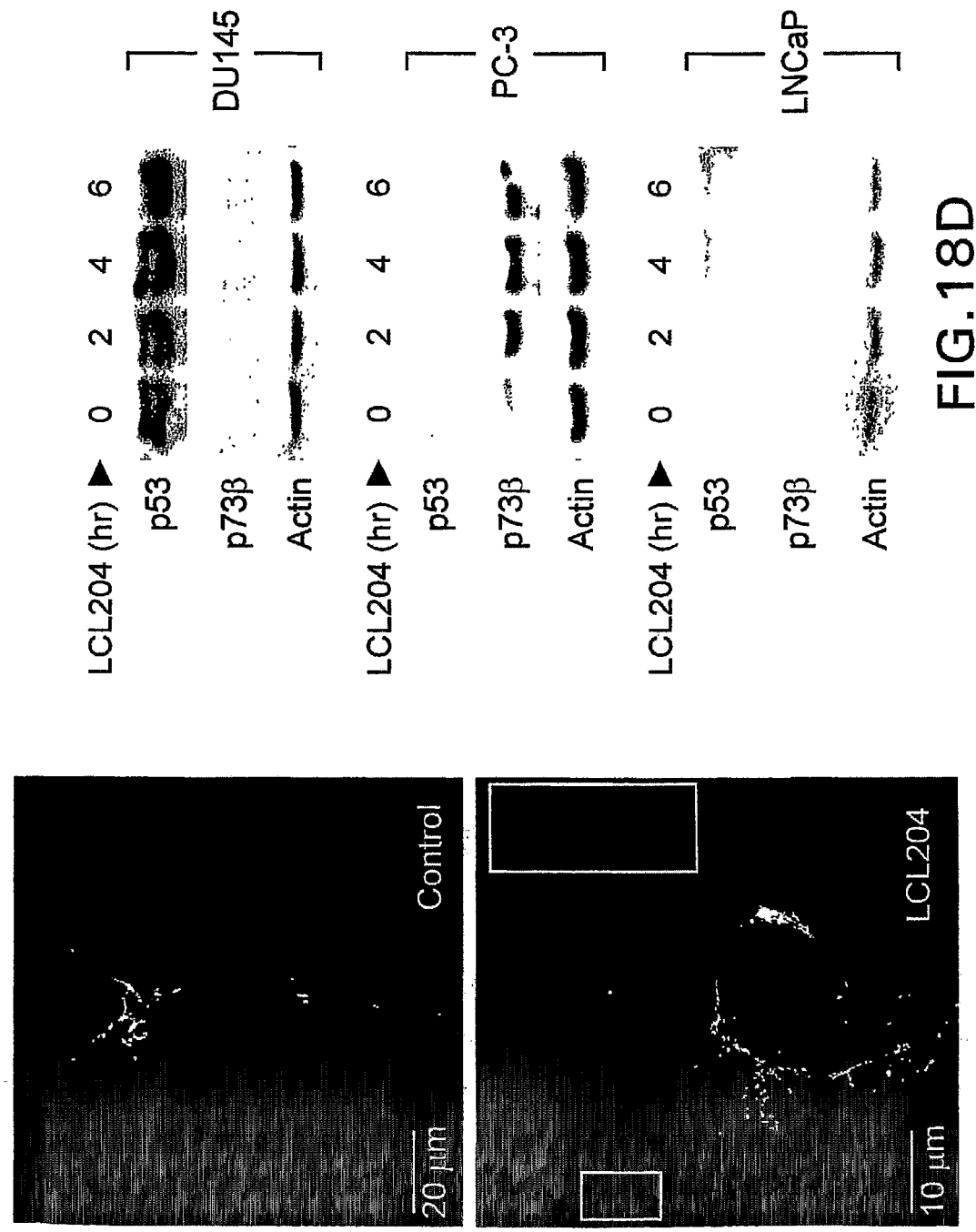

CERAMIDES AND APOPTOSIS-SIGNALING LIGAND

This application claims priority to U.S. provisional application No. 60/623,293, filed Oct. 29, 2004, which is incorporated herein by reference in its entirety.

This invention was made with government support under SCHE grant ROO-MO1:#83145 and grant numbers NIH-NCI 1PO1-CA97132, 1R24 CA82933-01 and HCC/DOD grant for Translational Research and Cancer Prevention Control and Risk Factor. The government has certain rights in the invention.

1. FIELD OF THE INVENTION

The present invention relates to ceramide analogs, and uses of such ceramide analogs and apoptosis-signaling ligand in the treatment of diseases associated with cell overproliferation.

2. BACKGROUND

2.1 Ceramide

Ceramide is a potent signal transducer that affects cell growth, differentiation and death (Hannun, Y. A. (1996) *Science* 274, 1855-1859; Obeid, L. M., Linardic, C. M., Karolak, L. A., and Hannun, Y. A. (1993) Science 259, 1769-1771; Perry, D. K. and Hannun, Y. A., (1998) *Biochim Biophys Acta* 436, 233-243). It occupies a central position in sphingolipid metabolism. As an acceptor of carbohydrates, phosphorylcholine and phosphate, it serves as precursor of the various complex sphingolipids. Alternatively, the enzymatic breakdown of these sphingolipids releases ceramide which may consequently be hydrolyzed into fatty acid and sphingosine; the latter exerting effector functions on its own as well as acting as a precursor of sphingosine phosphate, another signal mediator and regulator of various cell functions. Ceramides are generated by hydrolysis of sphingomyelin in response to different stimuli, such as tumor necrosis factor, Fas/CD95 ligand, interleukin-1, and vitamin D3. A controlled level of ceramide, therefore, reflects an intricate balance between the catabolic and anabolic pathways of ceramide.

One of the most studied effects of ceramide is the ability to induce cell death. Endogenous ceramide levels are elevated in tumors after irradiation or therapy with anticancer drugs (Bose et al., *Cell,* 82:405-414, 1995; Selzner et al., *Cancer Res.* 61:1233-1240, 2001). Exogenous ceramides emerged as a promising new approach for cancer therapy. It has been shown that exogenous ceramide can induce cell death in a variety of cancer cell types with normal cells being less susceptible (von Haefen et al., *Oncogene* 21:4009-4019, 2002; Jones et al., *Hepatology,* 30:215-222, 1999).

Most studies of the effects of ceramides on cancer cells are restricted to the use of short-chain ceramides (C2-C8) because naturally occurring long-chain ceramides (C16-C24) are unable to penetrate cell membranes. Thus, there is a need for developing ceramides and analogs that can be administered as a drug or to generate or regulate the endogenous ceramide level and composition.

The present invention provides a class of ceramide analogs which have the desirable biological and pharmacological properties making these compounds suitable for development as therapeutic agents or drug delivery vehicles.

2.2 Apoptosis-Signaling Ligand

Apoptosis, or programmed cell death, is a genetically controlled response for cells to commit suicide. The symptoms of apoptosis are viability loss accompanied by cytotoxic boiling, chromatin condensation, and DNA fragmentation (Wyllie et al. (1980) "Cell death: the significance of apoptosis" Int. Rev. Cytol. 68: 251-306). The apoptotic process has important roles in regulating the development of tissues, the sizes and shapes of organs, and the life span of cells. In the process of tissue and organ development apoptosis accounts for most or all of the apoptosis responsible for tissue modeling in vertebrate development for the physiological cell death in the course of normal tissue turn over.

The apoptotic process involves a receptor that mediates programmed cells death upon binding with an apoptosis signaling ligand. The receptor may be a cell surface receptor that is membrane-bound, or resides in cytoplasm or nucleus. A prominent example of such an apoptosis-mediating receptor belongs to the tumor necrosis factor (TNF) receptor superfamily. The TNF receptor superfamily is defined by the presence of related, cysteine-rich, extracellular domains. Examples of TNF receptors include, but are not limited to NTR/GFR (p75) such as NGF, BDNF, NT-3 and NT-4, TNF-R1 (CD120a), TNF-R2 (CD120b), Fas (CD5/Apo-1), DR3 (TRAMP/WSL-1), DR4(TRAIL-R1), DR5(TRAIL-R2), DcR1(TRAIL-R3), DcR2(TRAIL-R4), CD30, CD40, Cd27, 4-1 BB (CD137), OX-40, LT-ssR, human HVEM (herpes virus early mediator), OPG (osteoprotegerin)/OC1 F, and RANK (Ashkenazi and Dixit (1999) Curr. Opin. Cell Biol. 11: 255-260). All of the receptors are type I transmembrane proteins with an extracellular region composed of two-six cysteine rich domains that are about 25% identity among members and contribute to ligand binding. Fas, TNF-R1, TRAIL-DR4, DR5, TRAMP (DR3), CAR1 have similar cytoplasmic domains. Sequence comparison of the intracellular region of these receptors revealed a homologous, well-conserved region of about 80 amino acids called the death domain. (Orlinck and Chao (1998) Cell Signal 10: 543-551).

The ligands that bind to the receptors in the TNF receptor superfamily include, but are not limited to, neorotrophins, TNF-a, Fas ligand(FasL/CD-95L/Apo-1L), TRAIL/Apo-2L, CD30L, CD40L, CD27L, 4-1 BBL, OX-40L, and lymphotoxin (LT-a). A common feature of the ligands is that all active ligands are composed of three identical subunits (trimers) and activate their respective receptors by oligomerization (Schulze-Osthoff et al. (1998) Eur. J. Biochem. 254; 439-459).

Fas ligand (FasL, CD95L or APO-1L) is a 40 kDa type II membrane protein belonging to the Tumor Necrosis Factor (TNF) family. Its receptor, Fas (CD95 or APO-1) is a 45 kDa type I membrane protein belonging to the TNF/NGF (Nerve Growth Factor) superfamily of receptors (Takahashi et al., *International Immunology* 6, 1567-74). Following engagement with its ligand, Fas functions to initiate an apoptotic signal. This signal originates at the death inducing signaling complex or DISC and is believed to form on the cytoplasmic face of the plasma membrane around the cytoplasmic domain of Fas. The DISC, in part, is composed of Fas, an adapter molecule (FADD/MORT), RIP, and pro-caspase 8 (FLICE/MACH) (Ashkenazi et al., *Science.* 281, 1305-8). Upon Fas stimulation, FADD and pro-caspase 8 are recruited to Fas enabling pro-caspase 8 to be autocatalytically activated (Medema et al., *EMBO Journal* 16, 2794-804). Active caspase 8, in turn, cleaves and/or activates several downstream substrates including the effector caspases 3 and 7 (Muzio et al., *Journal of Biological Chemistry* 272, 2952-6; Type I pathway) or Bid which acts through the mitochondrial Type II pathway to amplify PCD signals. Both pathways have been described (Scaffidi et al., *EMBO Journal.* 17, 1675-87).

Fas is a widely expressed protein found on the plasma membrane in most tissues including the prostate. In contrast, FasL expression appears to be more tightly regulated on the plasma membrane. Membrane FasL (mFasL) expression has been detected in immune privileged tissue, for example; testis, retina, cornea, and in T and NK cells.

Citation of references hereinabove shall not be construed as an admission that such references are prior art to the present invention.

3. SUMMARY OF THE INVENTION

The invention is relates to ceramide modulators, methods for making these ceramide modulators, and the use of these ceramide analogs for treating or preventing diseases associated with cell overproliferation and/or disfunction of sphinogolipid signal transduction.

In one embodiment, the invention relates to a compound of formula (I):

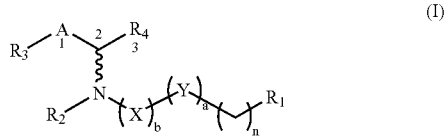

and pharmaceutically acceptable salts thereof, wherein:

$R_1$ is —H, —OH, —SH, —NH$_2$, —Cl, —Br, —I, —C(O)OH, —C(O)NH$_2$, —NH(C=NH)NH$_2$, NH(R$_2$), or a —N-heterocycle having from 5 to 6 atoms in the ring;

$R_2$ is —H or —(C$_1$-C$_6$)alkyl;

$R_3$ is -phenyl; five-membered monocyclic heterocycle; six-membered monocyclic heterocycle; five- and five-membered bicyclic heterocycle; six- and six-membered bicyclic heterocycle; five- and six-membered bicyclic heterocycle; five-, five-, and five-membered tricylic heterocycle; six-, six-, and six membered tricylic heterocycle; five-, five-, and six-membered tricylic heterocycle; five-, six-, and six-membered tricylic heterocycle; six-, five, and six-membered tricylic heterocycle; five-, six-, and five-membered tricylic heterocycle; each of the foregoing being optionally substituted with one or more —R$_5$;

$R_4$ is —H, —(C$_1$-C$_6$)alkyl, —CH$_2$(OH), —SH, —NH$_2$, —CH$_2$Cl, —CH$_2$Br, —CH$_2$I, —C(O)OH, or C(O)NH$_2$;

$R_5$ is —(C$_1$-C$_6$)alkyl, —F, —Cl, —Br, —I, —NH(R$_{2a}$), —NO$_2$, or an amide of formula

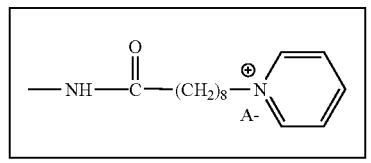

$R_{2a}$ is —H or —(C$_1$-C$_6$)alkyl;

X is —CH((C$_1$-C$_6$)alkyl)-, —C(O)—, —C(S)-, or —CH$_2$—;

Y is —C(O)—, —N(H)—, —O— or —CH$_2$—;

A is —CH$_2$—, —CHOH—;

a is 0 or 1;

b is 0 or 1; and n is an integer from 2 to 22.

The invention is directed to N-alkylamino-phenylaminoalcohols, urea phenylaminoalcohols, pyridinium N-acylaminophenylaminoalcohols and other cation analogs of these compounds.

In another embodiment, the invention relates to methods for making compounds of formula (I).

In various preferred embodiments, the invention encompasses compounds that induce cell differentiation, such as but not limited to, apoptosis and altering cell phenotype.

In yet another embodiment, the invention provides the use of the compounds of formula (I) to treat diseases associated with cell overproliferation or dysfunctional sphingolipid signal transduction. In a specific embodiment, the compounds of formula (I) are used to induce cell death, preferably cancer cell death. One useful property of the compounds of the invention is the preferential distribution to organelles that have an overall positive charge, such as the lysosome. These compounds can be used as an inhibitor of ceramidase enzymes that are present in these organelles, such as acid ceramidases. The targeting of ceramidase inhibitors to certain organelles will enhance the specificity of their inhibitory actions and yield desirable pharmacological profiles.

The present invention encompasses methods, pharmaceutical compositions, and dosage forms for the treatment or prevention of various cancers and hyperproliferative diseases in animals, including humans. The methods of the invention comprise administering to a patient in need of such treatment or prevention a therapeutically or prophylactically effective amount of a compound of the invention, or a pharmaceutically acceptable salt, or solvate thereof.

Pharmaceutical compositions of the invention comprise a therapeutically or prophylactically effective amount of a compound of formula (I). Preferred compounds are those that are active in inducing cell death, decreasing cell survival and viability (e.g., which can be demonstrated in vitro assays, or animal models). Pharmaceutical compositions of the invention can further comprise other anticancer drug or therapeutic substances.

In another embodiment, the invention provides the use of a compound of formula (I) in combination with another therapeutic modality that induce apoptosis. Preferably, the other therapeutic modality is not a phenylaminoalcohol-related compound. In a preferred embodiment, the other therapeutic modality is Fas ligand or an analog thereof. Most preferably, the Fas ligand or the analog is delivered by gene therapy techniques.

In another embodiment, the compounds of formula (I) may be used to activate acid ceramidase. In a specific embodiment, the compound is LCL16. In a specific embodiment, the compound can be used to treat Fabry disease or diseases where ceramide accumulates within cells.

In a specific embodiment, the compound of the present invention formula I, wherein X is ((O)— or —C(S) and Y is —N(H)— is used for the treatment of diseases that are related to an increased level of endogenous ceramide. In a specific embodiment, the disease is Fabry disease.

In another embodiment, the compound of the present invention having formula I, wherein X is —CH$_2$—, —CH(CC$_1$-($_6$)alkyl)- and Y is —CH$_2$—, —C(O)—, N(H)—, or —O— is used for the treatment of diseases that are related to a decrease in level of endogenous ceramide or a hyperproliferative disease.

4. BRIEF DESCRIPTION OF THE FIGURES

FIG. 1. Formula for disclosed class of biologically active compounds, L-Mapp, D-Mapp and B13, affecting acid ceramidase (A-CDase)

Figure 2A:
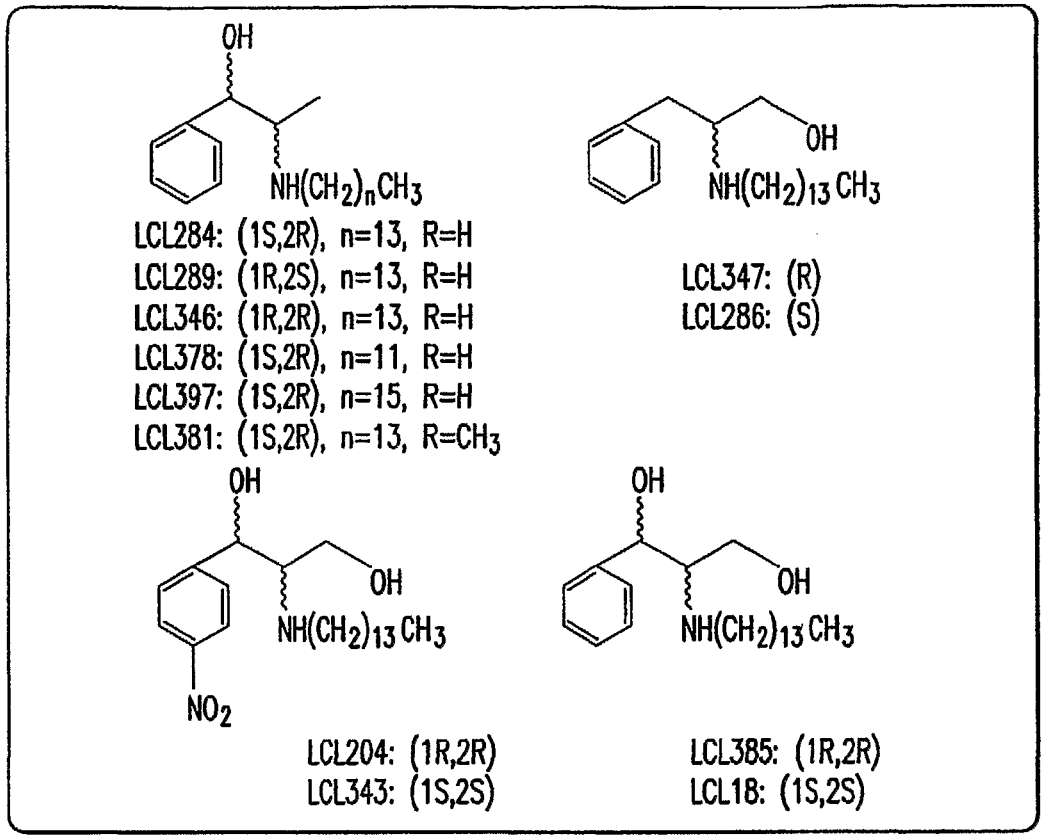
Figure 2B:
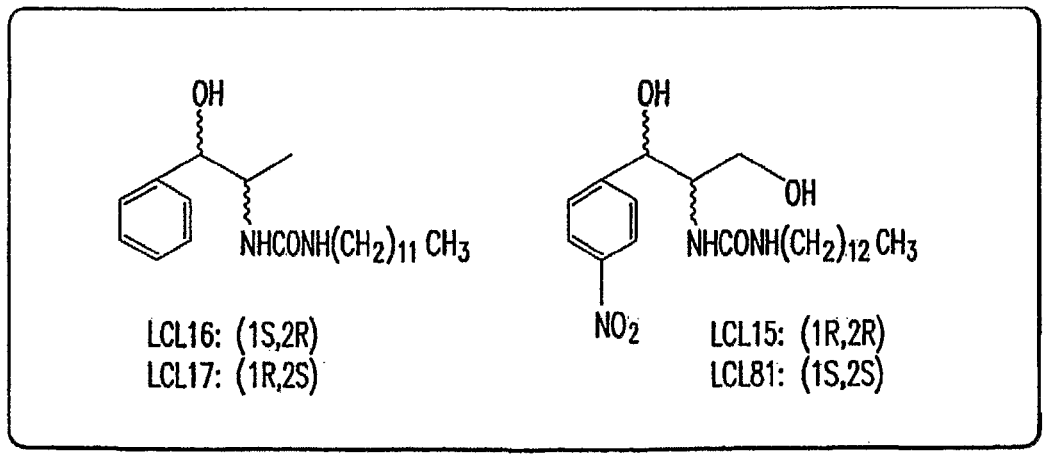

FIGS. 2A-B. Structures of representative ceramide analogs

Figure 2C:
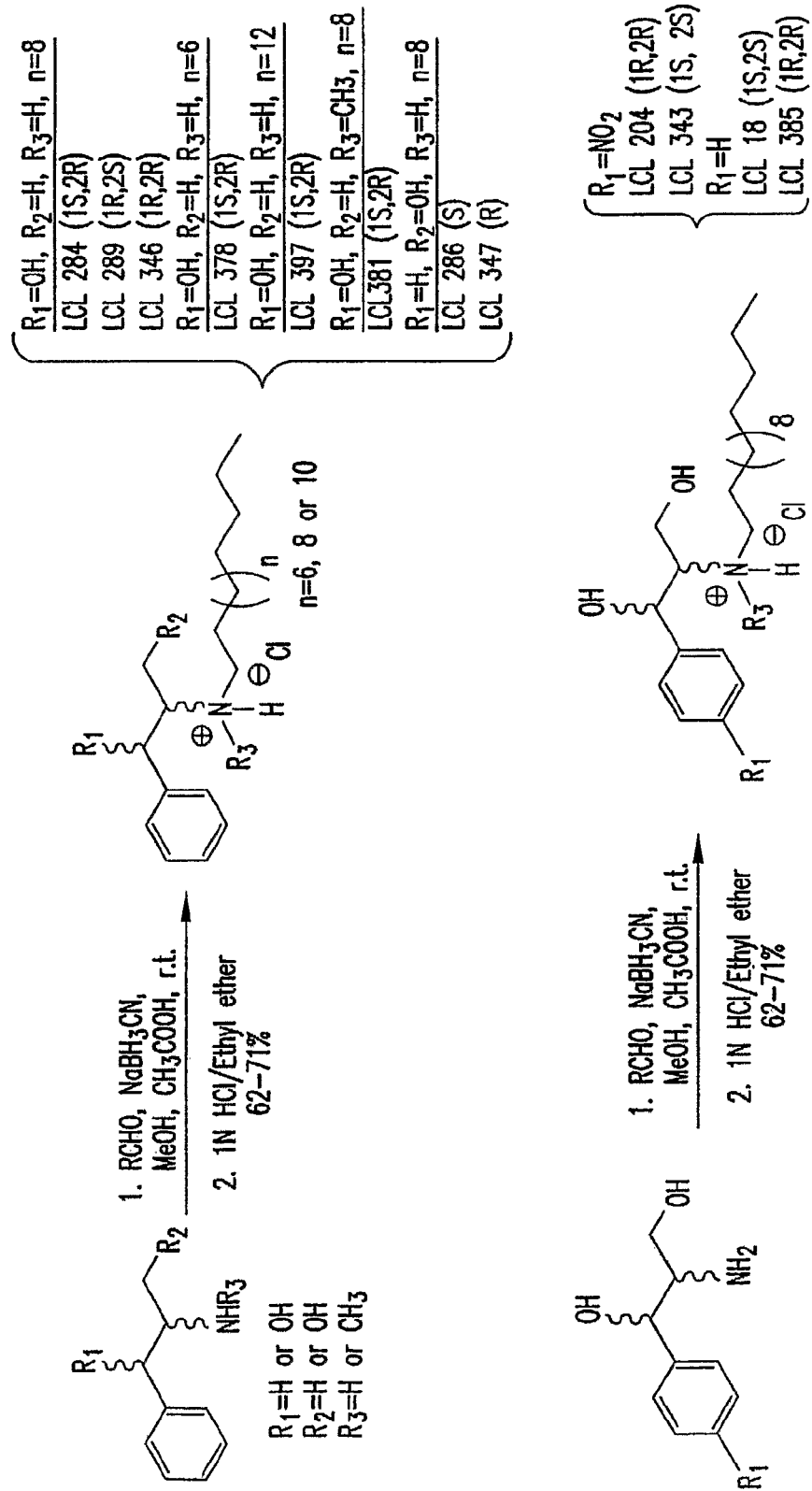

FIG. 2C. Scheme 1: Synthesis of Class A analogs

Figure 2D:
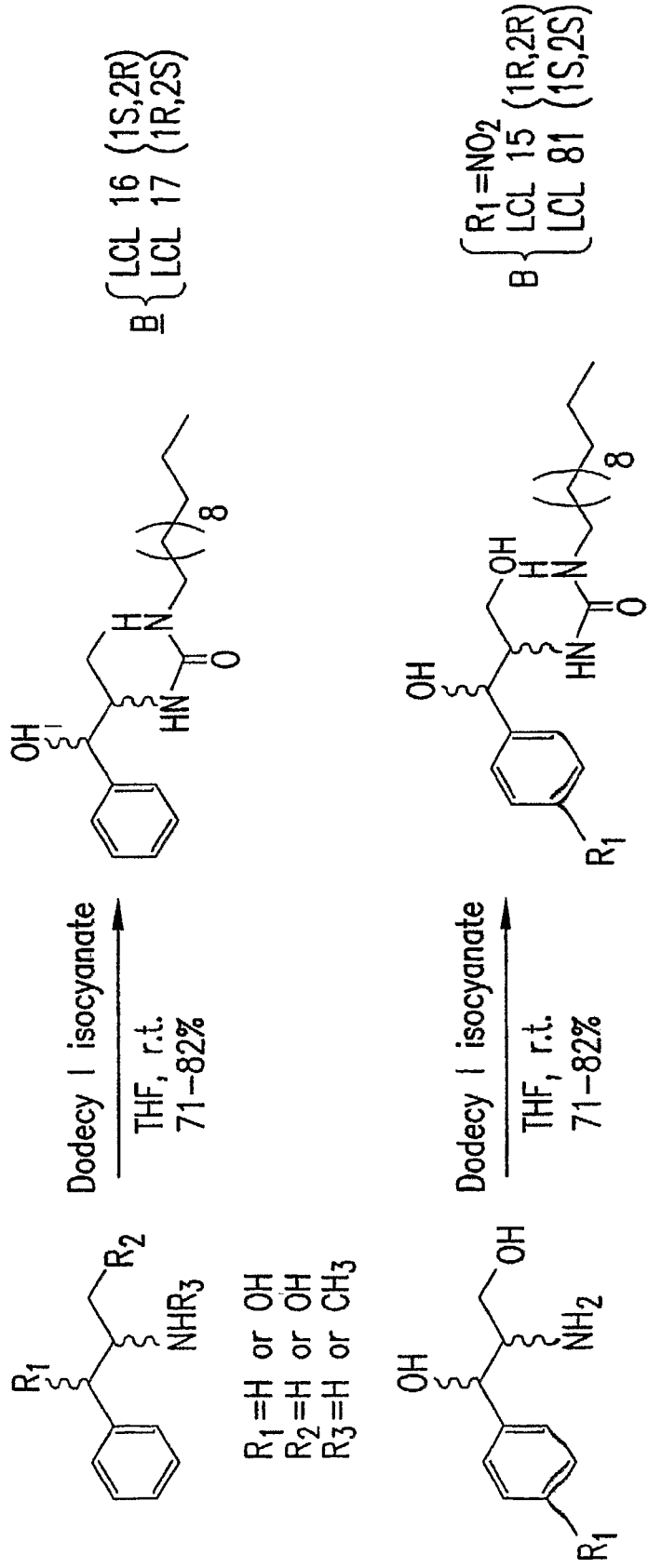

FIG. 2D. Scheme 2: Synthesis of Class B analogs

FIG. 2E. Scheme 3: Synthesis of Class D of Ceramidoids

Figure 3:
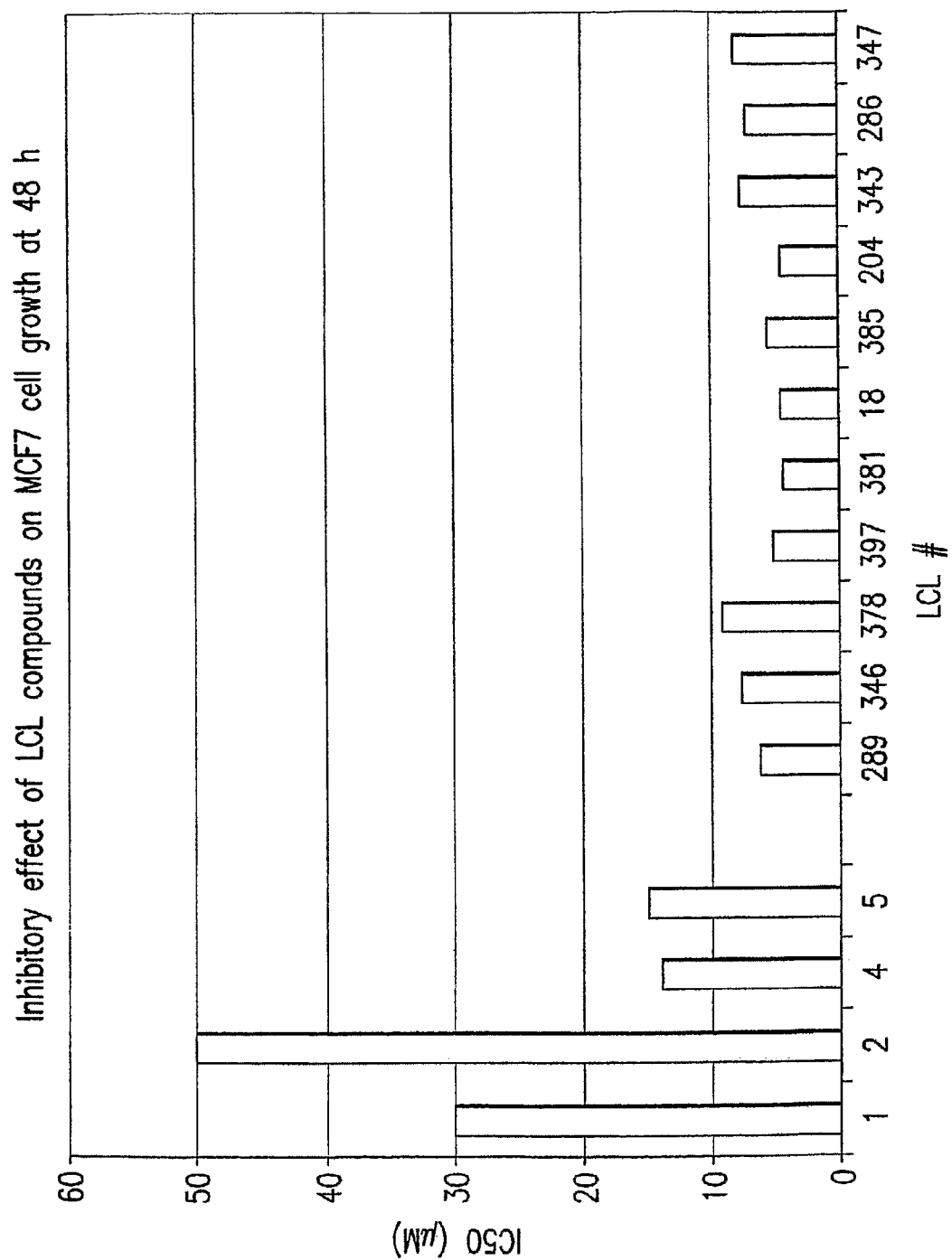

FIG. 3. Inhibitory effect of new ceramide modulators on MCF7 cell growth (48 hours)

Figure 4A:
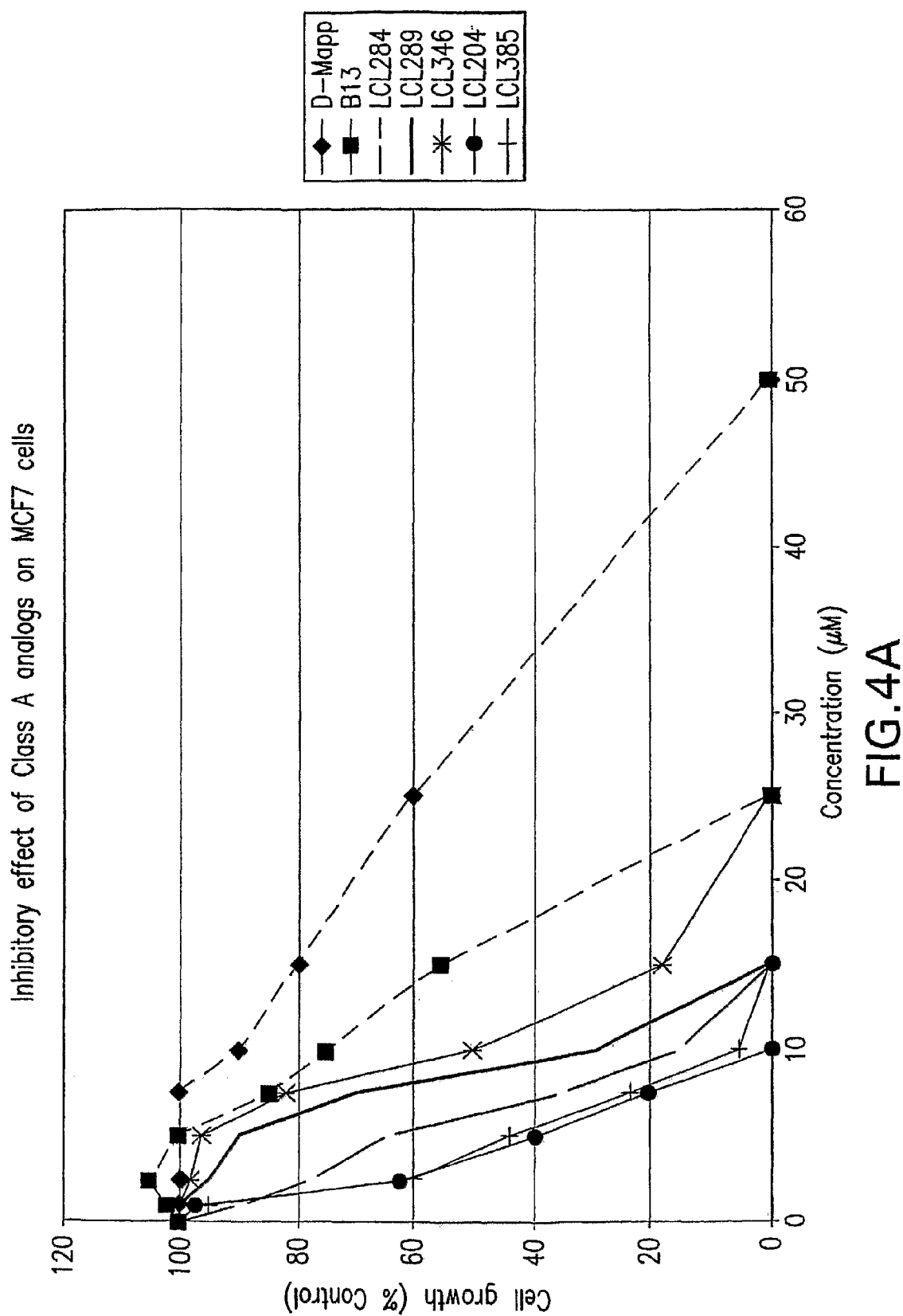

FIG. 4A. Inhibitory effect of Class A analogs on MCF7 cells

Figure 4B:
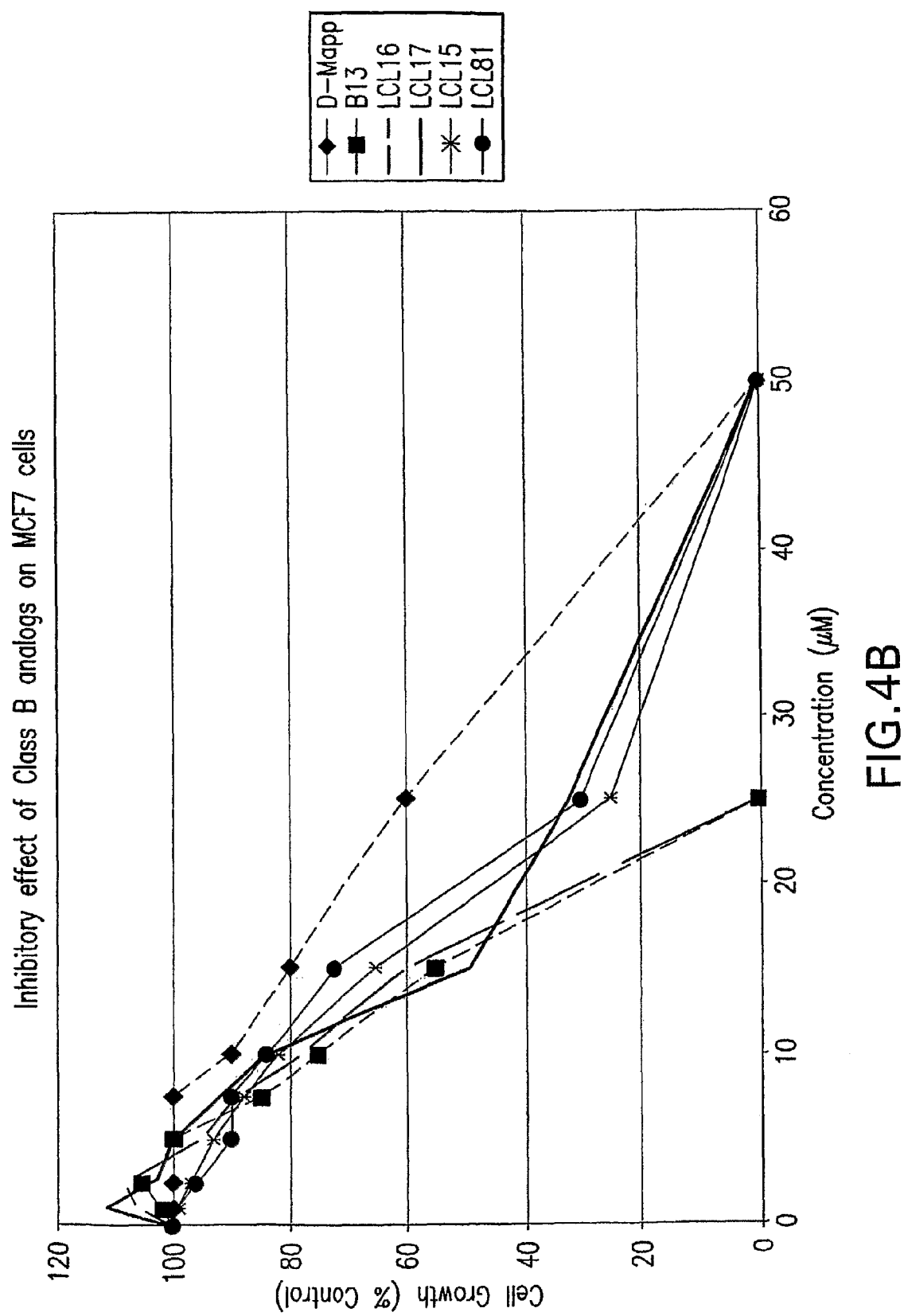

FIG. 4B. Inhibitory effect of Class B analogs on MCF7 cells.

Figure 4C:
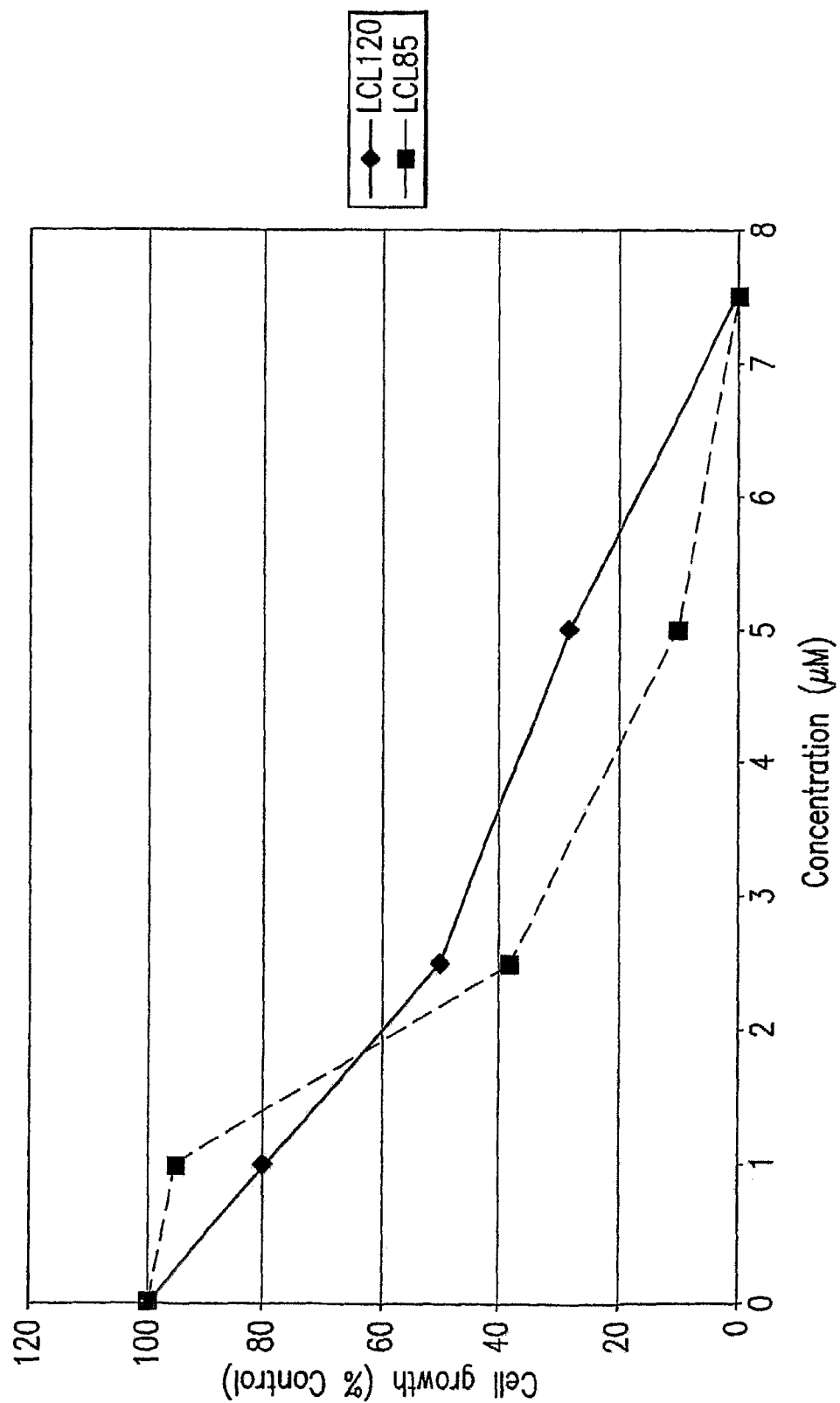

FIG. 4C. Inhibitory effect of LCL 120 and LCL 85 in MCF7 cells at 48 hours.

Figure 5:
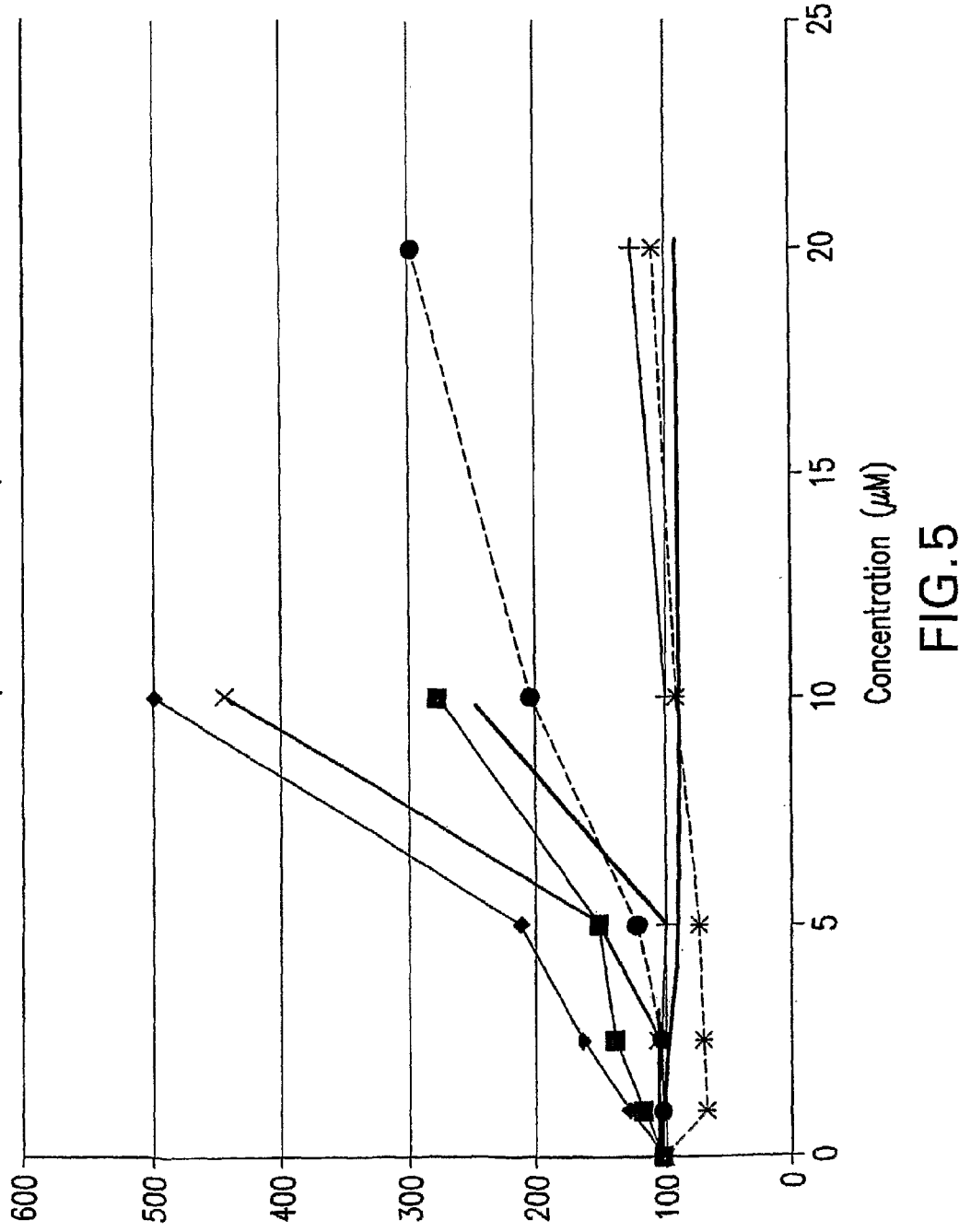

FIG. 5. Effect of representative analogs of endogenous ceramide (24 hours, MCF7 cells)

Figure 6:
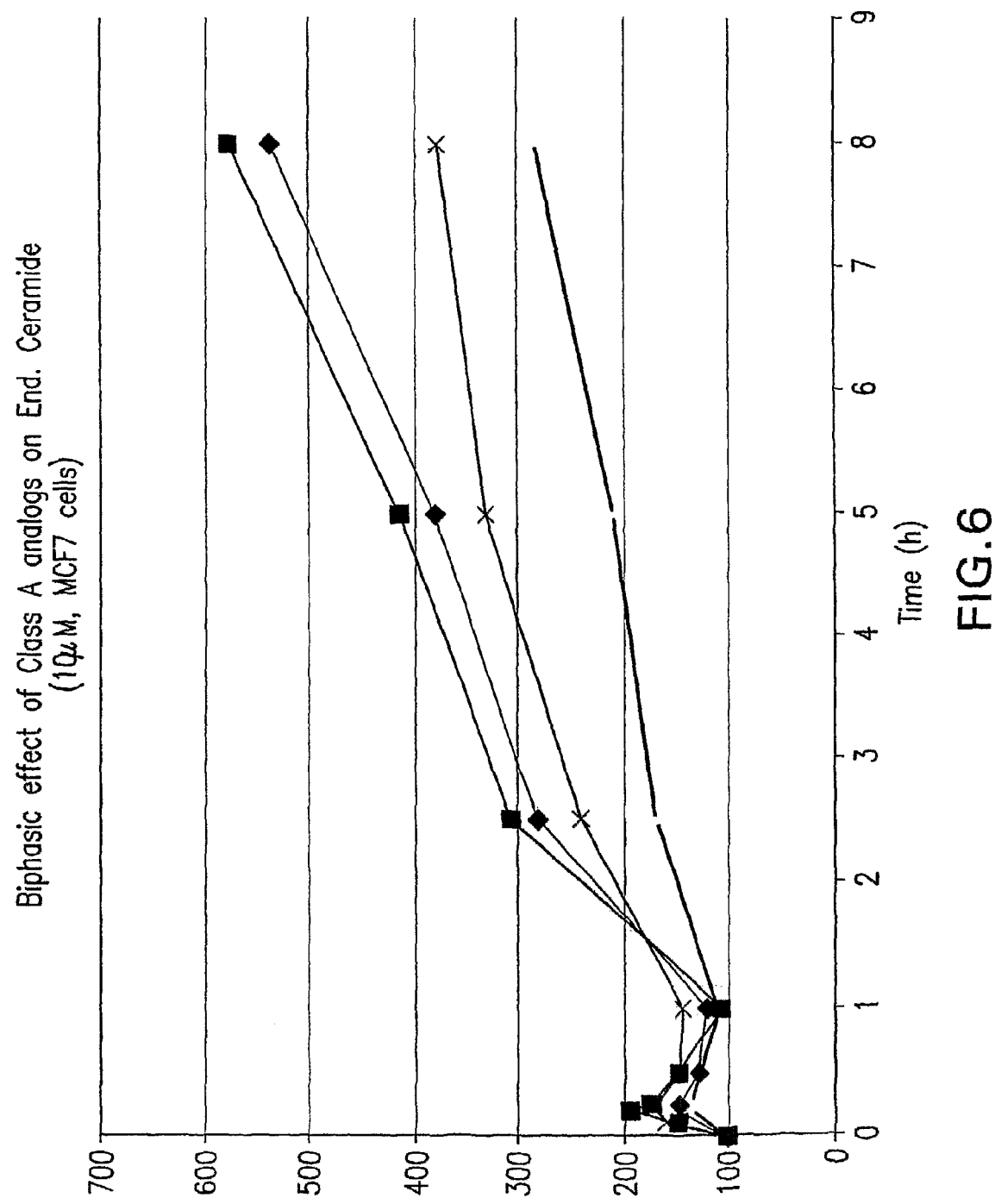

FIG. 6. Biphasic effect of Class A analogs on endogenous ceramide (10 μM, MCF7 cells)

Figure 7:
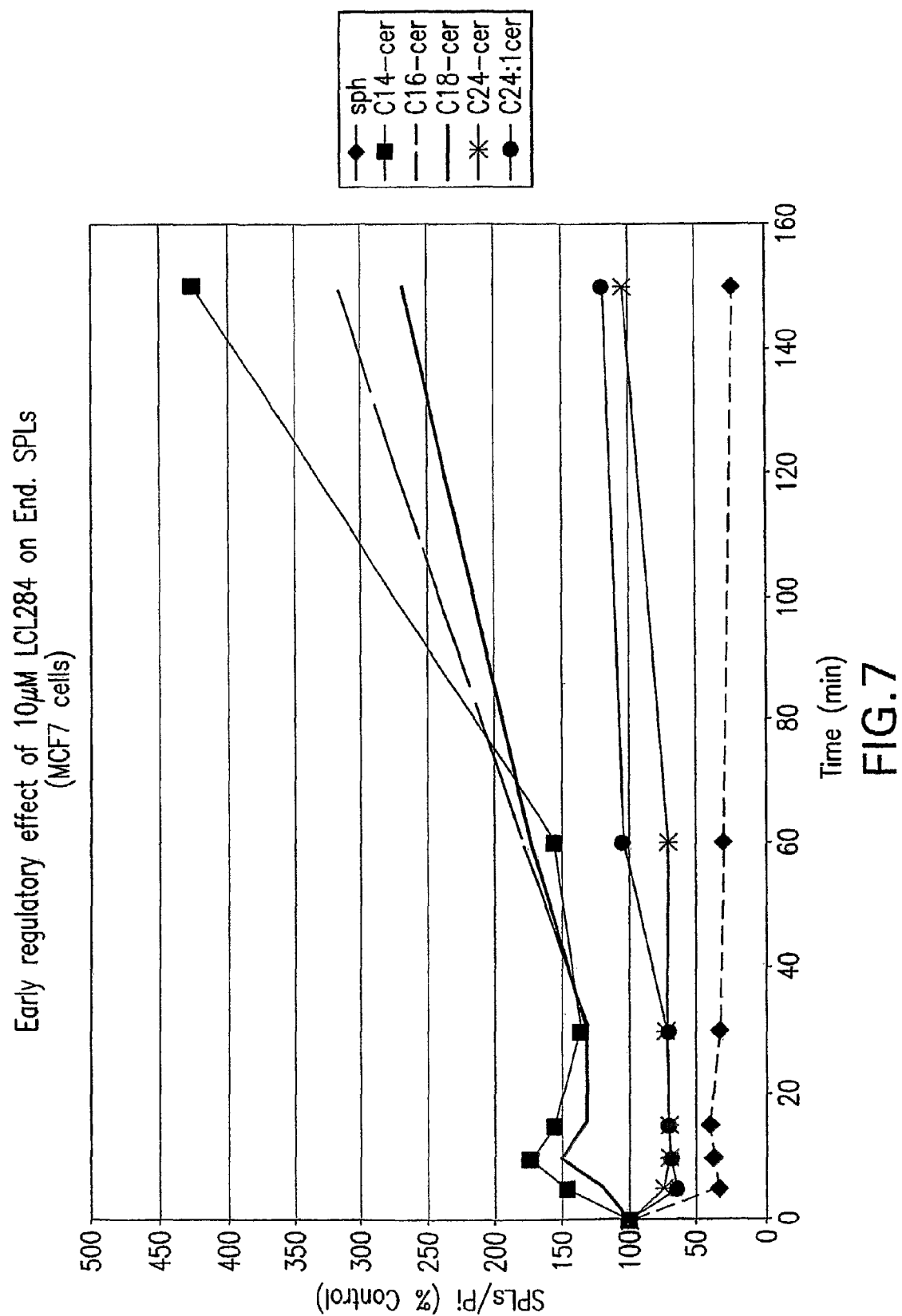

FIG. 7. Early regulatory effect of 10 μM LCL284 on endogenous SPLS (MCF7 cells)

Figure 8:
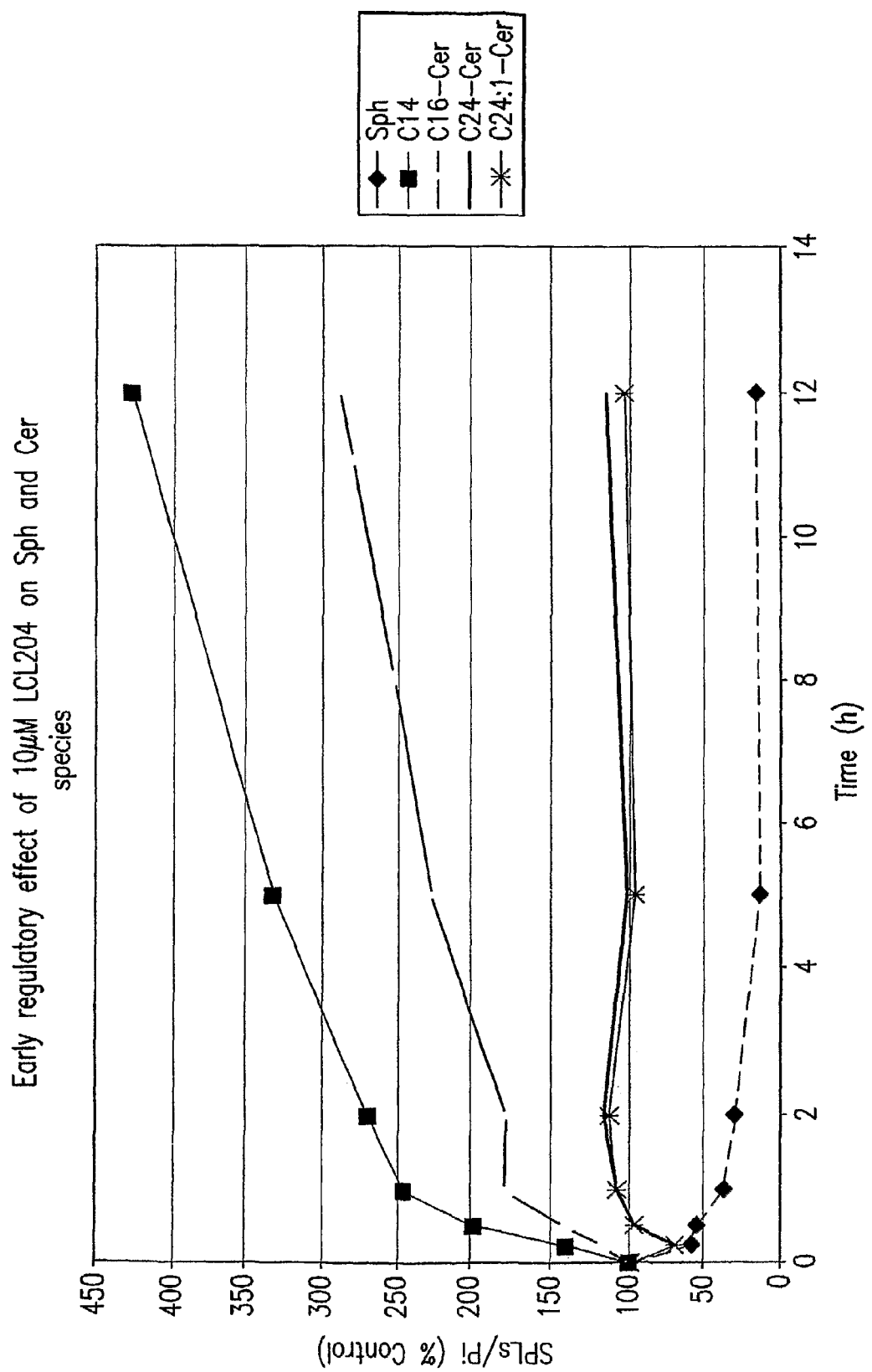

FIG. 8. Early regulatory effect of 10 μM LCL204 on Sph and Cer species

Figure 9:
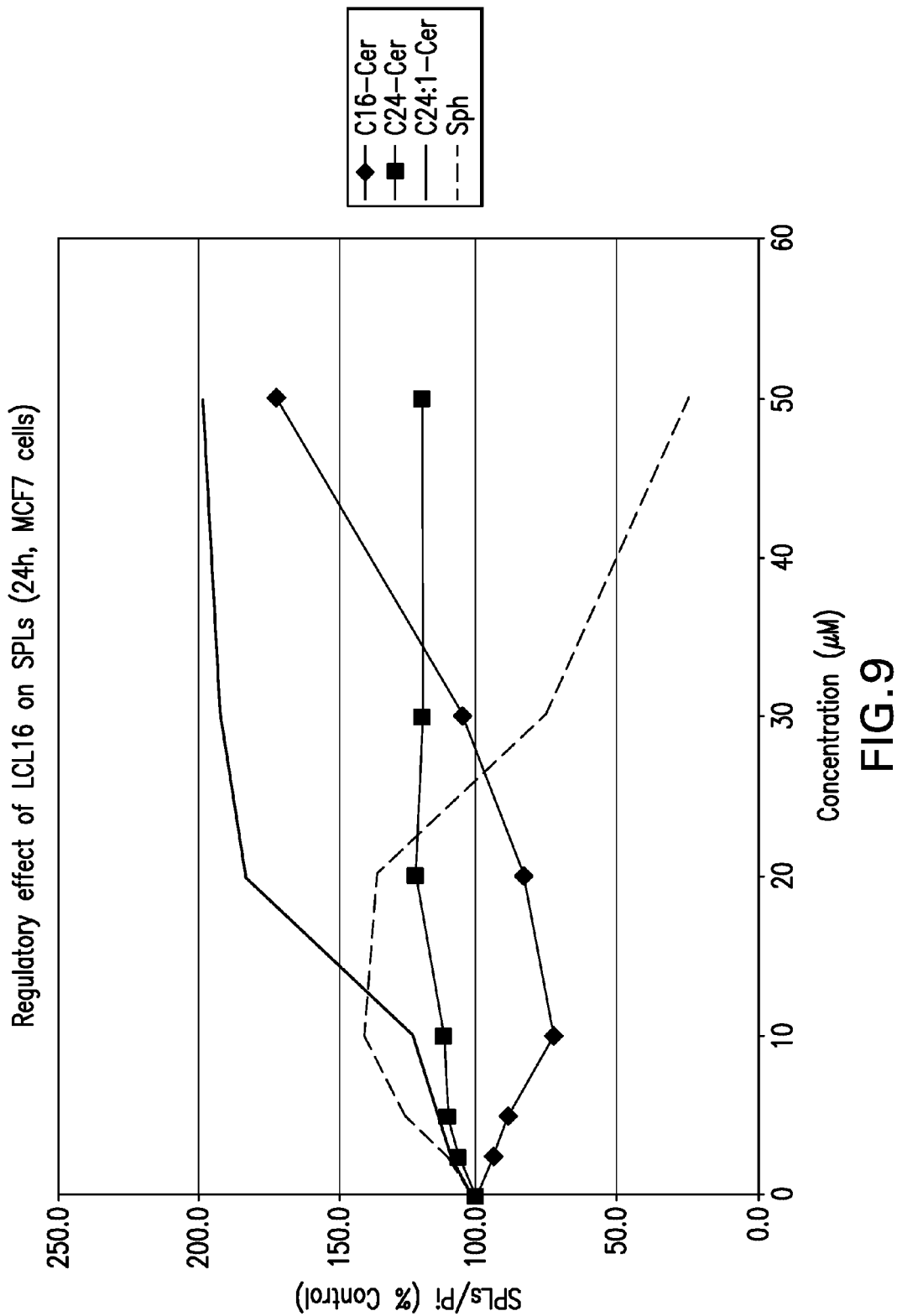

FIG. 9. Regulatory effect of LCL16 on SPLS (24 hours, MCF7 cells)

Figure 10A:
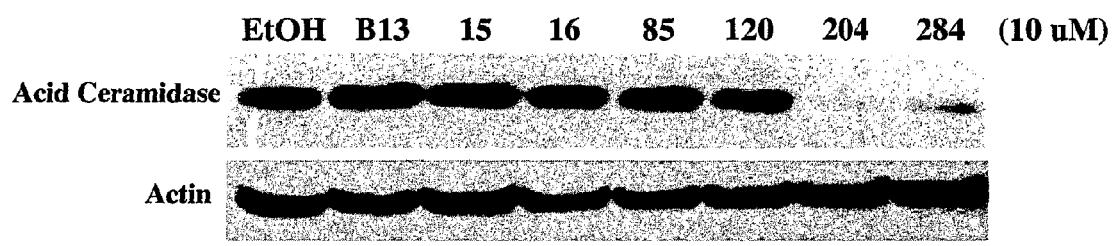
Figure 10B:
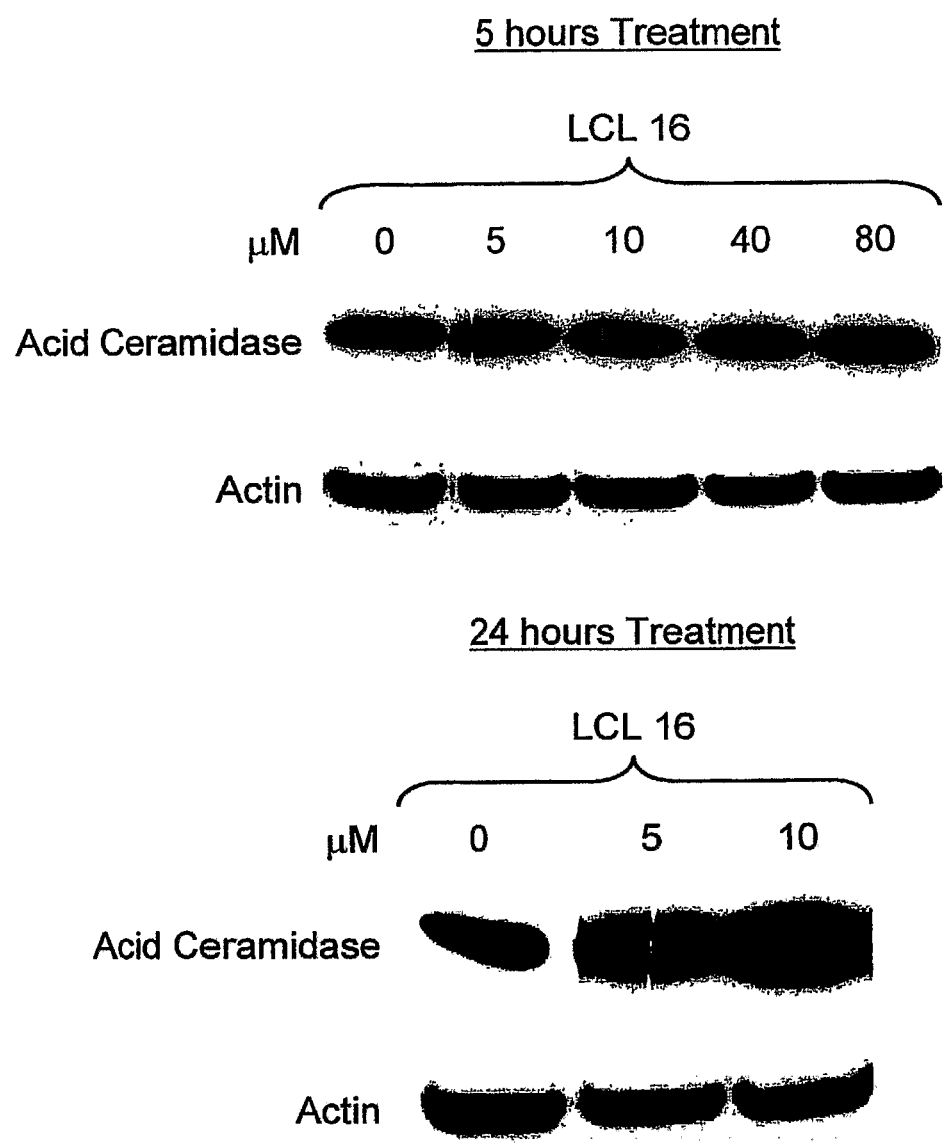

FIG. 10. Effects of different compounds on acid ceramidase protein level in MCF57 cells. A, Western blot of MCF57 cells treated for 5 hours with 10 μM of different compounds (B13, LCL15, LCL16, LCL85, LCL120, LCL204 and LCL284) compared to vehicle (EtOH) treatment. B, Western blots of MCF7 cells treated with LCL16 at indicated concentrations for 5 hours (upper panel) and for 24 hours (lower panel).

Figure 11:
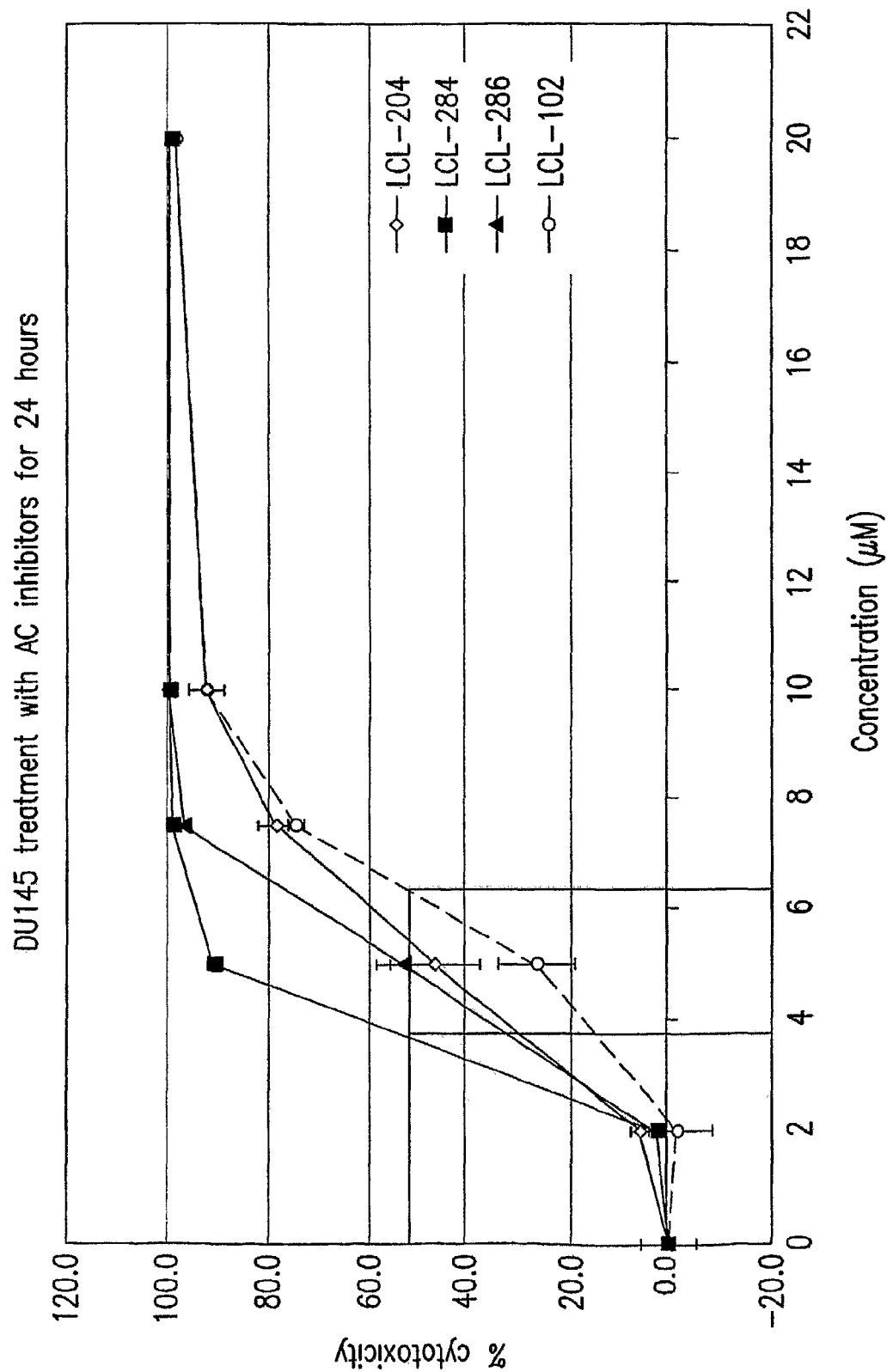

FIG. 11. DU145 treatment with acid ceramidase inhibitors for 24 hours

FIG. 12. DU145 cells 48 hours 2 μM LCL204 then CH-11 or AdGFPFasL treatment

FIG. 13. (A) Animal survival rate in DU145 treatment (B) Net tumor volume in DU145 treatment FIG. 14. LCL204 induces apoptosis in PCa cells. Cell death (A, B) was quantified using MTS cell viability assay and results of each are representative of three independent experiments. A, Five PCa cell lines were treated for 24 hours with LCL204. B, DU145 cells were pre-treated for one hour with vehicle control or zVAD-fmk followed by 24 hours treatment with LCL204; All experiments were performed in triplicate; bars, SD. C, Caspase 3/7 activities in DU145 cells were measured using a fluorometric activity assay after 24 hours treatment with LCL204. D, Mitochondria membrane potential in DU145 cells was measured after LCL204 treatment using JC-1 dye and flow cytometric analysis. A decrease in potential corresponds to a shift in fluorescence from 527 nm to 590 nm. E, Cytochrome c release into the cytosol demonstrated by Western blotting cytosolic extracts for cytochrome c.

FIG. 15. LCL204 regulates ceramide and sphingosine levels in DU145 cells. DU145 and PPC-1 cells were treated for indicated times with LCL204 (2 μM and 10 μM). After treatment cells were harvested as described under Materials and Methods and total ceramide levels were measured using mass spectrometry and plotted according to percent control levels. Results are representative of three independent experiments.

FIG. 16. LCL204 induces degradation of AC and inhibits activity of ASmase. A, Western blots of DU145 cells treated for 12 hours with indicated concentrations of LCL204 compared to vehicle (V) treatment (upper panel) or cells treated with 5 μM LCL204 for indicated time points (lower panel). B, RT-PCR determined that mRNA levels of AC in DU145 cells were not affected by treatment with LCL204 (10 μM) for indicated times. Rig/S15 primers were used as an internal control. C, DU145 cells were pre-treated for one hour with vehicle control, zVAD-fmk (50 μM), MG132 (100 nM), CA074Me (10 μM), or pepstatin A (1 μg/mL) followed by LCL204 (10 μM) for 6 hours and lysates analyzed by Western blot. D, Upper: ASMase activity in DU145 cells following 10 μM LCL204 treatment for indicated times; Lower: DU145 cells were pre-treated for one hour with inhibitors as in (C) before addition of 10 μM LCL204 for two hours. Results are representative of three independent experiments.

FIG. 17. LCL204 induces lysosomal instability and membrane permeabilization. Lysosomal pH was quantified inversely using LysoTracker Red staining and flow cytometric analysis (A, B, C). A, DU145 cells were treated for one hour with vehicle control, LCL204 (10 μM), B13 (20 μM), $C_6$-ceramide (30 μM), sphingosine (40 μM), or $NH_4Cl$ (10 mM). B, DU145 cells treated with 10 μM LCL204 for indicated time points. C, DU145 cells treated for one hour with indicated concentrations of LCL204. Data shown are representative results from at least two independent experiments. D and E, DU145 cells were lysed and subcellular fractionation performed as described under Materials and Methods Cells treated with 10 μM LCL204 for indicated times and cathepsin B translocation was analyzed by Western blot (D) or enzyme activity assay (E); bars, SD.

FIG. 18. LCL204 induces pro-apoptotic Bcl-2 and p53 family members. A, DU145 cells were treated for 12 hours with vehicle (V) control or indicated concentration of LCL204 and lysates were analyzed by Western blot. B, DU145 or PC-3 cells were treated for indicated times with LCL204 (10 μM) and whole cell lysates were analyzed by Western blot. Results are representative of three independent experiments. C, Visualization of LCL204-induced Bak foci using confocal microscopy. DU145 cells transfected with YFP-mito were treated with LCL205 (15 μM) as described under materials and methods. Bak was immunostained red, while mitochondria showed green fluorescence. Overlay of the two is represented as yellow; inset, zoom of Bak foci. D, DU145, PC-3 or LNCaP cells were treated for the indicated times with LCL204 (10 μM) and whole cell lysates were analyzed by Western blot. Results are representative of three independent experiments.

FIG. 19. LCL204 activates Stress-Activated Protein Kinases. A, DU145 (i), PC-3 (ii), PPC-1/pcDNA3 (iii), or PPC-1/TAM67 (iv) cells were treated for indicated times with LCL204 (DU145 and PC-3: 10 μM, PPC-1 transfectants: 7.5 μM). Whole cell lysates were analyzed by Western blot for phosphorylated JNK and p38 MAPK. Antibodies for total JNK or total p38 MAPK were used as internal controls. B, PPC-1/pcDNA3 or PPC-1/TAM67 cells were treated for the indicated times with 7.5 μM LCL204 in the absence (i, ii) or presence (iii) of 40 μM SP600125 and whole cell lysates were analyzed by Western blot. Results are representative from two independent experiments. C, PPC-1/pcDNA3 or PPC-1/TAM67 cells were treated with 7.5 μM LCL204 for 5 hours in the absence or presence of SB-203580 (20 μM) and lysates analyzed by Western blot. D (i), PPC-1/pcDNA3 and PPC-1/TAM67 cells were treated with indicated concentrations of LCL204 for 12 hours; (ii) PPC-1/pcDNA3 cells were treated with the indicated concentrations of LCL204 for 8 hours in the absence (squares) or presence of 20 μM SB-203580 (circles), 40 μM SP600125 (triangles) or a combination of SB-203580 and SP600125 at the same respective concentrations (diamonds). Cell viability was determined by MTS assay; bars, SD.

Figure 20:
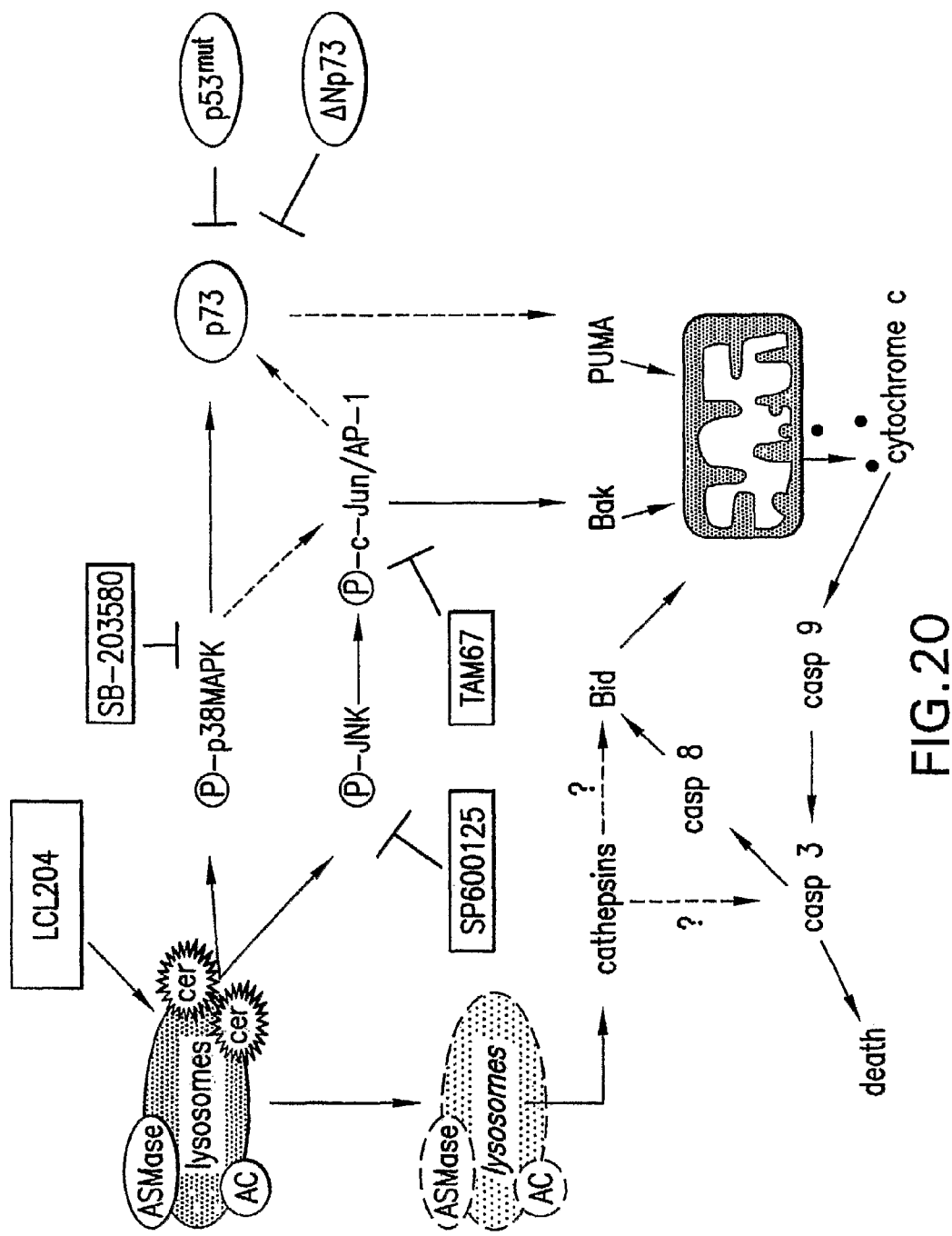

FIG. 20. Summary of proposed molecular events induced by LCL204.

5. DETAILED DESCRIPTION OF THE INVENTION

The present invention relates to compounds of formula (I) ("ceramide analogs"). The present invention also includes methods of making, and methods of using such ceramide analogs, particularly for treatment and/or prevention of diseases related to cell overproliferation and/or dysfunctional sphingolipid signal transduction.

The present invention also encompasses methods that comprise administering a ceramide analog in combination with another treatment modality that acts by triggering of apoptosis. The invention is based, in part, on the recognition that ceramide analogs of the invention can enhance or improve the therapeutic benefit of apoptosis-signaling ligands in cancer treatment. The use of these compounds as pharmaceutical compounds are described in details in section 5.3. Uses of these compounds in combination with other therapeutic agents are also contemplated, and are described in details in section 5.5.

Ceramides are known to regulate anti-proliferative responses, such as apoptosis, growth arrest, differentiation and senescence in various human cancer cell lines. Many important biological targets and events related to ceramide actions in cells have been identified, namely, activation of phosphatases, kinases and caspases; inhibition of the telomerase enzyme complex; induction of the transmembrane signaling pathways and release of cytochrome c from mitochondria. The shortcomings with the use of ceramides as perspective anticancer agents are very low water solubility, low cellular uptake, uncontrolled delivery, release and intracellular targeting. Ceramidase is an enzyme which hydrolyze ceramide and decrease its level in cells. Inhibition of ceramidase will increase level of endogenous ceramide and inhibitors of this enzyme are exploited as candidates for drug discovery.

The family of ceramidases includes acid, neutral, and alkaline species (Koch et al., 1996, *Journal of Biological Chemistry* 271, 33110-5; Mao et al., 2001, *Journal of Biological Chemistry* 276, 26577-88; El Bawab et al., 1999, *Journal of Biological Chemistry* 274, 27948-55). Human acid ceramidase, maps to 8p22, which is frequently altered in PCa. This enzyme catalyses the hydrolysis of ceramide to sphingosine and free fatty acids, the overall effect of which is downregulation of ceramide signaling (i.e., decreased apoptosis) and increased pools of sphingosine, which can be phosphorylated by sphingosine kinase to generate sphingosine 1 phosphate (S1P). S1P interacts with the endothelial differentiation gene family (Edg/S1P receptors) to promote endothelial cell migration and angiogenesis. Thus, a cell or tumor over-expressing ceramidase generates an antiapoptotic phenotype and a potential increase in angiogenesis in its microenvironment.

The PCa cell lines DU145, PC3 and LNCaP all show elevated levels of ceramidase mRNA by Northern blotting. Prostate tumors, obtained from radical prostatectomies, when analyzed for acid ceramidase expression by a competitive PCR approach demonstrated that 41.6% had increased levels of acid ceramidase mRNA, 55.5% had no change and 2.7% had a decrease. Thus, in prostate cancer a significant fraction of tumors has the potential to assume an antiapoptotic phenotype.

In most cancer cells including prostate cancer (PCa), at a biochemical level, ceramide causes activation of caspases, DNA fragmentation and other characteristics and hallmarks of apoptosis, induction of the stress-activated protein kinases (SAPK/JNK), inhibition of phospholipase D, dephosphorylation and inactivation of protein kinase C (PKC), enhanced release of mitochondrial reactive oxygen species, release of cytochrome c, and activation of PP1, which dephosphorylates SR proteins leading to a more pro-apoptotic phenotype.

Mechanistically, a coordinated picture of cell growth regulation involving ceramide and other key regulators of cell cycle progression and apoptosis is emerging. Thus, the formation of ceramide in response to TNF and other, but not all, inducers requires activation of upstream caspases (e.g., Caspase 8) which are inhibited by YVAD and by Crm A. However, inhibitors of downstream caspases fail to prevent ceramide formation and yet ceramide activates downstream caspases (e.g., Caspase 3) but not upstream Caspases. Moreover, the ability of ceramide to induce apoptosis is blocked by inhibitors of the executioner caspases but not effector caspases placing ceramide formation between the two sets of enzymes. Also, studies with Bcl-2 show that Bcl-2 is downstream of ceramide in the same pathway. Thus, ceramide regulates phosphorylation of Bcl-2 and the action of ceramide on cell death is inhibited by Bcl-2 over expression.

In all these actions, short chain ceramides exhibit a level of potency consistent with levels of endogenous ceramides. The action of ceramide analogs exhibits significant specificity. For, example, the closely related neutral lipid, DAG, not only does not mimic the action of ceramide, but more often antagonizes it. Studies by the inventors showed that dihydroceramide, which is the metabolic precursor to ceramide and differs from it only in that it lacks the 4-5 trans double bond, exhibits no activity in these cellular studies, although it shows similar levels of uptake (Bielawska et al., 1993, *Journal of Biological Chemistry* 268, 26226-32; Bielawska et al., 1992, *Journal of Biological Chemistry* 267, 18493-7).

In contrast, short chain ceramides are poor effectors of other key actions associated with TNF and other inducers of ceramide formation. Notably, ceramide is not active in inducing NF-κB, a transcription factor that plays a role in the inflammatory and anti-apoptotic function of TNF. Also, ceramide is a poor activator of erk members of the MAP kinase family, especially when compared with sphingosine and sphingosine-1-phosphate. This restricted action of short chain ceramides to a subset of biochemical targets in cytokine responses provides further impetus to the emerging hypothesis of a more specific function for ceramide in the regulation of apoptosis in cancer.

The inventors recognized the multiple lines of evidence that point to a role for ceramide in mediating Fas-induced apoptosis. First, ceramide generation has been demonstrated to be an integral part of Fas-induced apoptosis (Cremesti et al., 2001, *Journal of Biological Chemistry* 276, 23954-61). Second, Fas activation has been shown to activate acid sphingomyelinase, which was demonstrated to be involved in propagation of Fas-generated apoptotic signaling (Raisova et al., 2000, *FEBS Letters* 473, 27-32). Third, Fas-induced ceramide formation acts in conjunction with caspase activation and is not a consequence of apoptosis (Tepper et al., 1997, *Journal of Biological Chemistry* 272, 24308-12). Fourth, Fas-resistant cells demonstrate insignificant changes in ceramide levels yet have normal receptor expression and intact downstream signaling (Tepper et al., 1995, *Proceedings of the National Academy of Sciences of the United States of America* 92, 8443-7). Fifth, a role for de novo ceramide synthesis has also been established in Fas-induced apoptosis (Chalfant et al., 2001, *Journal of Biological Chemistry* 276, 44848-55) suggesting two possible "pools" of ceramide can affect Fas signal transduction. Sixth, acid sphingomyelinase null hepatocytes are insensitive to J02-induced capping but are sensitized with a 25 nM dose of C16-ceramide. Accordingly, the present invention exploits the role of ceramide in mediating Fas-induced apoptosis.

The present invention also addresses one of the serious issues in current gene therapy protocols, namely the lack of the physician's ability to effectively deliver gene therapy molecules to sufficient numbers of cells in a cancer to result in a cure. This problem is widespread throughout the discipline as attested by numerous publications in the current literature. The basic problem is that in trying to treat a cancer it is necessary to deliver a therapeutic gene to the bulk of the cells in the cancer. At the present time, this is not possible with the current vectors or lipsomes. The present invention provides a method of surmounting this problem by combining a gene therapy approach, in which approximately 25% of the cells have the vector delivered to them, with small molecule therapy that alters the anti-apoptotic phenotype of the cancer cells to a pro-apoptotic form. This creates a situation within the tumor that allows for bystander activity to manifest itself [Hyer M L, Sudarshan S, Schwartz D A, Hannun Y A, Dong J-Y, Norris J S. Quantification and characterization of the bystander effect in prostate cancer cells following adenovirus mediated FasL expression, Cancer Gene Therapy, 10(4):330-339, 2003]. The bystander effect is operative when the number of cells undergoing apoptosis in the tumor bed is greater than the number of cells transduced. For example, bystander activity is associated with the cell killing mechanism of FasL virus when infected cells undergo apoptosis and produce apoptotic vesicles that continues to express FasL on their surface. The apoptotic vesicles that are formed by this procedure kill adjacent cells that are susceptible to Fas signaling. These same apoptotic vesicles, as well as the novel ceramide modulators, can destroy the blood flow to the tumor by destroying blood vessel endothelium. This restricts blood flow to the tumor and further accelerates its demise. It has been shown that some tumors are resistant to signaling by FasL and thus the present invention provides a method for sensitizing these cells with small molecules to allow the bystander effects to be manifested on a much broader scale.

In particular, the invention encompasses methods of treatment and compositions that provide a better therapeutic profile than that of Fas ligand gene therapy alone. The gene therapy approach encompasses methods of killing a Fas+ tumor cell comprising introducing into a second tumor cell a nucleic acid encoding a Fas ligand (FasL), whereby the second tumor cell expresses the nucleic acid thereby producing FasL, and whereby interaction of the Fas+ tumor cell with the second tumor cell expressing FasL causes the Fas+ tumor cell to undergo apoptosis, thereby killing the Fas+ tumor cell. Preferably, the methods of the invention comprise administering orthotopically an adenoviral vector that delivers a nucleic acid encoding a Fas ligand, and systemic administration of ceramide analogs of the invention that perturb sphingolipid metabolism, resulting in much better efficacy.

Although not necessarily directly causative for prostate cancer development, acid ceramidase elevation in 41% of human tumors (60% of Gleeson grade 7 and only 38% of grade 6 tumors) would suggest that its expression provides a selective advantage for tumor growth. The mechanism is likely manifested in two ways. First, reduced levels of ceramide have an anti-apoptotic effect and downregulation of apoptosis is clearly a hallmark of some cancer, including the prostate. Second, S1P production, via increased sphingosine kinase, has an angiogenic and growth effect as well as promoting endothelial cell migration in the prostate. The inventors provide, that by inhibiting acid ceramidase activity, prostate cancer models become more sensitive to FasL gene therapy because AdGFPFasL elevates ceramide levels via de novo (myriocin-dependent) synthesis in all prostate cancer cell lines tested. In Section 7, one embodiment of the invention is demonstrated with acid ceramidase inhibitors (LCL102 or LCL204) at subtoxic doses which increased the ability of AdGFPFasL to kill tumor cells in vitro by as much as ten-fold.

5.1 Ceramide Analogs

In one embodiment, the invention relates to a compound of formula (I) and pharmaceutically acceptable salts thereof, wherein:

$R_1$ is —H, —OH, —SH, —NH$_2$, —Cl, —Br, —I, —C(O)OH, —C(O)NH$_2$, —NH(C=NH)NH$_2$, —NH(R$_2$), or a —N-heterocycle having from 5 to 6 atoms in the ring;

$R_2$ is —H or —(C$_1$-C$_6$)alkyl;

$R_3$ is -phenyl; five-membered monocyclic heterocycle; six-membered monocyclic heterocycle; five- and five-membered bicyclic heterocycle; six- and six-membered bicyclic heterocycle; five- and six-membered bicyclic heterocycle; five-, five-, and five-membered tricylic heterocycle; six-, six-, and six membered tricylic heterocycle; five-, five-, and six-membered tricylic heterocycle; five-, six-, and six-membered tricylic heterocycle; six-, five-, and six-membered tricylic heterocycle; five-, six-, and five-membered tricylic heterocycle; each of the foregoing being optionally substituted with one or more —R$_5$;

$R_4$ is —H, —(C$_1$-C$_6$)alkyl, —CH$_2$(OH), —SH, —NH$_2$, —CH$_2$Cl, —CH$_2$Br, —CH$_2$I, —C(O)OH, or C(O)NH$_2$;

$R_5$ is —(C$_1$-C$_6$)alkyl, —F, —Cl, —Br, —I, —NH(R$_{2a}$), —NO$_2$, or an amide of formula

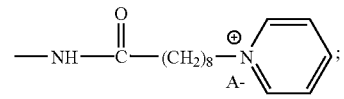

$R_{2a}$ is —H or —(C$_1$-C$_6$)alkyl; or

X is —CH$_2$—, —CH((C$_1$-C$_6$)alkyl)-, —C(O)—, or —C(S)-;

Y is —C(O)—, —N(H)—, —CH$_2$—, or —O—;

A is —CH$_2$—, —CHOH—;

a is 0 or 1;

b is 0 or 1;

n is an integer from 2 to 22; and

A$^-$ is a pharmaceutically acceptable counter-anion.

In one embodiment, $R_1$ is —H, —OH, —Cl, —Br, or —I.

In another embodiment, $R_1$ is —H.

As used herein, the phrase "—N-heterocycle having from 5 to 6 atoms in the ring" means an aliphatic, aromatic, or unsaturated —N-heterocyclic ring containing at least one N-atom. It will be understood that the —N-heterocycle having from 5 to 6 atoms in the ring can also contain additional heteroatoms such as, e.g., N, O, S, B, P, Si, and the like.

Non-limiting examples of useful —N-heterocycle having from 5 to 6 atoms in the ring include:

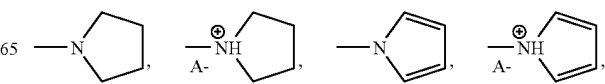

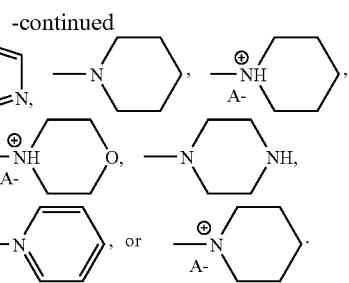

Non-limiting examples of pharmaceutically acceptable counter-anions include halo (e.g., $F^-$, $Cl^-$, $Br^-$, $I^-$); carboxylates such as acetate or propanoate; phosphates such as $PO_4^{3-}$, $PO_4H_2^-$ and $PO_4H^{2-}$; $OH^-$, and the like.

In one embodiment, $A^-$ is $F^-$, $Cl^-$, $Br^-$ or $I^-$.

In one embodiment, $R_1$ is -1-pyridine.

In another embodiment, $R_1$ is -1-pyridinium.

In another embodiment, $R_2$ is —H.

In another embodiment, $R_2$ is —($C_1$-$C_6$)alkyl.

In another embodiment, $R_2$ is —$CH_3$.

In one embodiment, $R_3$ is -phenyl, optionally substituted with one or more —$R_5$.

In other embodiment, $R_3$ is -4-nitro-phenyl.

In another embodiment, $R_3$ is -4-(9-pyridinium)nononamide)phenyl having the structure:

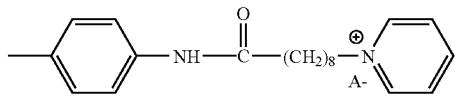

In one embodiment, $R_4$ is —H, —($C_1$-$C_6$)alkyl, or —$CH_2$(OH).

In another embodiment, $R_4$ is —H.

In another embodiment, $R_4$ is —($C_1$-$C_6$)alkyl.

In another embodiment, $R_4$ is —$CH_3$.

In another embodiment, $R_4$ is —$CH_2$(OH).

In another embodiment, X is —$CH_2$—.

In one embodiment, a is 0.

In another embodiment, a is 1.

In another embodiment, a is 1; and Y is —C(O)—, or —N(H)—.

In another embodiment, a is 1; and Y is —C(O)—

In another embodiment, a is 1; and Y is —N(H)—.

In one embodiment, b is 0.

In another embodiment, b is 1.

In another embodiment, b is 1 and A is —$CH_2$—.

In one embodiment, a is 1, b is 1, Y is —N(H)— and A is —$CH_2$—.

In another embodiment, $R_3$ is -phenyl, a is 1, b is 1, Y is —N(H)— and Z is —C(O)—.

In another embodiment, $R_1$ is —H, $R_3$ is -phenyl, $R_4$ is —$CH_3$, a is 1, b is 1, Y is —N(H)— and Z is —C(O)—.

In another embodiment, $R_1$ is —H, $R_2$ is —H, $R_3$ is -phenyl, $R_4$ is —$CH_3$, a is 1, b is 1, Y is —N(H)— and A is —$CH_2$—, —(R)-CH(OH)—, n is 12, and carbon atom 2 of the compound of formula I is the (R)-isomer.

In another embodiment, $R_1$ is —H, $R_2$ is —H, $R_3$ is -phenyl, $R_4$ is —$CH_3$, a is 1, b is 1, Y is —N(H)—, A is —$CH_2$—, X is —(S)-CH(OH)—, n is 12, and carbon atom 2 of the compound of formula I is the (R)-isomer.

In another embodiment, $R_1$ is —H, $R_2$ is —H, $R_3$ is -phenyl, $R_4$ is —$CH_3$, a is 1, b is 1, Y is —N(H)—, A is —$CH_2$—, X is —(R)-CH(OH)—, n is 12, and carbon atom 2 of the compound of formula I is the (S)-isomer.

In another embodiment, $R_1$ is —H, $R_2$ is —H, $R_3$ is -phenyl, $R_4$ is —H, a is 1, b is 1, Y is —N(H)—, A is —$CH_2$—, X is —(S)-CH(OH)—, n is 12, and carbon atom 2 of the compound of formula I is the (S)-isomer.

In one embodiment, $R_3$ is -4-nitro-phenyl, a is 1, b is 1, Y is —N(H)— and Z is —C(O)—.

In another embodiment, $R_1$ is —H, $R_2$ is —H, $R_3$ is -4-nitro-phenyl, $R_4$ is $CH_2$(OH), a is 1, b is 1, Y is —N(H)— and Z is —C(O)—.

In another embodiment, $R_1$ is —H, $R_2$ is —H, $R_3$ is -4-nitro-phenyl, $R_4$ is —$CH_2$(OH), a is 1, b is 1, Y is —N(H)—, Z is —C(O)—, X is —(R)-CH(OH)—, n is 13, and carbon atom 2 of the compound of formula I is the (R)-isomer In another embodiment, $R_1$ is —H, $R_2$ is —H, $R_3$ is -4-nitro-phenyl, $R_4$ is —$CH_2$(OH), a is 1, b is 1, Y is —N(H)—, Z is —C(O)—, X is —(S)-CH(OH)—, n is 13, and carbon atom 2 of the compound of formula I is the (R)-isomer.

In another embodiment, $R_1$ is —H, $R_2$ is —H, $R_3$ is -4-nitro-phenyl, R is —$CH_2$(OH), a is 1, b is 1, Y is —N(H)—, Z is —C(O)—, X is —(R)-CH(OH)—, n is 13, and carbon atom 2 of the compound of formula I is the (S)-isomer.

In another embodiment, $R_1$ is —H, $R_3$ is -4-nitro-phenyl, $R_4$ is —$CH_2$(OH), a is 1, b is 1, Y is —N(H)—, A is —$CH_2$—, X is —(S)-CH(OH)—, n is 13, and carbon atom 2 of the compound of formula I is the (S)-isomer In one embodiment, a is 0, and b is 0.

In another embodiment, $R_3$ is -phenyl, a is 0, and b is 0.

In another embodiment, $R_1$ is —H, $R_3$ is -phenyl, $R_4$ is —$CH_3$, a is 0, and b is 0.

In another embodiment, $R_1$ is —H, $R_2$ is —H, $R_3$ is -phenyl, $R_4$ is —$CH_3$, a is 0, b is 0, X is —(R)-CH(OH)—, n is 14, and carbon atom 2 of the compound of formula I is the (R)-isomer.

In another embodiment, $R_1$ is —H, $R_2$ is —H, $R_3$ is -phenyl, $R_4$ is —$CH_3$, a is 0, b is 0, X is —(S)-CH(OH)—, n is 14, and carbon atom 2 of the compound of formula I is the (R)-isomer.

In another embodiment, the compound of formula (I) is a hydrogen chloride salt where $R_1$ is —H, $R_2$ is —H, $R_3$ is -phenyl, $R_4$ is —$CH_3$, a is 0, b is 0, X is —(S)-CH(OH)—, n is 14, and carbon atom 2 of the compound of formula I is the (R)-isomer (LCL284).

In another embodiment, $R_1$ is —H, $R_2$ is —H, $R_3$ is -phenyl, $R_4$ is —$CH_3$, a is 0, b is 0, X is —(R)-CH(OH)—, n is 14, and carbon atom 2 of the compound of formula I is the (S)-isomer.

In another embodiment, $R_1$ is —H, $R_2$ is —H, $R_3$ is -phenyl, $R_4$ is —$CH_3$, a is 0, b is 0, X is —(S)-CH(OH)—, n is 14, and carbon atom 2 of the compound of formula I is the (R)-isomer.

In another embodiment, $R_1$ is —H, $R_3$ is -phenyl, $R_4$ is —$CH_2$(OH), a is 0, and b is 0.

In another embodiment, $R_1$ is —H, $R_2$ is —H, $R_3$ is -phenyl, $R_4$ is —$CH_2$(OH), a is 0, b is 0, X is —(R)-CH(OH)—, n is 14, and carbon atom 2 of the compound of formula I is the (R)-isomer (LCL18).

In another embodiment, $R_1$ is —H, $R_2$ is —H, $R_3$ is -phenyl, $R_4$ is —$CH_2$(OH), a is 0, b is 0, X is —(S)-CH(OH)—, n is 14, and carbon atom 2 of the compound of formula I is the (R)-isomer.

In another embodiment, $R_1$ is —H, $R_2$ is —H, $R_3$ is -phenyl, $R_4$ is —$CH_2$(OH), a is 0, b is 0, X is —(R)-CH(OH)—, n is 14, and carbon atom 2 of the compound of formula I is the (S)-isomer.

In another embodiment, $R_1$ is —H, $R_2$ is —H, $R_3$ is -phenyl, $R_4$ is —CH$_2$(OH), a is 0, b is 0, X is —(S)-CH(OH)—, n is 14, and carbon atom 2 of the compound of formula I is the (S)-isomer.

In another embodiment, $R_1$ is —H, $R_2$ is —H, $R_3$ is -phenyl, $R_4$ is —CH$_2$(OH), a is 0, b is 0, X is —CH$_2$—, n is 14, and carbon atom 2 of the compound of formula I is the (R)-isomer.

In another embodiment, the compound of formula (I) is a hydrogen chloride salt where $R_1$ is —H, $R_2$ is —H, $R_3$ is -phenyl, $R_4$ is —CH$_2$(OH), a is 0, b is 0, X is —CH$_2$—, n is 14, and carbon atom 2 of the compound of formula I is the (R)-isomer (LCL286).

In another embodiment, $R_1$ is —H, $R_2$ is —H, $R_3$ is -phenyl, $R_4$ is —CH$_2$(OH), a is 0, b is 0, X is —CH$_2$—, n is 14, and carbon atom 2 of the compound of formula I is the (S)-isomer.

In another embodiment, $R_3$ is -4-nitro-phenyl, a is 0, and b is 0.

In another embodiment, $R_1$ is —H, $R_3$ is -4-nitro-phenyl, $R_4$ is CH$_2$(OH), a is 0, and b is 0.

In another embodiment, $R_1$ is —H, $R_2$ is —H, $R_3$ is -4-nitro-phenyl, $R_4$ is —CH$_2$(OH), a is 0, b is 0, X is —(R)-CH(OH)—, n is 14, and carbon atom 2 of the compound of formula I is the (R)-isomer (LCL102).

In another embodiment, the compound of formula I is a hydrogen chloride salt where $R_1$ is —H, $R_2$ is —H, $R_3$ is -4-nitro-phenyl, $R_4$ is —CH$_2$(OH), a is 0, b is 0, X is —(R)-CH(OH)—, n is 14, and carbon atom 2 of the compound of formula I is the (R)-isomer (LCL204).

In another embodiment, $R_1$ is —H, $R_2$ is —H, $R_3$ is -4-nitro-phenyl, $R_4$ is —CH$_2$(OH), a is 0, b is 0, X is —(S)-CH(OH)—, n is 14, and carbon atom 2 of the compound of formula I is the (R)-isomer.

In another embodiment, $R_1$ is —H, $R_2$ is —H, $R_3$ is -4-nitro-phenyl, $R_4$ is —CH$_2$(OH), a is 0, b is 0, X is —(R)-CH(OH)—, n is 14, and carbon atom 2 of the compound of formula I is the (S)-isomer.

In another embodiment, $R_1$ is —H, $R_2$ is —H, $R_3$ is -4-nitro-phenyl, $R_4$ is CH$_2$(OH), a is 0, b is 0, X is —(S)-CH(OH)—, n is 14, and carbon atom 2 of the compound of formula I is the (S)-isomer.

In one embodiment, a is 0, b is 1, and A is —CH$_2$—.

In another embodiment, $R_3$ is -phenyl, a is 0, b is 1, and A is —CH$_2$—.

In another embodiment, $R_1$ is —H, $R_3$ is -phenyl, $R_4$ is —CH$_3$, a is 0, b is 1, and A is —CH$_2$—.

In another embodiment, $R_1$ is —H, $R_3$ is -phenyl, $R_4$ is —CH$_3$, a is 0, b is 1, A is —CH$_2$—, X is —(R)-CH(OH)—, n is 13, and carbon atom 2 of the compound of formula I is the (R)-isomer.

In another embodiment, $R_1$ is —H, $R_3$ is -phenyl, $R_4$ is —CH$_3$, a is 0, b is 1, A is —CH$_2$—, X is —(R)-CH(OH)—, n is 13, and carbon atom 2 of the compound of formula I is the (S)-isomer.

In another embodiment, $R_1$ is —H, $R_3$ is -phenyl, $R_4$ is —CH$_3$, a is 0, b is 1, A is —CH$_2$—, X is —(R)-CH(OH)—, n is 13, and carbon atom 2 of the compound of formula I is the (R)-isomer.

In another embodiment, $R_1$ is —H, $R_3$ is -phenyl, $R_4$ is —CH$_3$, a is 0, b is 1, and A is —CH$_2$—.

In another embodiment, $R_1$ is —H, $R_2$ is —CH$_3$, $R_3$ is -phenyl, $R_4$ is —CH$_3$, a is 0, b is 1, A is —CH$_2$—, X is —(R)-CH(OH)—, n is 13, and carbon atom 2 of the compound of formula I is the (R)-isomer.

In another embodiment, $R_1$ is —H, $R_2$ is —CH$_3$, $R_3$ is -phenyl, $R_4$ is —CH$_3$, a is 0, b is 1, A is —CH$_2$—, X is —(S)-CH(OH)—, n is 13, and carbon atom 2 of the compound of formula I is the (R)-isomer (LCL11).

In another embodiment, $R_1$ is —H, $R_2$ is —CH$_3$, $R_3$ is -phenyl, $R_4$ is —CH$_3$, a is 0, b is 1, A is —CH$_2$—, X is —(R)-CH(OH)—, n is 13, and carbon atom 2 of the compound of formula I is the (S)-isomer.

In another embodiment, $R_1$ is —H, $R_2$ is —CH$_3$, $R_3$ is -phenyl, $R_4$ is —CH$_3$, a is 0, b is 1, A is —CH$_2$—, X is —(S)-CH(OH)—, n is 13, and carbon atom 2 of the compound of formula I is the (S)-isomer.

In another embodiment, $R_1$ is —H, $R_3$ is -phenyl, $R_4$ is —CH$_2$(OH), a is 0, b is 1, and Z is —C(O)—.

In another embodiment, $R_1$ is —H, $R_2$ is —H, $R_3$ is -phenyl, $R_4$ is —CH$_2$(OH), a is 0, b is 1, A is —CH$_2$—, X is —(S)-CH(OH)—, n is 13, and carbon atom 2 of the compound of formula I is the (R)-isomer.

In another embodiment, $R_1$ is —H, $R_2$ is —H, $R_3$ is -phenyl, $R_4$ is —CH$_2$(OH), a is 0, b is 1, A is —CH$_2$—, X is —(R)-CH(OH)—, n is 13, and carbon atom 2 of the compound of formula I is the (S)-isomer.

In another embodiment, $R_1$ is —H, $R_2$ is —H, $R_3$ is -phenyl, $R_4$ is —CH$_2$(OH), a is 0, b is 1, A is —CH$_2$—, X is —(S)-CH(OH)—, n is 14, and carbon atom 2 of the compound of formula I is the (S)-isomer.

In another embodiment, $R_3$ is -4-nitro-phenyl, a is 0, b is 1, and A is —CH$_2$—.

In another embodiment, $R_1$ is 1-pyridinium, $R_3$ is -4-nitro-phenyl, $R_4$ is —CH$_2$(OH), a is 0, b is 1, and A is —CH$_2$—.

In another embodiment, $R_1$ is 1-pyridinium, $R_2$ is —H, $R_3$ is -4-nitro-phenyl, $R_4$ is —CH$_2$(OH), a is 0, b is 1, Z is —C(O)—, X is —(S)-CH(OH)—, n is 15, and carbon atom 2 of the compound of formula I is the (R)-isomer.

In another embodiment, $R_1$ is 1-pyridinium, $R_2$ is —H, $R_3$ is -4-nitro-phenyl, $R_4$ is —CH$_2$(OH), a is 0, b is 1, A is —CH$_2$—, X is —(R)-CH(OH)—, n is 15, and carbon atom 2 of the compound of formula I is the (S)-isomer.

In another embodiment, $R_1$ is 1-pyridinium, $R_2$ is —H, $R_3$ is -4-nitro-phenyl, $R_4$ is —CH$_2$(OH), a is 0, b is 1, A is —CH$_2$—, X is —(S)-CH(OH)—, n is 15, and carbon atom 2 of the compound of formula I is the (S)-isomer.

In one embodiment, $R_1$ is -1-pyridinium, $R_3$ is -phenyl, $R_4$ is —CH$_3$, a is 0, b is 1, and A is —CH$_2$—.

In another embodiment, $R_1$ is -1-pyridinium, $R_2$ is —H, $R_3$ is -phenyl, $R_4$ is —CH$_3$, a is 0, b is 1, A is —CH$_2$—, X is —(R)-CH(OH)—, n is 15, and carbon atom 2 of the compound of formula I is the (R)-isomer.

In another embodiment, $R_1$ is -1-pyridinium, $R_2$ is —H, $R_3$ is -phenyl, $R_4$ is —CH$_3$, a is 0, b is 1, A is —CH$_2$—, X is —(R)-CH(OH)—, n is 15, and carbon atom 2 of the compound of formula I is the (S)-isomer.

In another embodiment, $R_1$ is -1-pyridinium, $R_2$ is —H, $R_3$ is -phenyl, $R_4$ is —CH$_3$, a is 0, b is 1, A is —CH$_2$—, X is —(S)-CH(OH)—, n is 15, and carbon atom 2 of the compound of formula I is the (S)-isomer.

In one embodiment, $R_3$ is -4-(9-pyridinium)nononamide)phenyl, a is 0, b is 1, and A is —CH$_2$—.

In another embodiment, $R_1$ is —H, $R_3$ is -4-(9-pyridinium)nononamide)phenyl, $R_4$ is —CH$_2$(OH), a is 0, b is 1, and A is —CH$_2$—.

In another embodiment, $R_1$ is —H, $R_2$ is —H, $R_3$ is -4-(9-pyridinium)nononamide)phenyl, $R_4$ is —CH$_2$(OH), a is 0, b is 1, A is —CH$_2$—, X is —(S)-CH(OH)—, n is 13, and carbon atom 2 of the compound of formula I is the (R)-isomer.

In another embodiment, $R_1$ is —H, $R_2$ is —H, $R_3$ is -4-(9-pyridinium)nononamide)phenyl, $R_4$ is —CH$_2$(OH), a is 0, b is 1, A is —CH$_2$—, X is —(R)-CH(OH)—, n is 13, and carbon atom 2 of the compound of formula I is the (S)-isomer.

In another embodiment, $R_1$ is —H, $R_2$ is —H, $R_3$ is -4-(9-pyridinium)nononamide)phenyl, $R_4$ is —CH$_2$(OH), a is 0, b is 1, A is —CH$_2$—, X is —(S)-CH(OH)—, n is 13, and carbon atom 2 of the compound of formula I is the (S)-isomer.

In preferred embodiments, the compounds are not N-(1-hydroxy-1-phenylpropan-2-yl)tetradecanamide, N-(1,3-dihydroxy-1-(4-nitrophenyl)propan-2-yl)tetradecanamide, 2-(hexylamino)-1-(4-(hexylamino)phenyl)propane-1,3-diol, 1-(4-nitrophenyl)-2-(tetradecylamino)propane-1,3-diol or 1-(4-aminophenyl)-2-(tetradecylamino)propane-1,3-diol.

In an embodiment, the invention is directed to a compound of formula I and pharmaceutically acceptable salts thereof, wherein R$_1$ is —H, —OH, —SH, —NH$_2$, —Cl, —Br, —I, C(O)OH, —C(O)NH$_2$, —NH(C=NH)NH$_2$, —NH(R$_2$), or —N-heterocycle having from 5 to 6 atoms in the ring; R$_2$ is —H or —(C$_1$-C$_6$)alkyl; R$_3$ is -phenyl; five-membered monocyclic heterocycle; six-membered monocyclic heterocycle; five- and five-membered bicyclic heterocycle; six- and six membered bicyclic heterocycle; five- and six-membered bicyclic heterocycle; five-, five-, and five-membered tricylic heterocycle; six-, six-, and six membered tricylic heterocycle; five-, five-, and six-membered tricylic heterocycle; five-, six-, and six-membered tricylic heterocycle; six-, five-, and six-membered tricylic heterocycle; five-, six-, and five-membered tricylic heterocycle; each of the foregoing being optionally substituted with one or more —R$_5$; R$_4$ is —H, —(C$_1$-C$_6$) alkyl, —CH$_2$(OH), —SH, —NH$_2$, —CH$_2$Cl, —CH$_2$Br, —CH$_2$I, —C(O)OH, —C(O)NH$_2$; R$_5$ is —(C$_1$-C$_6$)alkyl, —F, —Cl, —Br, —I—NH(R$_{2a}$), —NO$_2$, or an amide of formula

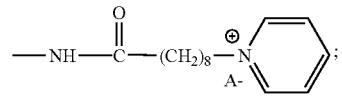

R$_{2a}$ is —H or —(C$_1$-C$_6$)alkyl; X is —C(O)—; Y is —N(H)—; A is —CH$_2$— or —CH(OH)—; a is 1; b is n is an integer from 2 to 22; and A$^-$ is a pharmaceutically acceptable counter-anion.

In a specific embodiment, n=8 to 22. In preferred embodiments, the compounds are LCL16, LCL 17, LCL15 and LCL81.

In a specific embodiment, the invention is directed to a compound of formula I and pharmaceutically acceptable salts thereof, wherein: R$_1$ is —H, —OH, —SH, —NH$_2$, —Cl, —Br, —I, —C(O)OH, —C(O)NH$_2$, —NH(C=NH)NH 2, —NH(R$_2$), or —N-heterocycle having from 5 to 6 atoms in the ring; R$_2$ is —H or —(C$_1$-C$_6$)alkyl; R$_3$ is -phenyl; five-membered monocyclic heterocycle; six-membered monocyclic heterocycle; five- and five-membered bicyclic heterocycle; six- and six membered bicyclic heterocycle; five- and six-membered bicyclic heterocycle; five-, five-, and five-membered tricylic heterocycle; six-, six-, and six membered tricylic heterocycle; five-, five-, and six-membered tricylic heterocycle; five-, six-, and six-membered tricylic heterocycle; six-, five-, and six-membered tricylic heterocycle; five-, six-, and five-membered tricylic heterocycle; each of the foregoing being optionally substituted with one or more —R$_5$; R$_4$ is —H, —(C$_1$-C$_6$)alkyl, —CH$_2$(OH), —SH, —NH$_2$, —CH$_2$Cl, —CH$_2$Br, —CH$_2$I, —C(O)OH, —C(O)NH$_2$; R$_5$ is —(C$_1$-C$_6$)alkyl, —F, —Cl, —Br, —I, —NH(R$_{2a}$), —NO$_2$, or an amide of formula

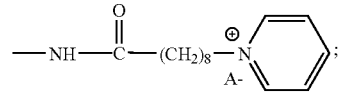

R$_{2a}$ is —H or —(C$_1$-C$_6$)alkyl; X is —C(O)— or —C(S)-; Y is —N(H)—; A is —CH$_2$— or —CH(OH)—; a is 1; b is 1; n is an integer from 2 to 22; and A$^-$ is a pharmaceutically acceptable counter-anion.

In a specific embodiment, the invention is directed to a compound of formula I; and pharmaceutically acceptable salts thereof, wherein: R$_1$ is —N-heterocycle having from 5 to 6 atoms in the ring; R$_2$ is —H or —(C$_1$-C$_6$)alkyl; R$_3$ is -phenyl; five-membered monocyclic heterocycle; six-membered monocyclic heterocycle; five- and five-membered bicyclic heterocycle; six- and six membered bicyclic heterocycle; five- and six-membered bicyclic heterocycle; five-, five-, and five-membered tricylic heterocycle; six-, six-, and six membered tricylic heterocycle; five-, five-, and six-membered tricylic heterocycle; five-, six-, and six-membered tricylic heterocycle; six-, five-, and six-membered tricylic heterocycle; five-, six-, and five-membered tricylic heterocycle; each of the foregoing being optionally substituted with one or more —R$_5$; R$_4$ is —H, —(C$_1$-C$_6$)alkyl, —CH$_2$(OH), —SH, —NH$_2$, —CH$_2$Cl, —CH$_2$Br, —CH$_2$I, —C(O)OH, —C(O)NH$_2$; R$_5$ is —(C$_1$-C$_6$)alkyl, —F, —Cl, —Br, —I, —NH(R$_{2a}$), —NO$_2$, or an amide of formula;

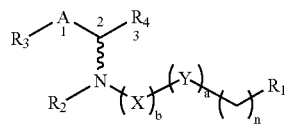

R$_{2a}$ is —H or —(C$_1$-C$_6$)alkyl; X is —CH$_2$—, —CH((C$_1$-C$_6$)alkyl)-, —C(O)—, or —C(S)-; Y is —CH$_2$—; —C(O)—, —N(H)—, or —O—; A is —CH$_2$— of —CH(OH)—; a is 0 or 1; b is 0 or 1; n is an integer from 2 to 22; and A$^-$ is a pharmaceutically acceptable counter-anion.

In specific embodiments, the compounds are LCL85, LCL120 and LCL82.

In an embodiment, the invention is directed to a compound of formula:

and pharmaceutically acceptable salts thereof, wherein:
R$_1$ is H, OH, —SH, —NH$_2$, —Cl, —Br, —I, —C(O)OH, —C(O)NH$_2$, —NH(C=NH)NH$_2$, —NH(R$_2$), or —N-heterocycle having from 5 to 6 atoms in the ring;
R$_2$ is —H or —(C$_1$-C$_6$)alkyl;
R$_3$ is -phenyl; five-membered monocyclic heterocycle; six-membered monocyclic heterocycle; five- and five-membered bicyclic heterocycle; six- and six membered bicyclic heterocycle; five- and six-membered bicyclic heterocycle; five-, five-, and five-membered tricylic heterocycle; six-, six-, and six membered tricylic heterocycle; five-, five-, and six-membered tricylic heterocycle; five-, six-, and six-membered tricylic heterocycle; six-, five-, and six-membered tricylic heterocycle; five-, six-, and five-membered tricylic heterocycle; each of the foregoing being optionally substituted with one or more —$R_5$;

$R_4$ is —H, —($C_2$-$C_6$)alkyl, —SH, —$NH_2$, —$CH_2Cl$, —$CH_2Br$, —$CH_2I$, —C(O)OH, —C(O)$NH_2$;

$R_5$ is —($C_1$-$C_6$)alkyl, —F, —Cl, —Br, —I, —NH($R_{2a}$), —$NO_2$, or an amide of formula

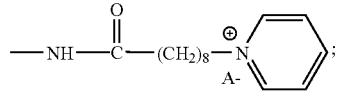

$R_{2a}$ is —H or —($C_1$-$C_6$)alkyl;
X is —C(O)—, or —C(S)-;
Y is —$CH_2$—; —C(O)—, —N(H)—, or —O—;
A is —$CH_2$— or —CH(OH)—;
a is 0 or 1;
b is 0 or 1;
n is an integer from 2 to 22; and
$A^-$ is a pharmaceutically acceptable counter-anion. In preferred embodiments, these compounds are useful for treatment of hyperproliferative diseases.

In another embodiment, the invention is directed to A compound of formula:

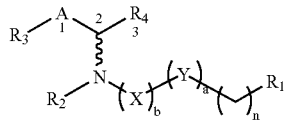

and pharmaceutically acceptable salts thereof, wherein:
$R_1$ is —N-heterocycle having from 5 to 6 atoms in the ring;
$R_2$ is —H or —($C_1$-$C_6$)alkyl;
$R_3$ is -phenyl; five-membered monocyclic heterocycle; six-membered monocyclic heterocycle; five- and five-membered bicyclic heterocycle; six- and six membered bicyclic heterocycle; five- and six-membered bicyclic heterocycle; five-, five-, and five-membered tricylic heterocycle; six-, six-, and six membered tricylic heterocycle; five-, five-, and six-membered tricylic heterocycle; five-, six-, and six-membered tricylic heterocycle; six-, five-, and six-membered tricylic heterocycle; five-, six-, and five-membered tricylic heterocycle, each of the foregoing being optionally substituted with one or more —$R_5$;

$R_4$ is —H, —($C_1$-$C_6$)alkyl, —$CH_2$(OH), —SH, —$NH_2$, —$CH_2Cl$, —$CH_2Br$, —$CH_2I$, —C(O)OH, —C(O)$NH_2$;

$R_5$ is —($C_1$-$C_6$)alkyl, —F, —Cl, —Br, —I, or an amide of formula

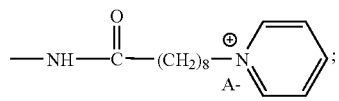

$R_{2a}$ is —H or —($C_1$-$C_6$)alkyl
X is —C(O)—;
Y is —$CH_2$—; —C(O)—, —N(H)—, or —O—;
A is —$CH_2$— or —CH(OH)—;
a is 0 or 1;
b is 0 or 1;
n is an integer from 2 to 22; and $A^-$ is a pharmaceutically acceptable counter-anion. In a preferred embodiment, these compounds are used in combination with FasL gene therapy for the treatment of a hyperproliferative disease.

In a preferred embodiment, the invention is directed to a method of treatment for diseases using a compound of formula:

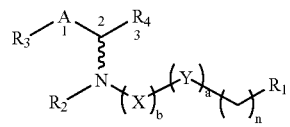

and pharmaceutically acceptable salts thereof, wherein:
$R_1$ is H, or —OH, —SH, —$NH_2$, —Cl, —Br, —I, —C(O)OH, —C(O)$NH_2$, —NH(C=NH)$NH_2$, —NH($R_2$), or —N-heterocycle having from 5 to 6 atoms in the ring;
$R_2$ is —H or —($C_1$-$C_6$)alkyl;
$R_3$ is -phenyl; five-membered monocyclic heterocycle; six-membered monocyclic heterocycle; five- and five-membered bicyclic heterocycle; six- and six membered bicyclic heterocycle; five- and six-membered bicyclic heterocycle; five-, five-, and five-membered tricylic heterocycle; six-, six-, and six membered tricylic heterocycle; five-, five-, and six-membered tricylic heterocycle; five-, six-, and six-membered tricylic heterocycle; six-, five-, and six-membered tricylic heterocycle; five-, six-, and five-membered tricylic heterocycle; each of the foregoing being optionally substituted with one or more —$R_5$;

$R_4$ is —H, —($C_1$-$C_6$)alkyl, —$CH_2$(OH), —SH, —$NH_2$, —$CH_2Cl$, —$CH_2Br$, —$CH_2I$, —C(O)OH, —C(O)$NH_2$;

$R_5$ is —($C_1$-$C_6$)alkyl, —F, —Cl, —Br, —I, —NH($R_{2a}$), —$NO_2$, or an amide of formula

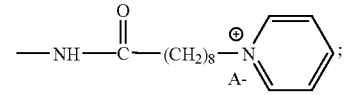

$R_{2a}$ is —H or —($C_1$-$C_6$)alkyl;
X is —$CH_2$—, —CH(($C_1$-$C_6$)alkyl)-, —C(O)—, or —C(S)-;
Y is —$CH_2$—; —C(O)—, —N(H)—, or —O—;
A is —$CH_2$— or —CH(OH)—;
a is 0 or 1;
b is 0 or 1;
n is an integer from 2 to 22; and
$A^-$ is a pharmaceutically acceptable counter-anion,
in combination with a therapeutic agent comprising an expressible nucleic acid encoding a Fas ligand or a functional equivalent thereof.

In a preferred embodiment, the invention is directed to a compound of formula:

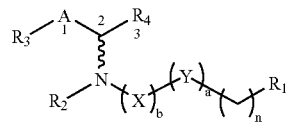

and pharmaceutically acceptable salts thereof, wherein:
$R_1$ is H, OH, —SH, —$NH_2$, —Cl, —Br, —I, —C(O)OH, —C(O)$NH_2$, —NH(C=NH)$NH_2$, —NH($R_2$), or —N-heterocycle having from 5 to 6 atoms in the ring;
$R_2$ is —H or —($C_1$-$C_6$)alkyl;

$R_3$ is -phenyl; five-membered monocyclic heterocycle; six-membered monocyclic heterocycle; five- and five-membered bicyclic heterocycle; six- and six membered bicyclic heterocycle; five- and six-membered bicyclic heterocycle; five-, five-, and five-membered tricylic heterocycle; six-, six-, and six membered tricylic heterocycle; five-, five-, and six-membered tricylic heterocycle; five-, six-, and six-membered tricylic heterocycle; six-, five-, and six-membered tricylic heterocycle; five-, six-, and five-membered tricylic heterocycle; each of the foregoing being optionally substituted with one or more —$R_5$;

$R_4$ is —H, —($C_2$-$C_6$)alkyl, —SH, —$NH_2$, —$CH_2Cl$, —$CH_2Br$, —$CH_2I$, —C(O)OH, —C(O)$NH_2$;

$R_5$ is —($C_1$-$C_6$)alkyl, —F, —Cl, —Br, —I, —NH($R_{2a}$), —$NO_2$, or an amide of formula

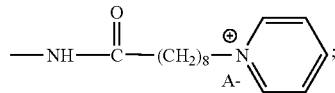

$R_{2a}$ is —H or —($C_1$-$C_6$)alkyl

X is —$CH_2$—, —CH(($C_1$-$C_6$)alkyl)-, —C(O)—, or —C(S)-;

Y is —$CH_2$—; —C(O)—, —N(H)—, or —O—;

A is —$CH_2$— or —CH(OH)—;

a is 0 or 1;

b is 0 or 1;

n is an integer from 2 to 22; and $A^-$ is a pharmaceutically acceptable counter-anion.

In another preferred embodiment, the invention is directed to a compound of formula:

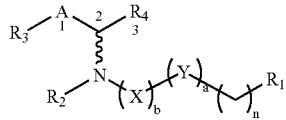

and pharmaceutically acceptable salts thereof, wherein:

$R_1$ is H, OH, —SH, —$NH_2$, —Cl, —Br, —I, —C(O)OH, —C(O)$NH_2$, —NH(C=NH)$NH_2$, —NH($R_2$), or —N-heterocycle having from 5 to 6 atoms in the ring;

$R_2$ is —H or —($C_1$-$C_6$)alkyl;

$R_3$ is five-membered monocyclic heterocycle; six-membered monocyclic heterocycle; five- and five-membered bicyclic heterocycle; six- and six membered bicyclic heterocycle; five- and six-membered bicyclic heterocycle; five-, five-, and five-membered tricylic heterocycle; six-, six-, and six membered tricylic heterocycle; five-, five-, and six-membered tricylic heterocycle; five-, six-, and six-membered tricylic heterocycle; six-, five-, and six-membered tricylic heterocycle; five-, six-, and five-membered tricylic heterocycle; each of the foregoing being optionally substituted with one or more —$R_5$;

$R_4$ is —H, —($C_1$-$C_6$)alkyl, —$CH_2$(OH), —SH, —$NH_2$, —$CH_2Cl$, —$CH_2Br$, —$CH_2I$, —C(O)OH, —C(O)$NH_2$;

$R_5$ is —($C_1$-$C_6$)alkyl, —F, —Cl, —Br, —I, —NH($R_{2a}$), —$NO_2$, or an amide of formula

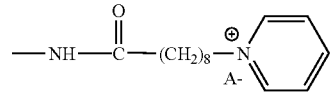

$R_{2a}$ is —H or —($C_1$-$C_6$)alkyl;

X is —$CH_2$—, —CH(($C_1$-$C_6$)alkyl)-, —C(O)—, or —C(S)-;

Y is —$CH_2$—; —C(O)—, —N(H)—, or —O—;

A is —$CH_2$— or —CH(OH)—;

a is 0 or 1;

b is 0 or 1;

n is an integer from 2 to 22; and $A^-$ is a pharmaceutically acceptable counter-anion.

In a preferred embodiment, the invention is directed to a compound of formula:

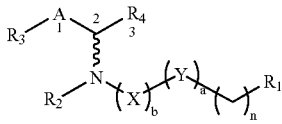

and pharmaceutically acceptable salts thereof, wherein:

$R_1$ is H, OH, —SH, —$NH_2$, —Cl, —Br, —I, —C(O)OH, —C(O)$NH_2$, —NH(C=NH)$NH_2$, —NH($R_2$), or —N-heterocycle having from 5 to 6 atoms in the ring;

$R_2$ is —H or —($C_1$-$C_6$)alkyl;

$R_3$ is -phenyl; five-membered monocyclic heterocycle; six-membered monocyclic heterocycle; five- and five-membered bicyclic heterocycle; six- and six membered bicyclic heterocycle; five- and six-membered bicyclic heterocycle; five-, five-, and five-membered tricylic heterocycle; six-, six-, and six membered tricylic heterocycle; five-, five-, and six-membered tricylic heterocycle; five-, six-, and six-membered tricylic heterocycle; six-, five- and six-membered tricylic heterocycle; five-, six-, and five-membered tricylic heterocycle; each of the foregoing being optionally substituted with one or more —$R_5$;

$R_4$ is —H, —($C_2$-$C_6$)alkyl, —SH, —$NH_2$, —$CH_2Cl$, —$CH_2Br$, —$CH_2I$, —C(O)OH, —C(O)$NH_2$;

$R_5$ is —($C_1$-$C_6$)alkyl, —F, —Cl, —Br, —I, —NH($R_{2a}$), —$NO_2$, or an amide of formula

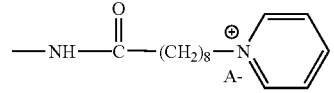

$R_{2a}$ is —H or —($C_1$-$C_6$)alkyl;

X is —$CH_2$—, —CH(($C_1$-$C_6$)alkyl)-, —C(O)—, or —C(S)-;

Y is —$CH_2$—; —C(O)—, —N(H)—, or —O—;

A is —$CH_2$— or —CH(OH)—;

a is 0 or 1;

b is 0 or 1;

n is an integer from 2 to 22; and $A^-$ is a pharmaceutically acceptable counter-anion.

In another embodiment, the invention is directed to a compound of formula:

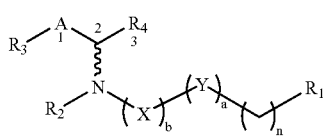

and pharmaceutically acceptable salts thereof, wherein:

$R_1$ is H, —OH, —SH, —$NH_2$, —Cl, —Br, —I, —C(O)OH, —C(O)$NH_2$, —NH(C=NH)$NH_2$, —NH($R_2$), or —N-heterocycle having from 5 to 6 atoms in the ring;

$R_2$ is —H or —($C_1$-$C_6$)alkyl;

$R_3$ is -phenyl substituted with one or more $R_5$; or $R_3$ is five-membered monocyclic heterocycle; six-membered monocyclic heterocycle; five- and five-membered bicyclic heterocycle; six- and six membered bicyclic heterocycle; five- and six-membered bicyclic heterocycle; five-, five-, and five-membered tricylic heterocycle; six-, six-, and six membered tricylic heterocycle; five-, five-, and six-membered tricylic heterocycle; five-, six-, and six-membered tricylic heterocycle; six-, five-, and six-membered tricylic heterocycle; five-, six-, and five-membered tricylic heterocycle, each of which being optionally substituted with one or more —$R_5$;

$R_4$ is —H, —($C_1$-$C_6$)alkyl, —$CH_2$(OH), —SH, —$NH_2$, —$CH_2$Cl, —$CH_2$Br, —$CH_2$I, —C(O)OH, —C(O)$NH_2$;

$R_5$ is —($C_1$-$C_6$)alkyl, —F, —Cl, —Br, —I, —NH($R_{2a}$)—, or an amide of formula:

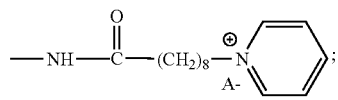

$R_{2a}$ is —H or —($C_1$-$C_6$)alkyl;

X is —$CH_2$—, —CH(($C_1$-$C_6$)alkyl)-, —C(O)—, or —C(S)-;

Y is —$CH_2$—; —C(O)—, —N(H)—, or —O—;

A is —$CH_2$— or —CH(OH)—;

a is 0 or 1;

b is 0 or 1;

n is an integer from 2 to 22; and $A^-$ is a pharmaceutically acceptable counter-anion.

5.2 Synthesis of Ceramide Analogs

Methods of synthesis of the ceramide analogs of the invention is generally disclosed in FIGS. 2C and 2D. Details of specific exemplary compounds are disclosed in Section 6 infra.

5.3 Therapeutic Uses of Ceramide Analogs

The present invention provides the uses of the compounds of the invention for treatment, prophylaxis, management or amelioration of one or more symptoms associated with various diseases and disorders. Such therapeutic compounds are ceramide analogs, such as but not limited to the compounds described in the previous section under Formula I, and analogs and derivatives thereof.

Ceramide modulates a number of biochemical and cellular responses to stress, including apoptosis, cell-cycle arrest and cell senescence. (For review, see Hannun et al., 2000, Trends in Cell Biol. 10:73-80; Mathias et al., 1998, Biochem. J. 335: 465-480). Several extracellular agents and stress stimuli, such as tumor necrosis factor α, chemotherapeutic agents and heat are known to cause ceramide accumulation. One approach to cause accumulation of ceramide is accomplished by regulating the activities of enzymes such as ceramidase which is involved in the metabolism of ceramide. The changes in the ceramide concentration are sufficient to reproduce many of the biological effects of cytokines and stress inducers that are coupled to ceramide accumulation. The accumulation of ceramides also reproduce many of the features of cell senescence. In many cell types, ceramides cause cell differentiation, both morphologically and through the activation of biochemical programs of cell differentiation. Ceramide also causes apoptosis in most cancer cells which can be accompanied by cell-cycle arrest. Thus, according to the present invention, modulation of the levels of ceramide or sphingosine through the methods of the present invention can bring about treatment and prevention of diseases that are related to stress response and apoptosis. Several exemplary diseases and disorders are disclosed below which may be treated or prevented by the methods of the present invention.

Without being bound by any theories, the ceramide analogs of the invention can act as a modulator of one or more ceramidases that are present in a cell or in an organelle of a cell. Preferably, the organelle is a positively charged organelle, such as but not limited to a lysosome. Acid ceramidases are thus preferred targets of the ceramide analogs of the invention. Regardless of the underlying mechanisms, the ceramide analogs can induce cell death.

In one embodiment, the present invention provides a method of increasing the level of ceramide in a cell comprising contacting the cell with a compound that inhibits the ceramidase activity.

In another embodiment, the invention provides a method of inhibiting the formation of sphingosine in a cell comprising contacting the cell with a compound that inhibits the ceramidase activity such that the amount of sphingosine formed as a result of conversion from ceramide is reduced.

In yet another embodiment, the invention provides a method of increasing the intracellular levels of ceramide in an animal comprising administering to the animal an effective amount of a compound that inhibits the ceramidase activity of the ceramidase protein in the animal's cells.

In yet another embodiment, the invention provides a method of inhibiting the intracellular formation of sphingosine in an animal comprising administering to said animal an effective amount of compound that inhibits the ceramidase activity of the ceramidase protein in the animal's cells.

In specific embodiments, the compound that inhibits ceramidase function are administered to a subject therapeutically or prophylactically: (1) in diseases or disorders involving an increased (relative to normal or desired) level of ceramidase protein or function, for example, in patients where ceramidase protein is biologically overactive or overexpressed; or (2) in diseases or disorders wherein in vitro (or in vivo) assays indicate the utility of ceramide analog administration. The increased level in ceramidase protein or function can be readily detected, e.g., by obtaining a patient tissue sample (e.g., from biopsy tissue) and assaying it in vitro for RNA or protein levels, structure and/or activity of the expressed ceramidase RNA or protein. Many methods standard in the art can be thus employed, including but not limited to ceramidase enzyme assays, immunoassays to detect and/or visualize ceramidase protein (e.g., Western blot, immunoprecipitation followed by sodium dodecyl sulfate polyacrylamide gel electrophoresis, immunocytochemistry, etc.) and/or hybridization assays to detect ceramidase expression by detecting and/or visualizing ceramidase mRNA (e.g., Northern assays, dot blots, in situ hybridization, etc.), etc.

According to the invention, disorders involving cell hyperproliferation or dysfunctional sphingolipid signal transduction are treated or prevented by administration of a compound to a subject that inhibits ceramidase function. These diseases and disorders include, but are not limited to, diseases or disorders related to cell proliferation, cell attachment, cell immigration, granulation tissue development, primary and metastatic neoplastic diseases, inflammation, cardiovascular disease, stroke, ischemia or atherosclerosis. Diseases and disorders involving cell overproliferation that can be treated or prevented include but are not limited to cancers, premalignant conditions (e.g., hyperplasia, metaplasia, dysplasia), benign tumors, hyperproliferative disorders, and benign dysproliferative disorders. Cancer is characterized primarily by an increase in the number of abnormal cells derived from a given normal tissue, invasion of adjacent tissues by these abnormal cells, and lymphatic or blood-borne. Malignancies and related disorders that can be treated, prevented, managed, amerliorated, particularly metastatic cancer, by administration of a compound of the invention that inhibits ceramidase function as discussed below (for a review of such disorders, see Fishman et al., 1985, *Medicine,* 2d Ed., J.B. Lippincott Co., Philadelphia):

In another embodiment, disorders in which cell proliferation is deficient or is desired can be treated or prevented by administration of a compound of the invention to a subject that promotes ceramidase function.

The present invention encompasses methods for treating or preventing diseases and disorders wherein the treatment or prevention would be improved by administration of the ceramide analogs, (i.e., inhibitors or activators) of the present invention.

In various embodiments, "treatment" or "treating" refers to an amelioration of disease or disorder, or at least one discernible symptom thereof. "Treatment" or "treating" also refers to an amelioration of at least one measurable physical parameter associated with disease or disorder not necessarily discernible by the subject. "Treatment" or "treating" may also refer to inhibiting the progression of a disease or disorder either physically, e.g., stabilization of a discernible symptom, physiologically, e.g., stabilization of a physical parameter, or both. "Treatment" or "treating" also refers to delaying the onset of a disease or disorder.

In certain embodiments, the methods and compositions of the present invention are useful as a preventative measure against disease or disorder. As used herein, "prevention" or "preventing" refers to a reduction of the risk of acquiring a given disease or disorder.

Preferably, the compounds of the invention are used to treat cancer, cancer metastasis, atherosclerosis, stenosis, inflammation, asthma, and atopic dermatitis.

In certain embodiments, the invention provides methods for treating or preventing diseases or disorders comprising administration of a ceramide analog in combination with other treatments.

Cancers and related disorders that can be treated or prevented by methods and compositions of the present invention include but are not limited to the following: Leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's acroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoid-cystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

In preferred embodiments, the methods and compositions of the invention are used for the treatment and/or prevention of leukemia, breast, colon, ovarian, lung, and prostate cancers, and melanoma.

The compounds of the invention that inhibits ceramidase activity can also be administered to treat premalignant conditions and to prevent progression to a neoplastic or malignant state. Such prophylactic or therapeutic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W.B. Saunders Co., Philadelphia, pp. 68-79.)

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a compound that inhibits ceramidase function. Such characteristics of a transformed phenotype include morphology changes, looser substratum attachment, loss of contact inhibition, loss of anchorage dependence, protease release, increased sugar transport, decreased serum requirement, expression of fetal antigens, etc.

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia) is indicative of the desirability of prophylactic intervention. The gene of the human ceramidase of the invention is localized on chromosome 10 (10q11) (i.e., LOC6392). Base on this location, ceramidase may be involved in diseases associated with this region, in addition to the disease and disorder discussed above, which include adenocarcinoma (thyroid), acute myeloid leukemia, and squamous cell cancer, especially that which is associated with the Nasopharynx region.

In other embodiments, a patient which exhibits one or more of the following predisposing factors for malignancy is treated by administration of an effective amount of the ceramide analogs of the invention: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 197, *Basic Pathology*, 2d Ed., W.B. Saunders Co., Philadelphia, pp. 112-113) etc.).

The invention encompasses methods for treating or preventing a cancer or metastasis in a subject comprising in any order the steps of administering to the subject a ceramide analog. In certain embodiments, the compositions and methods of the invention can be used to prevent, inhibit or reduce the growth or metastasis of cancerous cells. In a specific embodiment, the administration of a ceramide analog inhibits or reduces the growth or metastasis of cancerous cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth or metastasis in absence of the administration of said ceramide analog.

The invention encompasses methods of disease treatment or prevention that provide better therapeutic profiles than current single agent therapies or even current combination therapies. Encompassed by the invention are combination therapies that have additive potency or an additive therapeutic effect while reducing or avoiding unwanted or adverse effects.

Other cancer treatment that may be used in combination of the administration of the ceramide analog of the present invention include the use of one or more compounds which include, but are not limited to, chemoagents, immunotherapeutics, cancer vaccines, anti-angiogenic agents, cytokines, hormone therapies, gene therapies, biological therapies, and radiotherapies. While maintaining or enhancing efficacy of treatment, preferably the methods of the present invention increase patient compliance, improve therapy and/or reduce unwanted or adverse effects.

In a specific embodiment, a ceramide analog is administered to a subject receiving a treatment modality for the treatment of cancer wherein the subject may experience unwanted or adverse effects to treatment with the treatment modality alone, e.g., the treatment modality may be toxic or harmful at its effective dose, administered alone. Given the invention, the ceramide analog can improve the therapeutic benefit of the treatment modality such that the dosage or frequency of administration of the treatment modality can be lowered when administered in conjunction with the ceramide analog. In a preferred embodiment, a ceramide analog is administered to allow lower and/or less frequent doses of chemotherapy or radiation therapy.

In a specific embodiment, the methods of the invention encompass the administration of one or more angiogenesis inhibitors such as but not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); Fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates.

Additional examples of anti-cancer agents that can be used in the various-embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide amino triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin like growth factor 1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. These two agents are particularly useful when used in methods employing thalidomide and a topoisomerase inhibitor.

In another embodiment, the treatment of the present invention further includes the administration of one or more immunotherapeutic agents, such as antibodies and immunomodulators, which include, but are not limited to, HERCEPTIN®, RITUXAN®, OVAREX™, PANOREX®, BEC2, IMC-C225, VITAXIN™, CAMPATH® I/H, Smart MI95, LYMPHOCIDE™, Smart I D10, and ONCOLYM™, rituximab, gemtuzumab, or trastuzumab.

In another embodiment, the treatment of the present invention further includes administering one or more anti-angiogenic agents, which include, but are not limited to, angiostatin, thalidomide, kringle 5, endostatin, other Serpins, antithrombin, 29 kDa N-terminal and 40 kDa C-terminal proteolytic fragments of fibronectin, 16 kDa proteolytic fragment of prolactin, 7.8 kDa proteolytic fragment of platelet factor-4, a 13-amino acid peptide corresponding to a fragment of platelet factor-4 (Maione et al., 1990, *Cancer Res.* 51:2077), a 14-amino acid peptide corresponding to a fragment of collagen I (Tolma et al., 1993, *J. Cell Biol.* 122:497), a 19 amino acid peptide corresponding to a fragment of Thrombospondin I (Tolsma et al., 1993, *J. Cell Biol.* 122: 497), a 20-amino acid peptide corresponding to a fragment of SPARC (Sage et al., 1995, *J. Cell. Biochem.* 57:1329-), or any fragments, family members, or derivatives thereof, including pharmaceutically acceptable salts thereof.

In another embodiment, the treatment method further comprise the use of radiation.

In another embodiment, the treatment method further comprises the administration of one or more cytokines, which includes, but is not limited to, lymphokines, tumor necrosis factors, tumor necrosis factor-like cytokines, lymphotoxin-a, lymphotoxin-b, interferon-a, interferon-b, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40, CD27, CD30, CD40 or CD137 ligands, Fas Fas ligand, 4-1BBL, endothelial monocyte activating protein or any fragments, family members, or derivatives thereof, including pharmaceutically acceptable salts thereof.

In yet another embodiment, the treatment method further comprises hormonal treatment. Hormonal therapeutic treatments comprise hormonal agonists, hormonal antagonists (e.g., flutamide, tamoxifen, leuprolide acetate (LUPRON™), LH-RH antagonists), inhibitors of hormone biosynthesis and processing, steroids (e.g., dexamethasone, retinoids, betamethasone, cortisol, cortisone, prednisone, dehydrotestosterone, glucocorticoids, mineralocorticoids, estrogen, testosterone, progestins), antigestagens (e.g., mifepristone, onapristone), and antiandrogens (e.g., cyproterone acetate).

Other disorders of proliferation that may benefit from inhibition of ceramidase including cardiovascular diseases.

Vascular interventions, including angioplasty, stenting, atherectomy and grafting for the treatment of cardiovascular diseases are often complicated by undesirable effects. One of the adverse reactions to vascular intervention include endothelial and smooth muscle cell proliferation which can lead to hyperplasia, or more specifically, restenosis which is the re-clogging of the artery, occlusion of blood vessels, reperfusion injury, platelet aggregation, and calcification. In this model, an injurious stimulus induces expression of growth-stimulatory cytokines such as interleukin 1 and tumor necrosis factor. Libby et al., *Cascade Model of Restenosis* 1992, Circulation 86(6): III-47-III52. There is evidence which shows that ceramide inhibit the growth of endothelia and smooth muscle cells of the coronary artery.

Various therapies have been attempted to treat or prevent stenosis or restenosis. However, there remains a great need for therapies directed to the prevention and treatment of cardiovascular diseases caused by hyperplasia of endothelia and smooth muscle cells. Since it has been shown that ceramide inhibit the growth of endothelia and smooth muscle cells of the coronary artery, it is therefore desirable to raise the level of ceramide for the treatment and prevention of cardiovascular diseases. Recently, Kester et al. show that ceramide used in angioplasty prevents restenosis. Kester et al., 2000, Circ. Res. 87(4):282-8. Alternative, and more effectively, one aspect of the present invention provides treatment and prevention of restenosis by adjusting the level of ceramide through administering ceramide analogs.

Accordingly, it is therefore desirable to raise the level of ceramide for the treatment and prevention of cardiovascular diseases. This can be accomplished by adjusting the intracellular level of ceramide by using the compounds and methods of the invention. The outcome of a treatment is to at least produce in a treated subject a healthful benefit, which in the case of cardiovascular diseases, includes but is not limited to a reduced risk of re-clogging of arteries after a vascular intervention procedure, and improved circulation.

In a specific embodiment, the present invention provides a method for preventing, treating, managing or ameliorating an autoimmune or inflammatory disorder or one or more symptoms thereof, said method comprising administering to a subject in need thereof a prophylactically or therapeutically effective amount of ceramide analogs and a prophylactically or therapeutically effective amount of one or more immunomodulatory agents.

Interleukin-1 is a major inducer of inflammation and TNF is an important regulator of the reaction. Both cytokines can activate ceramidase, and thus inhibiting the activity of ceramidase can result in an anti-inflammatory effect. This may involve the prevention of the formation of sphingosine and sphingosine phosphate which have pro-inflammatory effects. Also, inhibition of ceramidase may prevent the hyperproliferation of immune cells that are important for inflammation. There is evidence which suggests that an increase in ceramide and a decrease in sphingosine leads to a decrease in sphingosine phosphate. Preliminary data show that in mouse fibroblast cells, L929, TNFα increases the level of ceramide and leads to PGE2 release from these cells. The release of PGE2 is also shown to be inhibited by D-(N-myristolyamino)-1-phenyl-1-propanol), D-MAPP, which is an inhibitor of one of the ceramidase. This observation may be important for inhibiting inflammatory reactions that occur in conditions, such as but not limited to rheumatoid arthritis. Thus, it is possible to treat or prevent inflammation by regulating the level of cellular ceramide using the method of the invention. As discussed above, ceramide level can be increased by administering compounds of the present invention that can inhibit mitochondrial ceramidase.

Examples of autoimmune disorders include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections. Some autoimmune disorders are associated with an inflammatory condition. Thus, there is overlap between what is considered an autoimmune disorder and an inflammatory disorder. Therefore, some autoimmune disorders may also be characterized as inflammatory disorders.

The present invention provides methods of preventing, treating, managing or ameliorating an autoimmune or inflammatory disorder or one or more symptoms thereof, said methods comprising administering to a subject in need of a ceramide analog and one or more immunomodulatory agents. Preferably, the immunomodulatory agents are not administered to a subject with an autoimmune or inflammatory disorder whose mean absolute lymphocyte count is less than 500 cells/mm$^3$, less than 550 cells/mm$^3$, less than 600 cells/mm$^3$, less than 650 cells/mm$^3$, less than 700 cells/mm$^3$, less than 750 cells/mm$^3$, less than 800 cells/mm$^3$, less than 850 cells/mm$^3$ or less than 900 cells/mm$^3$. Thus, in a preferred embodiment, prior to or subsequent to the administration of one or more dosages of one or more immunomodulatory agents to a subject with an autoimmune or inflammatory disorder, the absolute lymphocyte count of said subject is determined by techniques well-known to one of skill in the art, including, e.g., flow cytometry or trypan blue counts.

Examples of immunomodulatory agents include, but are not limited to, methothrexate, leflunomide, cyclophosphamide, cyclosporine A, and macrolide antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators. Examples of T cell receptor modulators include, but are not limited to, anti-T cell receptor antibodies (e.g., anti-CD4 monoclonal antibodies, anti-CD3 monoclonal antibodies, anti-CD8 monoclonal antibodies, anti-CD40 ligand monoclonal antibodies, anti-CD2 monoclonal antibodies) and CTLA4-immunoglobulin. Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, TNF-β, interferon (IFN)-α, IFN-β, IFN-γ, and GM-CSF), anti-cytokine receptor antibodies (e.g., anti-IL-2 receptor antibodies, anti-IL-4 receptor antibodies, anti-IL-6 receptor antibodies, anti-IL-10 receptor antibodies, and anti-IL-12 receptor antibodies), anti-cytokine antibodies (e.g., anti-IFN receptor antibodies, anti-TNF-α antibodies, anti-IL-1β antibodies, anti-IL-6 antibodies, and anti-IL-12 antibodies).

Anti-inflammatory agents have exhibited success in treatment of inflammatory and autoimmune disorders and are now a common and a standard treatment for such disorders. Any anti-inflammatory agent well-known to one of skill in the art can be used in the compositions and methods of the invention. Non-limiting examples of anti-inflammatory agents include non-steroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

The present invention also relates to the treatment of disorders involving deficient cell proliferation (growth) or in which cell proliferation is otherwise desired (e.g., degenerative disorders, growth deficiencies, lesions, physical trauma) by administering compounds that agonize, (promote) ceramidase function (e.g., ceramide-1-phosphate and sphingosine-1-phosphate). Other disorders that may benefit from activation of ceramidase are neurodegenerative disorders (e.g., Alzheimer's disease), and disorders of aging such as immune dysfunction.

As discussed above, like treatment of neoplastic conditions, successful treatment of cardiovascular diseases, inflammation or the above-mentioned diseases can be brought about by techniques which serve to decrease ceramidase activity. Activity can be decreased by, for example, directly decreasing ceramidase gene product activity and/or by decreasing the level of ceramidase gene expression.

Techniques for the determination of effective doses and administration of such compounds are described in Section 5.4. Any technique which serves to selectively administer chemicals to a cell population of interest can be used, for example, by using a delivery complex. Such a delivery complex can comprise an appropriate chemical and a targeting means. Such targeting means can comprise, for example, sterols, lipids, viruses or target cell specific binding agents.

5.4 Pharmaceutical Preparation and Methods of Administration

The compounds described herein can be administered to a patient at therapeutically effective doses to treat or prevent diseases and disorder discussed above. A therapeutically effective dose refers to that amount of a compound sufficient to result in a healthful benefit in the treated subject. See, the *Physician's Desk Reference*® (53$^{rd}$ ed., 1999).

The subject to which a compound of the invention is administered is preferably an animal, including but not limited to mammal such as non-primate (e.g., cows, pigs, horses, chickens, cats, dogs, rats, etc.), and a primate (e.g., monkey such as acynomolgous monkey) and a human. In a preferred embodiment, the subject is a human. The compound of the invention can be utilized for the prevention of a variety of cancers, e.g., in individuals who are predisposed as a result of familial history or in individuals with an enhanced risk to cancer due to environmental factors.

The methods and compositions of the invention may be used in patients who are treatment naive, in patients who have previously received or are currently receiving treatment with other pharmaceutical agents or combinations, including but not limited to anti-cancer agents. Other subjects may include patients that have metastasis or no metastasis.

The methods and compositions of the invention are useful not only in untreated patients but are also useful in the treatment of patients partially or completely un-responsive to other treatments. In various embodiments, the invention provides methods and compositions useful for the treatment of diseases or disorders in patients that have been shown to be or may be refractory or non-responsive to therapies comprising the administration of other agents.

The compound of the invention can also be administered to an animal, preferably a mammal, such as farm animals and pets, to treat, prevent or ameliorate one or more symptoms associated with the disease, disorder, or infection as discussed in Section 5.3.

The absence of decreased level in ceramide protein or function can be readily detected, e.g., by obtaining a patient tissue sample (e.g., from biopsy tissue) and assaying it in vitro for ceramide.

5.4.1 Effective Dose

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. For example, the dosage can range from 10 nM to 100 µM, and preferably 1 to 10 µM. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

Suitable daily doses for the treatment or prevention of a disorder described herein can be readily determined by those skilled in the art. A recommended dose of a compound of the invention is from about 0.1 mg to about 100 mg per day, given as a single once-a-day dose in the morning or as divided doses throughout the day. Preferably, a daily dose is from about 2 mg to about 25 mg per day, more preferably from about 5 mg to about 10 mg per day.

The anti-cancer activity of the therapies used in accordance with the present invention also can be determined by using various experimental animal models of such as cancer animal models such as scid mouse model or nude mice with human tumor grafts known in the art and described in Yamanaka, 2001, Microbiol Immunol 2001; 45(7):507 14.

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which a patient tissue sample is grown in culture, and exposed to or otherwise administered a protocol, and the effect of such protocol upon the tissue sample is observed. A lower level of proliferation or survival of the contacted cells indicates that the Therapeutic is effective to treat the condition in the patient. Alternatively, instead of culturing cells from a patient, Protocols may be screened using cells of a tumor or malignant cell line. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc.

Compounds for use in therapy can be tested in suitable animal model systems prior to testing in humans, including but not limited to in rats, mice, chicken, cows, monkeys, rabbits, etc. The principle animal models for cancer known in the art and widely used include mice, as described in Hann et al., 2001, Curr Opin Cell Biol 2001, 13(6):778 84, which is incorporated herein by reference in its entirety.

Further, any assays known to those skilled in the art can be used to evaluate the prophylactic and/or therapeutic utility of the combinatorial therapies disclosed herein for treatment, prophylaxis, management or amelioration of one or more symptoms associated with the disease, disorder as described in Section 5.3.

Efficacy in treating inflammatory disorders may be demonstrated by detecting the ability of the ceramide analogs of the present invention, or a composition of the invention to reduce or inhibit the inflammation in an animal or to ameliorate or alleviate one or more symptoms associated with an inflammatory disorder. The treatment is considered therapeutic if there is, for example, a reduction is in inflammation or amelioration of one or more symptoms following administration of the ceramide analogs, or a composition of the invention.

5.4.2 Formulations and Use

Various methods can be used to administer a ceramide analog of the invention. Methods of introduction include but are not limited to intradermal, intramuscular, intraperitoneal, intravenous, subcutaneous, intranasal, epidural, inhalation, insufflation (either through the mouth or the nose), oral, buccal, or rectal routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, by means of a catheter, by means of a suppository, or by means of an implant, said implant being of a porous, non-porous, or gelatinous material, including membranes, such as sialastic membranes, or fibers.

In another embodiment, the ceramide analog can be delivered in a vesicle, in particular a liposome (see Langer, Science 249:1527 1533 (1990); Treat et al., in Liposomes in the Therapy of Infectious Disease and Cancer, Lopez-Berestein and Fidler (eds.), Liss, New York, pp. 353 365 (1989); Lopez-Berestein, ibid., pp. 317 327; see generally ibid.)

In yet another embodiment, the ceramide analogs can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228: 190 (1985); During et al., Ann. Neurol. 25:351 (1989); Howard et al., F. Neurosurg. 71:105 (1989)). In yet another embodiment, a controlled release system can be placed in proximity of the therapeutic target, thus requiring only a fraction of the systemic dose (see, e.g., Goodson, in Medical Applications of Controlled Release, supra, vol. 2, pp. 115 138 (1984)).

Other controlled release systems are discussed in the review by Langer (Science 249:1527 1533 (1990)). Other method of delivery of the therapeutics of the present invention may be used for example, as described in U.S. Pat. No. 5,679, 350, which is incorporated by reference in its entirety.

The present invention also provides pharmaceutical compositions. Such compositions comprise a therapeutically effective amount of one or more ceramide analogs and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the ceramide analogs preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The ceramide analogs of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the ceramide analogs of the invention which will be effective in the treatment of a particular disorder or condition will depend on the nature of the disorder or condition, and can be determined by standard clinical techniques. In addition, in vitro assays and animal models may optionally be employed to help identify optimal dosage ranges. The precise dose to be employed in the formulation will also depend on the route of administration, and the seriousness of the disease or disorder, and should be decided according to the judgment of the practitioner and each patient's circumstances.

In specific embodiments, the ceramide analogs of the invention are administered intramuscularly. Suitable dosage ranges for the intramuscular administration are generally about 10 µg to 1 mg per dose, preferably about 10 µg to 100 µg per dose. In one embodiment, the Therapeutic is administered in two doses, where the second dose is administered 24 hours after the first dose; in another embodiment, a compound of the invention is administered in three doses, with one dose being administered on days 1, 4 and 7 of a 7 day regimen.

Suppositories generally contain active ingredient in the range of 0.5% to 10% by weight; oral formulations preferably contain 10% to 95% active ingredient.

The invention also provides a pack or kit for therapeutic use comprising one or more containers filled with one or more of the ingredients of the pharmaceutical compositions of the invention. Optionally associated with such container(S) can be a notice in the form prescribed by a governmental agency regulating the manufacture, use or sale of pharmaceuticals or diagnostic products, which notice reflects approval by the agency of manufacture, use or sale for human administration.

Pharmaceutical compositions for use in accordance with the present invention can be formulated in conventional manner using one or more physiologically acceptable carriers or excipients.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the alt. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compounds can be formulated for parenteral administration (i.e., intravenous or intramuscular) by injection, via, for example, bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

5.5 Combination Therapy

In a specific embodiment, the invention encompasses methods of treatment that combines the administration of a ceramide analog with a non-phenylamino alcohol based therapeutic modality that induces apoptosis, such as an apoptosis-signaling ligand, and preferably, the Fas ligand. A preferred example of this approach is Fas ligand (FasL) gene therapy.

Thus, the present invention provides methods and compositions for treating cancer, in particular, solid tumors, by expressing one or more apoptosis-signaling ligands, such as FasL, preferably in a site-specific and controlled manner. The controlled expression of these apoptosis signaling ligands should significantly reduce cytotoxicity associated with uncontrolled, systemic administration of these ligands. According to the present invention, an expression vector such as an adenoviral vector carrying a nucleic acid sequence encoding the apoptosis-signaling ligand (e.g., FasL) can be introduced into the tumor site via many pharmaceutically acceptable routes of administration. The cells transduced by the adenovirus expresses the ligand, preferably, as a membrane-bound protein. Through interactions between the apoptosis signaling ligand and an apoptosis-mediating receptor in the cell, a cascade of signal transduction occurs. The event triggers multiple apoptosis pathways in which the apoptosis signal is amplified by expression of multiple apoptotic enzymes such as proteases and endonucleases. Since the interactions between the ligand and the receptor can occur between two cells, the tumor cells that are not transduced by adenovirus can be induced to undergo apoptosis due to a "bystander effect". This effect may be due to specific interactions between the apoptosis-signaling ligand expressed in cells transduced by the ligand expression vector (e.g., adenovirus) and the apoptosis-mediating receptor expressed on the surface of the untransduced tumor cells.

One important feature of the present invention is that expression of the apoptosis-signaling ligand is controlled by a conditional promoter, such as a tissue-specific or an inducible promoter. By controlling the expression of the ligand site-specifically (e.g., using a tissue-specific promoter) and/or flexible adjustment of dosage (e.g., using an inducible promoter), potential systemic toxicity of the ligand should be significantly reduced. In particular, the vector encoding the ligand can be directly injected into the tumor site and locally transfers the ligand into the tumor cells. Depending on the dosage of the ligand to be delivered, the adenoviral vector can be replication competent or replication incompetent. Once injected into the tumor, the adenovirus transduces the tumor cells which, as a result, expresses high levels of the ligand locally. Through interactions between the ligand and the receptor (s) expressed on the surface of the tumor cells, the apoptosis signal is amplified by expression of multiple proteins and enzymes along the pathways of the ligand-induced apoptosis.

In various embodiments, the invention encompasses methods of treatment that provide better therapeutic profiles than FasL gene therapy alone. Encompassed by the invention are methods wherein the administration of a ceramide analog has additive potency or additive therapeutic effect. The invention also encompasses synergistic outcomes where the therapeutic efficacy is greater than additive.

Without being bound by any theory or mechanism, the administration of a ceramide analog to a subject sensitize tumor cells that become resistant to Fas-mediated apoptosis. The apoptotic vesicles formed kill adjacent cells that are susceptible to Fas signalling thereby amplifying the bystander effect to a much broader scale. Furthermore, the apoptotic vesicles can destroy blood vessel endothelium that provides blood flow to the tumor. This restricts blood flow to the tumor and accelerates its demise.

In a specific embodiment, the ceramide analog is administered before the administration of the FasL gene therapy modality. In another specific embodiment, the FasL gene therapy modality is administered before the administration of the ceramide analog.

As used herein, FasL gene therapy encompasses any method whereby a nucleic acid encoding a Fas ligand (FasL) or a functional equivalent thereof is expressed in a tumor cell, thereby producing FasL or its functional equivalent which interacts with a Fas+ tumor cell, and causes the Fas+ tumor cell to undergo apoptosis, thereby killing the Fas+ tumor cell. The term FasL as used herein encompasses fragments, variants, mutants derivatives and analogs of the Fas ligand which retains at least a detectable level of activity towards Fas receptor, such as inducing a change in the recipient's cell phenotype. Although not necessary, it is preferred that the Fas ligand is from the species that is receiving the treatment, e.g., human Fas ligand. In one embodiment, the invention comprising using a virus vector to deliver the nucleic acid encoding FasL. Preferably, the virus construct is based on an adenoviral vector, such as but not limited to Ad/FasL-GFPTET and its variations described in PCT publications WO 0027883 and WO 0222175, which are incorporated herein by reference in its entirety.

One skilled in the art will appreciate that there are numerous techniques available by which one can obtain a nucleic acid encoding a Fas ligand, and introducing the nucleic acid into a cell. Provided below are non-limiting examples of various approaches of FasL gene therapy that can be used in combination with the ceramide analogs of the invention.

5.5.1 Fas Ligand Gene Therapy

In various embodiments of the present invention, the nucleic acid encoding the Fas ligand can also encode another protein such as a regulatory protein, which may be used to regulate the expression of the Fas ligand. For example, the regulatory protein can cause the tissue-specific localization of the Fas ligand on the cell membrane, or alternatively cause the premature turn-over of the Fas ligand in non-target cells, or regulate the expression of the FasL via regulation of transcription and/or translation. The regulatory protein can also be encoded by another nucleic acid that is delivered to the cell, either concurrently or consecutively with the nucleic acid encoding the protein to be expressed. In this embodiment, the two nucleic acids can have different sequences, such as different promoters, such that they can be independently regulated, such as by the administration of a drug that selectively regulates the expression of one or both of the promoters, such as by the use of a steroid hormone, e.g., a glucocorticoid hormone that can regulate a promoter that is inducible by that hormone.

The nucleic acid encoding a Fas ligand can also comprise a fusion protein. One skilled in the art will recognize that fusion proteins are routinely used for such purposes as localization of the protein, activation or deactivation of the protein, monitoring the location of the protein, isolation of the protein, and quantitating the amount of the protein. In one embodiment, the fusion protein comprises a Fas ligand and a green fluorescent protein. Other examples of fusion proteins that comprise the Fas ligand include the GFP gene, the CAT gene, the neo gene, the hygromycin gene, and so forth.

The nucleic acid encoding a Fas ligand can also contain a sequence that is capable of regulating the expression of the Fas ligand. In a preferred embodiment, expression of FasL protein is under the control of tetracycline-regulated gene expression system, wherein expression of FasL is controlled by a tet-responsive element, wherein FasL expression requires the interaction of the tetresponsive element and a tet transactivator. In a more preferred embodiment, tight control of FasL expression is achieved using an adenoviral vector in which the tet-responsive element and the transactivator element are built into the opposite ends of the same vector to avoid enhancer interference. Expression can be conveniently regulated by tetracycline or any derivative thereof, which includes, but is not limited to, doxycycline, in a dose-dependent manner. The vector efficiently delivers FasL-GFP gene to cells in vitro, and the expression level of the fusion protein may be modulated by the concentration of doxycycline in culture media.

The FasL gene therapy method described herein comprise introducing into a cell a nucleic acid encoding a Fas ligand. One skilled in the art will recognize that this aspect of the methods can comprise either a stable or a transient introduction of the nucleic acid construct into the cell. Additionally, the stably or the transiently introduced nucleic acid may or may not become integrated into the genome of the host. One skilled in the art will also recognize that the precise procedure for introducing the nucleic acid into the cell may, of course, vary and may depend on the specific type or identity of the cell. Examples of methods for introducing a nucleic acid into a cell include, but are not limited to electroporation, cell fusion, DEAE-dextran mediated transfection, calcium phosphate-mediated transfection, infection with a viral vector, microinjection, lipofectin-mediated transfection, liposome delivery, and particle bombardment techniques, including various procedures for "naked DNA" delivery. The cell into which a nucleic acid encoding FasL is introduced can be a Fas-expressing cell or a cell not expressing Fas.

In one embodiment of the present invention, the promoter is a tissue-specific promoter which one skilled in the art will appreciate can confer tissue-specificity to the expression of the nucleic acid encoding the FasL. For example, the tissue-specific promoter may be a prostate-specific, a breast tissue-specific, a colon tissue-specific, a brain-specific, a kidney-specific, a liver-specific, a bladder-specific, a lung-specific, a thyroid-specific a stomach-specific, a ovary-specific, or a cervix-specific promoter. Where the tissue-specific promoter is a prostate-specific promoter, the promoter includes, but is not limited to the PSA promoter and its mutant ΔPSA, the APSA promoter, the ARR2PB promoter, the PB promoters, the gp91-phox gene promoter, and prostate-specific kallikrein (hLKL2) promoter. Where the tissue-specific promoter is a breast-specific promoter, the promoter includes, but is not limited to MMTV and whey acidic protein promoters. Furthermore, one of ordinary skill will readily know how to identify a promoter specific to a particular cell type. For example, by comparing the differential expression of genes in different tissue types, e.g., using gene chip technology, one can identify genes expressed only in one particular tissue type. These genes can then be isolated and sequenced, and their promoters may be isolated and tested in an animal model for the ability to drive tissue specific expression of a heterologous gene. Such methods are well within the ability of the one of ordinary skill in the art.

The tissue-specificity can also be achieved by selecting a vector that has a high degree of tissue specificity. For example, a vector that selectively infects mucosal cells, such as those associated with colon cancer, can be chosen, and then optionally, used in combination with a specific delivery means, such as by the use of a suppository, to selectively deliver the nucleic acid encoding FasL to those desired cells.

One skilled in the art will recognize that various vectors have more or less applicability depending on the particular host. One example of a particular technique for introducing nucleic acids into a particular host is the use of retroviral vector systems which can package a recombinant retroviral genome. See g., Pastan et al. "A retrovirus carrying an MDR1 cDNA confers multidrug resistance and polarized expression of P-glycoprotein in MDCK cells." Proc. Nat. Acad. Sci. 85: 4486 (1988) and Miller et al. "Redesign of retrovirus packaging cell lines to avoid recombination leading to helper virus production." Mol. Cell. Biol. 6: 2895 (1986)). The produced recombinant retrovirus can then be used to infect and thereby deliver to the infected cells a nucleic acid sequence encoding a Fas ligand. The exact method of introducing the nucleic acid into mammalian cells is, of course, not limited to the use of retroviral vectors. Other techniques are widely available for this procedure including the use of adenoviral vectors (Mitani et al. "Transduction of human bone marrow by adenoviral vector." Human Gene Therapy 5: 941-948 (1994)), adenoassociated viral vectors (Goodman et al. "Recombinant adenoassociated virus-mediated gene transfer into hematopoietic progenitor cells." Blood 84: 1492-1500 (1994)), lentiviral vectors (Naidini et al. "In vivo gene delivery and stable transduction of nondividing cells by a lentiviral vector." Science 272: 263-267 (1996)), pseudotyped retroviral vectors (Agrawal et al. "Cell-cycle kinetics and VSV-G pseudotyped retrovirus mediated gene transfer in blood-derived CD34+ cells. "Exp. Hematol. 24: 738-747 (1996)), vaccinia vectors, and physical transfection techniques (Schwarzenberger et al. "Targeted gene transfer to human hematopoietic progenitor cell lines through the c-kit receptor." Blood 87: 472-478 (1996)). This invention can be used in conjunction with any of these or other commonly used gene transfer methods. In a preferred embodiment of the present invention, the specific vector for delivering the nucleic acid encoding a Fas ligand comprises an adenovirus vector.

Because it is desirable to be able to regulate expression of FasL or a FasL fusion, the present invention also provides use of a vector that provides regulatable expression of FasL or a FasL fusion, comprising a nucleic acid encoding FasL or a FasL fusion operatively linked to a transcription regulatory sequence.

In one embodiment, the transcription regulatory sequence may be inducible, i.e., expression of FasL or a FasL fusion will not proceed unless the appropriate activator for the particular transcription regulatory sequence is present. In another embodiment, the transcription regulatory sequence may be repressible, i.e., expression of FasL or a FasL fusion will proceed unless the appropriate repressor for the particular transcription regulatory sequence is present.

In yet another embodiment, the vector may additionally comprise a nucleic acid encoding a trans-acting factor which interacts with the transcription regulatory sequence to affect transcription of FasL or a FasL fusion. Where the transcription regulatory sequence is inducible, the trans-acting factor will be an activator. Where the transcription regulatory sequence is repressible, the trans-acting factor will be a repressor.

In a more preferred embodiment, the transcription regulatory sequence is a tet responsive element (TRE), and the trans-acting factor is a tet-responsive transacting expression element (tTA). In the most preferred embodiment, the invention utilizes the vector Ad/FasL-GFPTET. This is a replication-deficient adenoviral vector that expresses a fusion of murine FasL and green fluorescent protein (GFP). FasL-GFP retains full activity of wild-type FasL, at the same time allowing for easy visualization and quantification in both living and fixed cells. The fusion protein is under the control of tetracycline-regulated gene expression system. A tight control is achieved by creating this novel "double recombinant" Ad vector, in which the tet-responsive element and the transactivator element are built into the opposite ends of the same vector to avoid enhancer interference. Expression can be conveniently regulated by tetracycline or any derivative thereof, which includes, but is not limited to, doxycycline, in a dose dependent manner. The vector efficiently delivers FasL-GFP gene to cells in vivo and in vitro, and the expression level of the fusion protein may be modulated by the concentration of doxycycline added to the culture media or administered to the subject.

In a preferred embodiment, the vector is a viral vector. In a more preferred embodiment, the viral vector is an adenovirus vector, and the nucleic acid encoding the transactivator protein and the nucleic acid encoding the regulatory element are oriented at opposite ends of the vector.

In various embodiments, if a particular cell type in vivo is to be targeted, for example, by regional perfusion of an organ or tumor, cells from the target tissue can be biopsied and optimal dosages for import of the complex into that tissue can be determined in vitro, as described herein and as known in the art, to optimize the in vivo dosage, including concentration and time length. Alternatively, culture cells of the same cell type can also be used to optimize the dosage for the target cells in vivo. For example, intratumoral injection amounts and rates can be controlled using a controllable pump, such as a computer controlled pump or a micro-thermal pump, to control the rate and distribution of the nucleic acid or vector in the tumor or tissue. One of ordinary skill will readily know how to extrapolate these figures to determine effective human dosages.

For either ex vivo or in vivo use, the nucleic acid, vector, or composition can be administered at any effective concentration. An effective concentration is that amount that results in killing, reduction, inhibition, or prevention of a transformed phenotype of the cells.

The nucleic acid or vector can be administered in a composition. For example, the composition can comprise other medicinal agents, pharmaceutical agents, carriers, adjuvants, diluents, etc. Furthermore, the composition can comprise, in addition to the nucleic acid or vector, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a nucleic acid or a vector and a cationic liposome can be administered to the blood afferent to a target organ or inhaled into the respiratory tract to target cells of the respiratory tract. Regarding liposomes, see, e.g., Brigham et al. Am. J. Resp. Cell. Mol. Biol. 1: 95-100 (1989); Felgner et al. Proc. Natl. Acad. Sci. USA 84: 7413-7417 (1987); U.S. Pat. No. 4,897,355. Furthermore, the nucleic acid or a vector can be administered as a component of a microcapsule that can be targeted to specific cell types, such as macrophages, or where the diffusion of the compound or delivery of the compound from the microcapsule is designed for a specific rate or dosage.

The disclosures of PCT publications WO 0027883 and WO 0222175 are incorporated by reference in its entireties.

6. EXAMPLES

6.1 Example

Preparation LCL-102

(1R,2R)-2-N-Tetradecylamino-1-(4-nitro-phenyl)-1,3-propandiol (LCL-102)

The lipiphilic amine LCL-102 was prepared from D-(−)-threo-2-amino-1-(4-nitro-phenyl)-1,3-propanediol A by reductive amination with tetradecyl aldehyde in the presence of NaBH3CN.

The aldehyde B (0.74 g, 3.5 mmol) in methanol (10 mL) and acetic acid (11.0 mL) was added dropwise to a well-stirred mixture of the amine A (0.94 g, 4.4 mmol) followed by a portion-wise addition of sodium cyanoborohydride (300 mg, 4.77 mmol) over 5 min at room temperature. After the addition was completed the reaction mixture was stirred for an additional 30 min at room temperature. The reaction mixture was concentrated under reduced pressure. The resultant residue was dried under reduced pressure, and the resultant crude material was purified by flash column chromatography using chloroform-methanol-conc. ammonium hydroxide (5:1:0.1; v/v/v/) to provide 854 mg (62%) of pure LCL-102 as a white solid (Rf=0.35, CHCl3:MeOH, 5:1,v/v).

6.2 Example 2

Preparation LCL-204

1M HCl in diethyl ether (2.5 ml) was added dropwise at +4° C. to a well-stirred solution of LCL-102 (250 mg) in ethyl acetate (5.0 ml). The mixture was stirred at 25° C. for 5 min. The mixture concentrated under reduced pressure, and the resultant residue was recrystallized from ethyl acetate-n-hexane (1:1 v:v) to provide 0.175 mg (64%) of LCL-204 as a white powder.

6.3 Example 3

Preparation of LCL120

D-eryhtro-2-N-[[16'-(1"-Pyridinium)hexadecanoyl] amino]-1-phenyl-1-propanol Bromide (LCL120)

(A). Synthesis of D-eryhtro-2-N-[(16'-Bromohexadecanoyl)amino]-1-phenyl-1-propanol; corresponding bromo analog B). To a well-stirred mixture of D-eryhtro-2-amino-1-phenyl-1-propanol (175 mg, 1.15 mmol), 50% aqueous solution of sodium acetate (15 ml) and THF (20 mL) a solution of a freshly prepared 16-bromohexadecanoyl chloride (0.61 g) in dry THF (6.0 mL) was added dropwise over 1 min. After the addition was completed, the reaction mixture was stirred for an additional 25 min at room temperature. The organic layer was separated and the aqueous phase was extracted with ethyl acetate (2×15 mL). The combined organic extracts were dried (MgSO$_4$), filtered, and evaporated to dryness under reduced pressure to give crude product. This material was purified by flash column chromatography (CHCl$_3$:MeOH:conc. NH4OH, 10:1:0.05, v/v/v) to give a pure corresponding bromo analog B (428 mg, 79% yield) as a white powder. An analytical sample of this bromide was obtained by recrystallization from n-hexane-ethyl acetate (3:1, v/v) to give a white microcrystalline powder, mp 77-78.5° C.; TLC R$_f$ (CHCl$_3$—MeOH, 8:1, v/v) R$_f$ 0.68. [α]$^{22}_D$=+13.4° (c=1, MeOH); [α]$^{22}_{365}$=+37.8° (c=1, MeOH).

(B). Cationization of D-eryhtro-2-N-[(16'-Bromohexadecanoyl)amino]-1-phenyl-1-propanol. A mixture of D-eryhtro-2-N-[(16'-Bromohexadecanoyl)amino]-1-phenyl-1-propanol (220 mg, 0.47 mmol), anhydrous pyridine (2 mL) and anhydrous toluene (4 mL) was heated in a closed glass test-tube in an oil bath at 75-85° C. over 6 hrs. The reaction mixture was cooled to room temperature and evaporated under reduced pressure to dryness following drying of the residue in a high vacuum for 6 hrs. The afforded oily residue was washed twice with ethyl acetate-n-hexane (4:1, v/v/, 3×10 mL). The obtained crude product was dissolved in distilled water (10 mL) and extracted with dichloromethane (2×4.0 mL). The organic fractions were extracted back with water (2×4 mL) and all the aqueous fractions were combined and evaporated under reduced pressure. The obtained residue was lyophilized in a high vacuum to give a pure LCL120 as a colorless oil (210 mg, 81%). The analytical sample of LCL120 was prepared by recrystallization from anhydrous acetone-ethanol (8:1,v/v) to give a colorless semi-solid. TLC (CHCl$_3$—(CH$_3$)$_2$CO—MeOH—CH$_3$COOH—H$_2$O, 20:8:8:2:1, v/v) R$_f$ 0.49; [α]$^{21}_D$=+9.1° (c=1, MeOH); [c]$^{21}_{365}$=+30.4° (c=1, MeOH); $^1$H NMR (500 MHz, MeOD) δ 9.00 (d, 2H, J=5.6, 2,5-H$_{Py}$) 8.59 (t, 1H, J=7.9, 4-H$_{Py}$), 8.11 (t, 2H, J=7.0, 3,5-H$_{Py}$), 7.36 (m, 2H, ArH), 7.28 (m, 2H, ArH), 7.21 (m, 1H, ArH), 4.62 (m, 3H, 1-H and C(16)H$_2$-pyridinium ring), 4.12 (m, 1H, 2-H), 2.07 (m, 2H, COCH$_2$), 2.01 (m, 2H, C(15)H$_2$C(16)H$_2$-pyridinium ring), 1.45(m, 2H, COCH$_2$CH$_2$), 1.38 (m, 2H, C(14)H$_2$C(15)H$_2$C(16)H$_2$-pyridinium ring), 1.25 (m, 20H, CH$_2$), 1.08 (d, 3H, J=6.8, CH$_3$); ESI-MS (CH$_3$OH, relative intensity, %) m/z 467.3 (M$^+$, 100). Calcd. for [C$_{30}$H$_{47}$N$_2$O$_2$]$^+$ m/z 467.36.

6.4 Example 4

Preparation of LCL85

D-threo-2-N-[[16'-(1'''-Pyridinium)hexadecanoyl]amino]-1-(4'''-nitrophenyl)-1,3-propandiol Bromide (LCL85)

(A). Synthesis of D-threo-2-N-[(16'-Bromohexadecanoyl)amino]-1-(4'''-nitrophenyl)-1,3-propandiol; corresponding bromo analog B). To a well-stirred mixture of D-threo-2-amino-1-(4-nitrophenyl)-1,3-propandiol (244 mg, 1.15 mmol), 50% aqueous solution of sodium acetate (15 ml) and THF (20 mL) a solution of a freshly prepared 16-bromohexadecanoyl chloride (0.61 g) in dry THF (6.0 mL) was added dropwise over 1 min. After the addition was completed, the reaction mixture was stirred for an additional 25 min at room temperature. The organic layer was separated and the aqueous phase was extracted with ethyl acetate (2×15 mL). The combined organic extracts were dried (MgSO$_4$), filtered, and evaporated to dryness under reduced pressure to give crude product. This material was purified by flash column chromatography (CHCl3:MeOH:conc. NH$_4$OH, 10:1:0.05, v/v/v) to give a pure corresponding bromo analog B (457 mg, 75% yield) as a pale yellow powder. An analytical sample of this bromide was obtained by recrystallization from n-hexane-ethyl acetate (2:1, v/v) to give a white microcrystalline powder, mp 79-81° C.; TLC R$_f$(CHCl$_3$-MeOH, 8:1, v/v) R$_f$ 0.38. [α]$^{20}_D$=−1.90° (c=1, MeOH).

(B). Cationization of D-threo-2-N-[(16'-Bromohexadecanoyl)amino]-1-(4'''-nitrophenyl)-1,3-propandiol; A mixture of D-threo-2-N-[(16'-Bromohexadecanoyl)amino]-1-(4'''-nitrophenyl)-1,3-propandiol (265 mg, 0.50 mmol), anhydrous pyridine (2 mL) and anhydrous toluene (4 mL) was heated in a closed glass test-tube in an oil bath at 75-85° C. over 6 hrs. The reaction mixture was cooled to room temperature and evaporated under reduced pressure to dryness following drying of the residue in a high vacuum for 6 hrs. The afforded oily residue was washed twice with ethyl acetate-n-hexane (4:1, v/v/, 3×10 mL). The obtained crude product was dissolved in distilled water (10 mL) and extracted with dichloromethane (2×4.0 mL). The organic fractions were extracted back with water (2×4 mL) and all the aqueous fractions were combined and evaporated under reduced pressure. The obtained residue was lyophilized in a high vacuum to give a pure LCL85 as a pale yellow semi-solid (220 mg, 75% yield). The analytical sample of LCL85 was prepared by recrystallization from anhydrous acetone-ethyl acetate (8:1,v/v) to give a pale yellow microcrystalline powder, mp 52-53.5° C. TLC (CHCl$_3$—(CH$_3$)$_2$CO—MeOH—CH$_3$COOH—H$_2$O, 20:8:8:2:1, v/v) R$_f$ 0.45; $^1$H NMR (500 MHz, MeOD) δ 9.00 (dd, 2H, J=6.6, 1.2, 2,5-H$_{Py}$) 8.59 (t, 1H, J=7.8, 4-H$_{Py}$), 8.16 (d, 2H, J=8.9, ArH), 8.11 (t, 2H, J=7.2, 3,5-H$_{Py}$), 7.63 (d, 2H, J=8.9, ArH), 5.13 (m, 1H, 1-H), 4.63 (t, 2H, J=7.7, C(16)H$_2$-pyridinium ring), 4.18 (m, 1H, 2-H), 3.76 (dd, 1H, J=10.7, 7.6, 1-Ha), 3.56 (dd, 1H, J=10.7, 6.0, 1-Hb), 2.07 (m, 2H, COCH$_2$), 2.01 (m, 2H, C(15)H$_2$C(16)H$_2$-pyridinium ring), 1.1-1.40(m, 22H, COCH$_2$CH$_2$), 1C(14)H$_2$C(15)H$_2$C(16)H$_2$-pyridinium ring and CH$_2$), 1.0 (m, 2H, CH$_2$); ESI-MS (CH$_3$OH, relative intensity, %) m/z 528.5 (M$^+$, 100). Calcd. for [C$_{30}$H$_6$N$_3$O$_5$]$^+$ m/z 528.34.

6.5 Example 5

Preparation of LCL16, 17, 204, 284, 289 and 385

Lipophilic amine hydrochlorides: LCL204, 284, 286 and 385 were prepared by the reductive amination of tetradecyl aldehyde with aminoalcohols, following the transformation of the formed C14-alkyl amines to the corresponding hydrochloride salts.

(1R,2R) D-threo-2-N-Tetradecylamino-1-(4'-nitrophenyl)-1,3-propandiol hydrochloride (LCL204). To a well-stirred mixture of D-threo-2-amino-1-(4-nitro-phenyl)-1,3-propanediol (940 mg, 4.4 mmol) and the tetradecyl aldehyde (740 mg, 3.5 mmol) in methanol (15 mL) acetic acid (11.0 mL) was added dropwise following a portionwise addition of sodium cyanoborohydride (300 mg, 4.77 mmol) over 5 min at room temperature. After the addition was completed, the reaction mixture was stirred for an additional 30 min at room temperature. The reaction mixture was evaporated under a reduced pressure to dryness and the obtained residue was dried under high vacuum (~1 torr at rt over 6 hr). The crude material was purified by flash column chromatography using chloroform-methanol-conc. ammonium hydroxide (5:1:0.1; v/v/v/) to give 854 mg (62% yield) of pure free base of LCL204 as a white solid ($R_f$=0.35, $CHCl_3$:MeOH, 5:1, v/v). This material was dissolved in ethyl acetate (15 mL) and 1M HCl solution in dry diethyl ether (7.0 mL) was added dropwise at +4° C. The reaction mixture was stirred at room temperature for an additional 10 min. The mixture was evaporated under reduced pressure to dryness and the afforded residue was dried in a high vacuum for 2 hrs at room temperature. This material was recrystallized from ethyl acetate-n-hexane (1:1, v/v) to give pure LCL204 (0.675 mg, 72% yield) as a white microcrystalline powder, mp 101-103° C., $[\alpha]^{20}_D$=−30.5° (c=1, MeOH); $^1$H NMR (500 MHz, MeOD) δ 8.28 (d, 2H, J=8.8, ArH), 7.72 (d, 2H, J=8.8, ArH), 5.02 (d, 1H, J=9.2, 1-H), 3.67 (dd, 1H, J=12.5, 3.4, 1-Ha), 3.38 (dd, 1H, J=12.5, 4.1, 1-Hb), 3.34 (m, 1H, 2-H), 3.15 (m, 2H, NHCH$_2$), 1.73 (m, 2H, NHCH$_2$CH$_2$), 1.30 (m, 22H, CH$_2$), 0.89 (t, 3H, J=7.1, CH$_3$); ESI-MS (CH$_3$OH, relative intensity, %) m/z 409.5 (MH$^+$, 100), 391 ([MH-H$_2$O]$^+$, 10). Calcd for C$_{23}$H$_{41}$N$_2$O$_4$ m/z 409.31. Anal. Calcd. for C$_{23}$H$_{41}$ClN$_2$O$_4$ (445.0); C, 62.07; H, 9.29; N, 6.29; Cl, 7.97. Found: C, 61.29; H, 9.22; N, 6.21; Cl, 7.86.

(1R,2R) D-threo-2-N-Tetradecylamino-1-phenyl-1,3-propandiol hydrochloride (LCL385). This compound was prepared from D-threo-2-amino-1-phenyl-1,3-propanediol and tetradecyl aldehyde following procedure for the preparation of LCL204. Yield: 1.03 g (59%). Analytical sample of LCL385 was obtained by crystallization from n-hexane-ethyl acetate (4:2, v/v/) as a white powder, mp>170 (with decomp.); $[\alpha]^{21}_D$=−40.0° (c=1, MeOH). $^1$H NMR (500 MHz, CDCl$_3$) δ7.38 (d, 1H, J=6.8, NH), 7.30 (m, 5H, ArH), 5.13 (d, 1H, J=9.4, 1-H), 3.73 (dd, 1H, J=13.4, 2.3, 1-Ha), 3.53 (dd, 1H, J=13.4, 4.7, 1-Hb), 3.16 (m, 1H, 2-H), 3.08 (m, 2H, NHCH$_2$), 1.85 (m, 2H, NHCH$_2$CH$_2$), 1.30 (m, 2H, NHCH$_2$CH$_2$CH), 1.20 (m, 20H, CH$_2$), 0.82 (t, 3H, J=7.1, CH$_3$); ESI-MS (CH$_3$OH, relative intensity, %) m/z 400.3 (MH$^+$, 100). Calcd. for C$_{23}$H$_{42}$NO$_2$ m/z 399.29.

(1S,2R) D-erythro-2-N-Tetradecylamino-1-phenyl-1-propanol hydrochloride (LCL284). This compound was prepared from D-erythro-2-amino-1-phenyl-1-propanol and tetradecyl aldehyde following procedure for the preparation of LCL204 LCL204. Yield: 1.0 g (64%). Analytical sample of LCL284 was obtained by crystallization from anhydrous ethyl acetate as a white powder, mp>177° C. (with decomp.); $[\alpha]^{20}_D$=+14.5° (c=1, MeOH) and −16.7° (c=1, CHCl$_3$); $[\alpha]^{20}_{365}$=+41.2° (c=1, MeOH) and −58.0° (c=1, CHCl$_3$); $^1$H NMR (500 MHz, MeOD) δ•7.40 (m, 4H, 2,3,5,6-ArH), 7.38 (m, 1H, 4-ArH), 5.13 (d, 1H, J=3.0, 1-H), 3.46 (ddd, 1H, J=3.0, 6.7, 13.5, 2-H), 3.09 (t, 2H, J=4.3, NHCH$_2$), 1.74 (m, 2H, NHCH$_2$CH$_2$), 1.30 (m, 22H, CH$_2$), 1.05 (d, 3H, J=6.8, CHCH$_3$) 0.89 (t, 3H, J=7.1, CH$_3$); ESI-MS (CH$_3$OH, relative intensity, %) m/z 349.3 (MH$^+$, 100). Calcd. for C$_{23}$H$_{42}$NO m/z 348.33. Anal. Calcd for C$_{23}$H$_{42}$ClNO (384.04): C, 71.93; H, 11.02; N, 3.65; Cl 9.23. Found: C, 71.77; H, 11.08; N, 3.69; Cl, 9.53.

(1R,2S) L-erythro-2-N-Tetradecylamino-1-phenyl-1-propanol hydrochloride (LCL289). This compound was prepared from L-erythro-2-amino-1-phenyl-1-propanol and tetradecyl aldehyde following procedure for the preparation of LCL284. Yield: 1.05 mg (65%). $[\alpha]^{20}_D$=−13.3° (c=1, MeOH) and +16.0° (c=1, CHCl$_3$); $[\alpha]^{20}_{365}$=−40.5° (c=1, MeOH) and +59.00 (c=1, CHCl$_3$). Remaining analytical data are identical as reported for LCL284.

(1S,2R) D-erythro-N-[2-(1-hydroxy-1-phenyl)propane]-N'-dodecane-urea (LCL16). To a solution of D-erythro-2-amino-1-phenyl-1-propanol (460 mg, 3.0 mmol) in anhydrous tetrahydrofuran (12 mL) and anhydrous ethanol (11.0 mL), dodecyl isocyante (49.2 mg, 0.181 mmol) was added drop-wise over 1 min. After the addition was completed, the mixture was stirred under nitrogen at room temperature for 4 hrs. Solvents were evaporated under a reduced pressure to dryness and the residue was dried in a high vacuum at room temperature for 2 hrs. This material was purified by a gradient flash column chromatography (silica gel 60, ethyl acetate-n-hexane (6:1, v/v)/pure ethyl acetate) following recrystallization from n-hexane-diethyl ether to give a pure LCL16 (800 mg, 73% yield) as a white microcrystalline needles, mp 68.5-70° C.; TLC: $R_f$(CHCl$_3$-MeOH, 5:1, v/v) $R_f$ 0.36; $[\alpha]^{20}_D$=+12.0° (c=1, MeOH); $[\alpha]^{20}_{365}$=+25.4° (c=1, MeOH); $^1$H NMR (500 MHz, CDCl$_3$) δ•7.25 (m, 4H, 2,3,5,6-ArH), 7.20 (m, 1H, 4-ArH), 4.71 (d, 1H, J=1.3, 1-H), 4.12 (m, 1H, 2-H), 3.06 (m, 2H, NHCH$_2$), 1.41 (m, 2H, NHCH$_2$CH$_2$), 1.19 (m, 22H, CH$_2$), 0.93 (d, 3H, J=6.8, CHCH$_3$) 0.81 (t, 3H, J=7.0, CH$_3$); ESI-MS (CH$_3$OH, relative intensity, %) m/z 363.2 (MH$^+$, 20), 345.2 ([MH—H$_2$O]$^+$, 100). Calcd for C$_{22}$H$_{39}$N$_2$O$_2$ m/z 363.29.

(1R,2S) L-erythro-N-[2-(1-hydroxy-1-phenyl)propane]-N'-dodecane-urea (LCL17). This compound was prepared from L-erythro-2-amino-1-phenyl-1-propanol and dodecyl isocyanate following procedure for the preparation of LCL16. Yield: 822 mg (75%). $[\alpha]^{21}_D$=−11.5° (c=1, MeOH); $[\alpha]^{21}_{365}$=−27.5° (c=1, MeOH). The remaining analytical data are identical as reported for LCL16.

7. Properties of Ceramide Analogs

In this example, it is shown that treating prostate cancer cells with the lysosomotropic ceramide analog, LCL204, results in rapid destabilization of the lysosomes as early as 5 minutes after treatment. A rise in ceramide levels was detected in the same time frame. This was closely followed by the specific degradation of key ceramide metabolizing proteins by a lysosomal protease and the release of lysosomal proteases into the cytosol. The preceding events act concert to elevate p53 and p73 in a cell line-dependent manner, which were followed by up-regulation and activation of Bak. The increase in p73 and Bak proteins depended on p38 MAPK and JNK/AP-1 activities, respectively. Combined, these events resulted in mitochondria depolarization and executioner caspase activation, ultimately ending in apoptosis. In conclusion, LCL204 is essential for the lysosomotropic activities it displays. These results provide evidence that targeting both the lysosomes and ceramide signaling pathways with molecules such as LCL204 serve as a treatment for cancer.

7.1 Materials and Methods

Cell lines. The human PCa cell lines DU145, LNCaP, DuPro, and PC-3 were purchased from ATCC (Manassas, Va., USA), and PPC-1 cells were from Dr. Yi Lu at the University of Tennessee (Memphis, Tenn.). All cells were cultured in RPMI 1640 (Mediatech Inc.; Herndon, Va., USA) supplemented with 10% heat-inactivated BGS (Hyclone; Logan, Utah, USA). Cells were maintained in 5% CO$_2$ at 37° C. All experiments were performed in RPMI 1640 supplemented with 2% heat-inactivated BGS.

Reagents. LCL204(1R,2R) 2-(N-tetradecylamino)-1-(4-NO$_2$)-phenyl-1,3-dihydroxy-propane HCl was synthesized in the Medical University of South Carolina Lipidomics Core Facility (Charleston, S.C.) by reductive amination of (1R,2R) 2-amino-1-(4-NO$_2$)-phenyl-1,3-dihydroxy-propane as described (24). Full synthesis and physico-chemical characterization of LCL204 will be shown somewhere else (Szulc/Bielawska, novel ceramide modulators. Synthesis and biological characterization of D-Mapp analogs, in preparation to Bioorganic & medicinal Chemistry). Pepstatin A, leupeptin, aprotinin, phenylmethanesulfonyl fluoride (PMSF), and MG132 were all purchased from Sigma (St. Louis, Mo., USA). CA074Me was from Calbiochem (San Diego, Calif., USA), zVAD-fmk, SP600125, and SB-203580 were from Biomol (Plymouth Meeting, Pa., USA). JC-1 mitochondrial dye and LysoTracker Red lysosomal dye were from Molecular Probes (Eugene, Oreg., USA). Antibodies used for immunoblotting were: mouse monoclonal anti-cytochrome c, anti-acid ceramidase, anti-LAMP-1, and anti-p73 (Pharmingen; San Diego, Calif., USA), rabbit polyclonal anti-actin (Sigma), mouse monoclonal anti-Phospho-JNK, anti-JNK, rabbit polyclonal anti-p38MAPK (Santa Cruz Biotechnology; Santa Cruz, Calif., USA), mouse monoclonal anti-cathepsin B and anti-c-Jun (Oncogene Research Products; San Diego, Calif., USA), mouse monoclonal anti-COX IV (Molecular Probes), rabbit polyclonal anti-Bak, Bax, p53, PUMA, Phospho-p38MAP-K (Cell Signaling Technology Inc., Beverly Mass.), goat anti-rabbit IgG-HRP conjugate (Santa Cruz) and goat anti-mouse IgG-HRP conjugate (Sigma).

MTS cytotoxicity assays for LCL204 treatments. Cell viability was determined using the CellTiter 96 AQ$_{ueous}$ One Solution Cell Proliferation Assay (Promega; Madison, Wis., USA). $1 \times 10^4$ cells per well were seeded in 96-well plates overnight. The next day media was removed and replaced with either 100 μl media with vehicle control or media containing LCL204 at desired concentrations. Assays were carried out according to manufacturer's instruction as previously described (60). For experiments using enzyme inhibitors and LCL204, media was removed and replaced with 50 μl media containing vehicle only or indicated inhibitor. Cells were pretreated 1 hour at 37° C. before adding 50 μl media containing vehicle, inhibitor only, LCL204 only (2× concentration), or a combination. The remainder of the assay was carried out as described above.

Ceramide measurement. $2.1 \times 10^6$ cells were seeded in 100 mm plates overnight. The next day, media was removed and replaced with media containing vehicle control or LCL204 (10 μM) for indicated time points. Following treatment, cells were harvested by gentle scraping and immediate centrifugation at 4° C. for 5 minutes at 400×g. Cell pellets were then resuspended in ice cold PBS and stored at −80° C. For sphingolipid analysis, cell pellets were examined using mass spectometry as previously described (61).

Caspase 3/7 Activity Assay. Cells were seeded overnight in clear bottom black 96 well plates (Corning; Acton Mass.). The next day, medium was removed and replaced with medium containing vehicle or LCL204 at indicated concentrations. After 24 hours treatment, Caspases 3 and 7 activities were measured using Apo-ONE Homogeneous Caspase 3/7 assay according to the manufacturer's instructions (Promega). Fluorescence was measured using a Fluostar dual fluorescence/absorbance plate reader (BMG Laboratories; Durham, N.C., USA) with 485 nm excitation and 520 nm emission filter set.

Mitochondria membrane potential measurement. Cells were seeded at a density of $7.49 \times 10^5$ cells per plate in 60 mm plates overnight. The next day, media was replaced with media containing vehicle control or LCL204 (5 μM). Cells were lifted using Cell Stripper (Mediatech), washed twice in PBS, and resuspended in 3 ml 1×JC-1 reagent solution (dissolved in medium). Samples were incubated at 37° C. for 15 minutes, washed twice with PBS, and resuspended in 0.5 ml growth medium before analysis by flow cytometry using a Beckton-Dickinson FACSCalibur (590 nm/527 nm emission). A minimum of 10,000 events were scored for each sample.

Immunoblot analysis. Cells were seeded in 60mm plates as described above and treated accordingly. Cells were lifted by gently scraping the plates, washed once with ice cold PBS and then lysed in lysis buffer (PBS, 1% Triton X-100, 10% glycerol) containing protease inhibitors pepstatin A (0.5 μg/ml), leupeptin (0.5 μg/ml), aprotinin (5 μg/ml), and PMSF (100 μg/ml) for 10 minutes on ice. Insoluble material was removed by centrifugation at 14,000 rpm for 15 minutes at 4° C. The supernatants were then supplemented with SDS at a final concentration of 2% and stored at −80° C. Protein concentrations were determined using the DC Protein Assay (BioRad Laboratories; Hercules, CA, USA) according to the manufacturer's instructions. 50 μg of protein per sample (unless otherwise indicated) were separated on NuPAGE 4-12% Bis-Tris gels (Invitrogen; Carlsbad, CA, USA) and transferred to nitrocellulose membranes (BioRad). Following transfer, membranes were blocked for 1 hour at room temperature in Tris-buffered saline (TBS) containing 0.1% Tween-20 and 5% nonfat dry milk and incubated overnight at 4° C. with primary antibody at a dilution of 1:2,000(actin), 1:1,000(cytochrome c, COX IV, Bax, Bak, p53, p38, P-p38), 1:500(P-JNK, JNK), 1:250 (AC, p73), or 1:400(LAMP-1, cathepsin B). Overnight incubations were performed in 5% milk in TBS-Tween. Following overnight incubation, membranes were washed three times for 10 minutes each in TBS-Tween and incubated for 1 hour at room temperature with secondary antibody in 5% milk TBS-Tween at a dilution 1:5,000 (goat anti-mouse IgG) or 1:50,000 (goat anti-rabbit). Membranes were then washed three times more and incubated for 5 minutes at room temperature with Super Signal HRP substrate (Pierce Biotechnology Inc.; Rockford, IL, USA).

Lysosoinal stability assay. Lysosomal stability was measured using the fluorescent dye LysoTracker Red (LTR). Cells were seeded overnight in 60 mm plates. The next day, medium was removed and replaced with medium containing 200 nM LTR. Cells were loaded with LTR for 30 minutes at 37° C. LTR was removed and cells were washed once with PBS, then medium containing the treatment was added for the indicated time. After treatment, cells were lifted with trypsin, washed once in PBS, and resuspended in 0.5 mL growth medium. LTR fluorescence was measured using FACS analysis (564-606 nm) as above. A decrease in fluorescence intensity corresponded to an increase in lysosomal pH, and a minimum of 10,000 events were scored for each sample.

Reverse Transcriptase PCR. DU145 cells were seeded in 6-well plates as described above. The next day media was gently removed and replaced with media containing 2% BGS and LCL204(10μM) or ethanol control. Cells were collected at indicated time points and total RNA was extracted using RNAqueous-4PCR kit (Ambion Inc.; Austin, TX), including the DNase I treatment step to remove DNA contamination. The level of transcripts of AC was assayed by two-step RT-PCR protocol (Ambion) and Rig/S15 was used as an internal control. The sequence of the primer for amplification of AC is as followed: F---tgtggatagggttcctcactaga, R---ttgtgtatacggt-cagcttgttg 375 bp. All reactions were performed in a programmable thermal cycler (reverse transcription at 55° C. for 1 hour; PCR at 95° C., 3 minutes; 95° C., 30 second; 52° C., 1 minute and extension at 72° C. for 1 minute; final extension at 72° C., 10 minutes). The PCR product was separated on a 2% agarose gel.

Acid Sphingomyelinase Activity Assay. DU145 cells were lysed in 50 mM Tris (pH=7.4) using a probe sonicator. Cellular debris was removed after centrifugation at 3000×g for 10 minutes. Proteins (50 μg) were adjusted to a total volume of 100 μl and the reaction was started by adding 100 μl of the reaction mixture containing 1 mM EDTA, 250 mM sodium acetate (pH 5.0), 100 µM [choline-methyl-$^{14}$C] sphingomyelin and 0.1% Triton X. After incubation at 37° C. for one hour, the reaction was stopped by adding 1.5 ml of chloroform/methanol (2:1) and then 200 µl of water. Phases were separated by centrifugation at 2000×g for 5 minutes. Quantitation of the amount of released radioactive phosphocholine was determined by subjecting 400 µl of the upper phase to scintillation counting.

Subcellular fractionation. For cytochrome c immunoblot, cells were seeded and treated as described above. Cells were harvested at 4, 12, or 24 hours after treatment as described previously (62) and proteins (15 µg) were separated by gel electrophoresis and immunoblotted for cytochrome c as above. The protocol for separating cytosolic and heavy membrane fractions is a modified version of that used by Desahger et al. (63). Briefly, cells were seeded and treated in 60 mm plates as described above. Cells were harvested at 0, 0.5, 1, and 2 hours after treatment, washed once in PBS, and gently resuspended in isotonic mitochondrial buffer (210 mM mannitol, 70 mM sucrose, 1 mM EDTA, 10 mM HEPES, pH 7.0) supplemented with protease inhibitors. Cells were then transferred to 1.5 mL microcentrifuge tubes and homogenized using 40 strokes with a polished (fine grain sandpaper) Teflon pestle. Fractions were separated using differential centrifugation as described in the reference. All fractions were stored at −80° C. Cytosolic and heavy membrane fractions (30 and 15 µg, respectively) were separated on NuPAGE gels and immunoblotted as described above. For cathepsin B activity assays, the same procedure was carried out as above with the exception of protease inhibitors. Enzyme activity per 50 µg lysate was measured using the fluorogenic cathepsin B substrate 111 (Calbiochem) according to the manufacturer's protocol.

Confocal Microscopy and Immunocytochemistry. DU145 cells were grown in 4.3 cm$^2$ chamber slides (Nalge Nunc) and transfected with YFPmito alone or with the dominant-negative inhibitor of Drp1(K38A) (64) using FuGENE6 (Roche; Indianapolis, IN) according to the manufacturer's instructions using 1 µg of total DNA per chamber. 24 hr after transfection and 30 min prior to treatment with 15 µM LCL204, cells were exposed to zVAD-fmk (50 µM). The slides were fixed with 4% paraformaldehyde for 20 min then permeabilized with 0.2% Triton X-100 for 15 min, followed by blocking with 4% bovine serum albumin for 45 min at RT. Cells were probed with rabbit polyclonal 2-14 anti-Bak antibody (1:5000; BioChem) for 2 hr then stained with goat anti-rabbit Alexa Fluor 543 antibodies (1:250; Molecular Probes) for 45 min. After washing, cells were imaged using the 63x objective of an LSM 510 Zeiss confocal microscope.

Stable transfections. Both CMV-TAM67 and pcDNA3 vectors were from Dr. Michael Birrer (National Cancer Institute; Rockville, Md.). PPC-1 cells (7×10$^5$) were transfected with 4 µg of DNA in 60 mm dishes using FuGENE6 according to the manufacturer's instructions. Stably transfected clones were selected in 400 µg/mL G418 (Sigma). TAM67 was detected by Western blot analysis using an antibody for c-Jun (Ab-1, Oncogene) as described above.

7.2 Results

LCL204 induces apoptosis in PCa cells. Using an MTS cell viability assay LCL204 was found to induce concentration-dependent cell death in the micromolar range in five different PCa cell lines cells after 24 hours treatment (FIG. 14A). Caspase activation is considered one of the hallmarks of apoptosis as well as a key event in executing the apoptotic program. Using a fluorogenic caspase activity assay, LCL204 was found to induce dose-dependent executioner caspase activity in DU145 cells after 24 hours treatment (FIG. 14B). Furthermore, cell death was substantially reduced when cells were pre-treated with the broad-spectrum caspase inhibitor, zVAD-fmk, indicating a necessary role for caspases in LCL204-mediated cell death, especially at concentrations lower than 15 µM (FIG. 14C). Apoptosis signaling that stems from within the cell typically traverses the intrinsic (type II) apoptotic pathway with characteristics such as loss of mitochondria membrane potential ($\Delta\Psi m$) and the release of cytochrome c from mitochondria into the cytosol (25). A decrease in $\Delta\Psi m$ was observed as early as 2 hours after treatment with 5 µM LCL204, which continued to decrease over time (FIG. 14D). This is evident in the shift in fluorescence spectra of the JC-1 dye from 527 nm to 590 nm after treatment with LCL204. Cytochrome c release into the cytosol was detected by 4 hours after treatment with 5 or 10 µM LCL204 (FIG. 14E). These data indicate early activation of the intrinsic apoptosis pathway.

LCL204 induces rapid changes in ceramide levels. Ceramide levels following LCL204 treatment was measured. Treating DU145 cells with 10 µM LCL204 induced a rise in total ceramide levels within one hour of treatment (FIG. 15). Ceramide levels remained elevated for another hour before returning to baseline levels. The transient nature of this ceramide elevation was unexpected and will be addressed below.

Figure 16A:
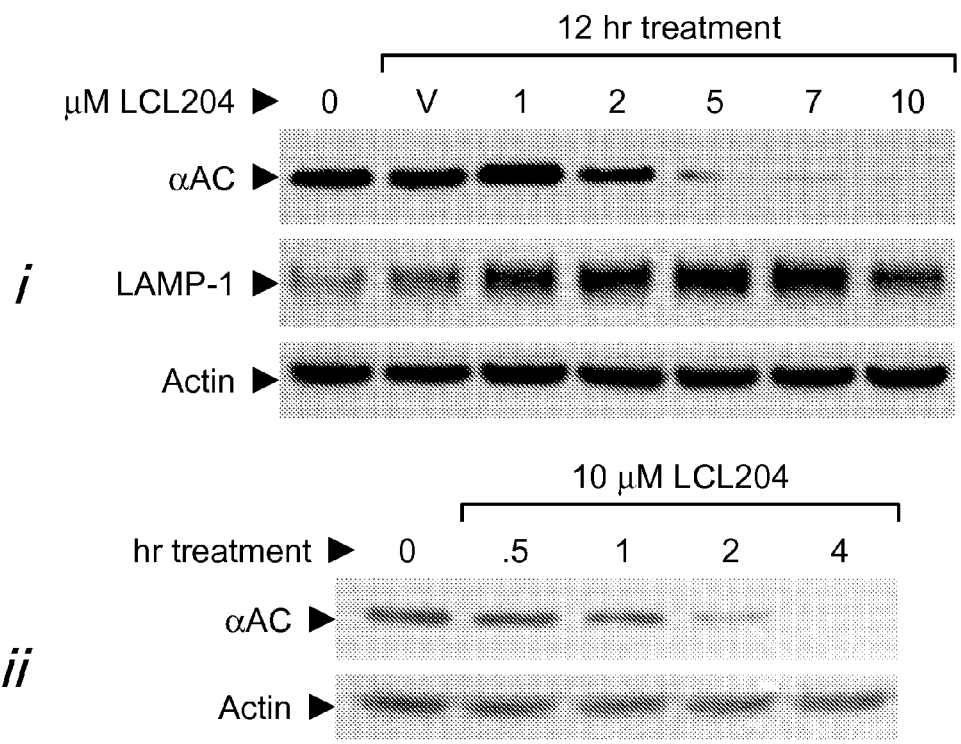
Figure 16B:
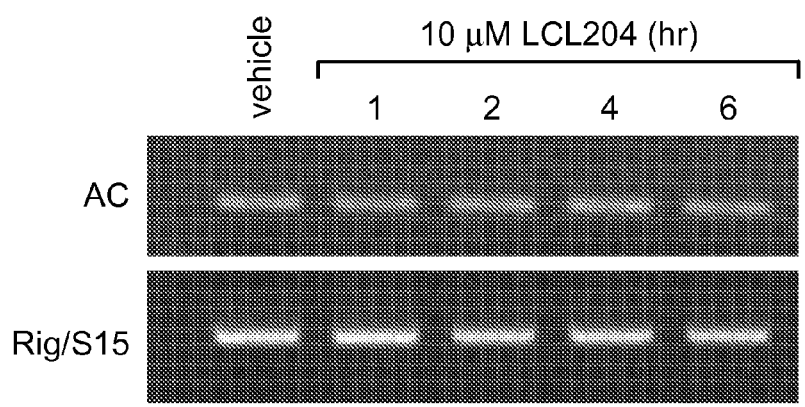

LCL204 Induces Proteolytic Degradation of AC and ASMase. When treating DU145 cells with LCL204, a dose and time-dependent decrease in AC expression levels was detected (FIG. 16A). The loss of AC expression showed dose dependence on LCL204 concentration when cells were treated with the compound for 12 hours (FIG. 16A, i). In the same experiment, expression of the lysosomal membrane protein, LAMP-1, increases as AC levels declined with LCL204 treatment (FIG. 16A, i). Treatment of DU145 cells with 5 µM LCL204 caused down-regulation of AC in a time-dependent manner beginning as early as 2 hours after treatment (FIG. 16A, ii). These effects were comparable in all PCa cell lines tested, including PC-3, LNCaP, DuPro, and PPC-1 (not shown). Using RT-PCR, the down-regulation was not a transcriptional event as there was no decrease in AC mRNA levels in DU145 cells during treatment with 10 µM LCL204 within the same time frame of protein level decline (FIG. 16B). This indicated a post-transcriptional event such as proteolytic degradation. As LAMP-1 expression actually increased with LCL204 treatment concentration, there is a degradation of selective lysosomal enzymes induced by LCL204 treatment.

Figure 16C:
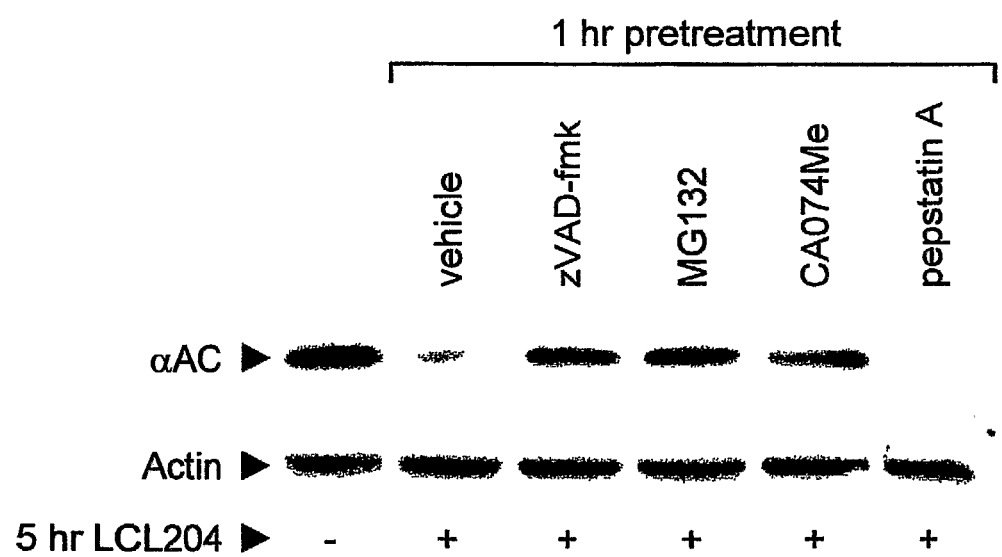

Protein degradation is frequently executed through the proteasomal (Weissman, A. M. Themes and variations on ubiquitylation. Nature Reviews Molecular Cell Biology., 2: 169-178, 2001) or lysosomal (Kornfeld, S. and Mellman, I. The biogenesis of lysosomes. Annual Review of Cell Biology., 5: 483-525, 1989) pathways. Alternatively, caspases can serve as degradative tools (Thornberry, N. A. and Lazebnik, Y. Caspases: enemies within. Science., 281: 1312-1316, 1998). Therefore, the effects of LCL204 in the presence of a panel of protease inhibitors were investigated (FIG. 16C). Prior to LCL204 treatment, DU145 cells were pretreated for one hour with vehicle only, zVAD-fmk (pan-caspase inhibitor), MG132 (proteasome inhibitor), CA074Me (cathepsin B inhibitor), or pepstatin A (cathepsin D inhibitor). Treatment with inhibitors alone had no effect on AC protein levels (not shown). Interestingly, more than one protease inhibitor blocked AC degradation. Pretreatment with pepstatin A had no effect on the LCL204-induced AC protein loss, while pretreatment with zVAD-fmk, MG132, or CA074Me all blocked AC degradation. Due to the specificity of CA074Me (Buttle, et al., Archives of Biochemistry & Biophysics, 299: 377-380, 1992), cathepsin B emerged as a primary candidate for mediating AC degradation. Caspase inhibitors such as zVAD-fmk are known to be rather promiscuous in their selectivity (Schotte, et al., FEBS Letters, 442: 117-121, 1999). Accordingly, both zVAD-fmk and MG132 have non-specific inhibitory activity against cathepsin B (data not shown). In conclusion, cathepsin B is the primary protease involved in AC degradation.

AC and ASMase both reside within the lysosomal membrane. In fact, both enzymes are known to closely interact as they co-precipitate when secreted into culture medium (He, et al., Journal of Biological Chemistry., 278: 32978-32986, 2003). LCL204 was found to induce a rapid decrease in ASMase activity beginning as early as 30 minutes after treatment (FIG. 16D, i). Furthermore, the loss of activity was blocked in the presence of CA074Me after a 2-hour treatment (FIG. 16D, ii), again implicating proteolytic degradation mediated by cathepsin B. Thus, in conclusion, LCL204 induces the degradation of both AC and ASMase, and that this process is mediated by cathepsin B.

LCL204 induces lysosomal destabilization and membrane permeabilization. LCL204 carries an N-myristyl-amino group and represents the secondary lipophilic amine, while the parent compound B13 is an N-myristoyl-amide and represents the neutral molecules. Lysosomal stability after LCL204 treatment was investigated using the acidophilic dye LysoTracker Red (LTR) and flow cytometric analysis. The results from these experiments were presented graphically to show the mean LTR fluorescence intensity, which is dependent on the acidic pH of lysosomes, therefore a decrease in fluorescence intensity indicates a rise in lysosomal pH (Boya, et al., Oncogene., 22: 3927-3936, 2003). While treating DU145 cells for 1 hour with 10 µM LCL204 induced the shift in LTR fluorescence, the same treatment with B13 or $C_6$-ceramide (30 µM) did not have this effect (FIG. 17A). Treatment with 10 mM NH4Cl served as a positive control. The effect on lysosomal pH was remarkably early in DU145 cells, beginning as early as five minutes after treatment with 10 µM LCL204 (FIG. 17B). LCL204 also destabilized lysosomes in a concentration-dependent manner (FIG. 17C). Collectively, these experiments indicate that the amino group carried by LCL204 confers lysosomotropic properties to the molecule, making it an amphiphilic drug.

Figure 17D:
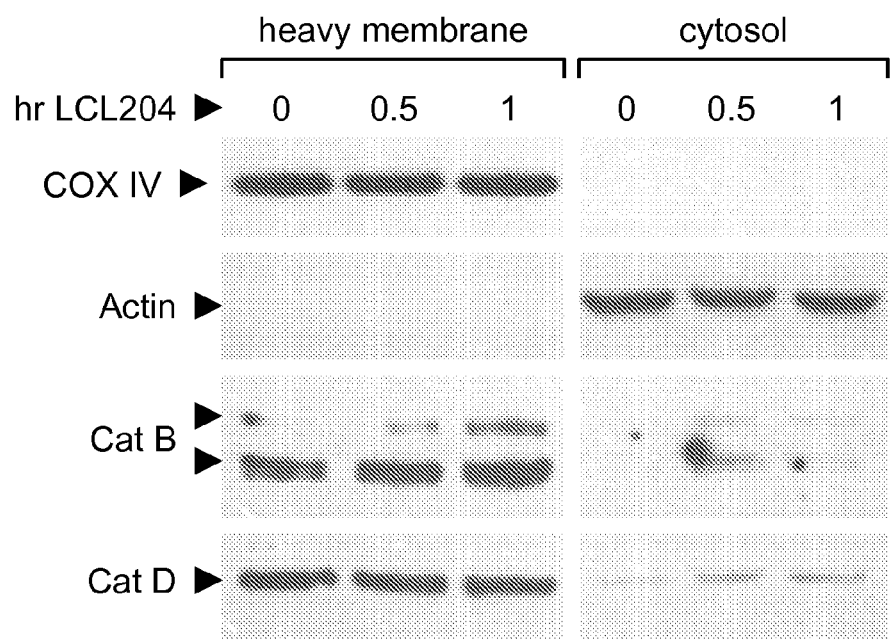
Figure 17E:
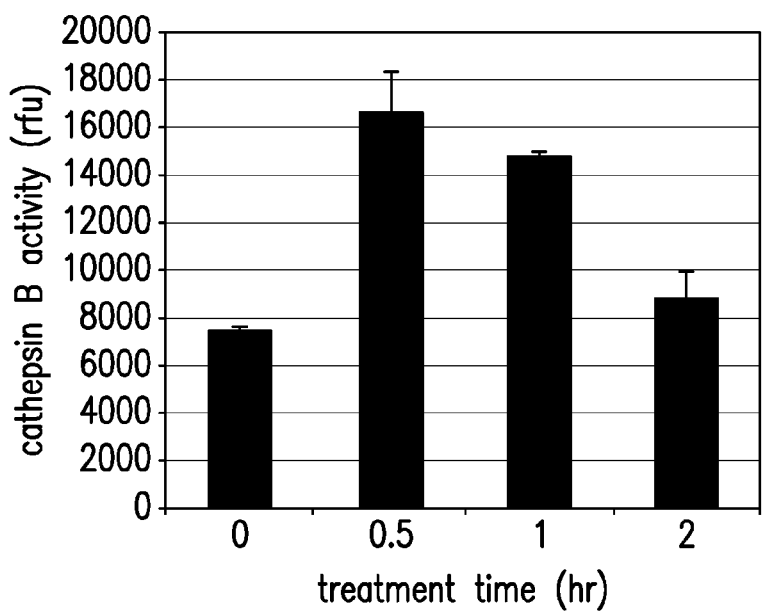

Lysosomal destabilization can result in membrane permeabilization and release of lysosomal proteins from the lysosomes into the cytosol. Both cathepsins B (Id.) and D (Roberg, et al., Free Radical Biology & Medicine., 27: 1228-1237, 1999) are released into the cytosol upon LMP. Using a subcellular fractionation technique, cytosolic proteins were separated from heavy membrane bound proteins in DU145 cells and analyzed protein location by Western blot (FIG. 17D). There was no contamination of mitochondrial (COX IV) or lysosomal (cathepsin B) proteins from the membrane fraction in the cytosolic fraction. However, after treating DU145 cells with LCL204, the active form of cathepsins B was detected in the cytosolic fraction within 30 minutes of treatment (FIG. 17D). To confirm these findings, enzymatic activity of cathepsin B was measured in the cytosol before and after LCL204 treatment (FIG. 17E). As expected, low activity was detected in the cytosol of untreated cells. However, cathepsin B activity increased within 30 minutes of 10 µM LCL204 treatment before returning to basal levels. In summary, LCL204 not only rapidly elevates lysosomal pH but also affects the membrane integrity of the lysosomes as indicated by translocation of cathepsin B to the cytosol.

Figures 18A, 18B:
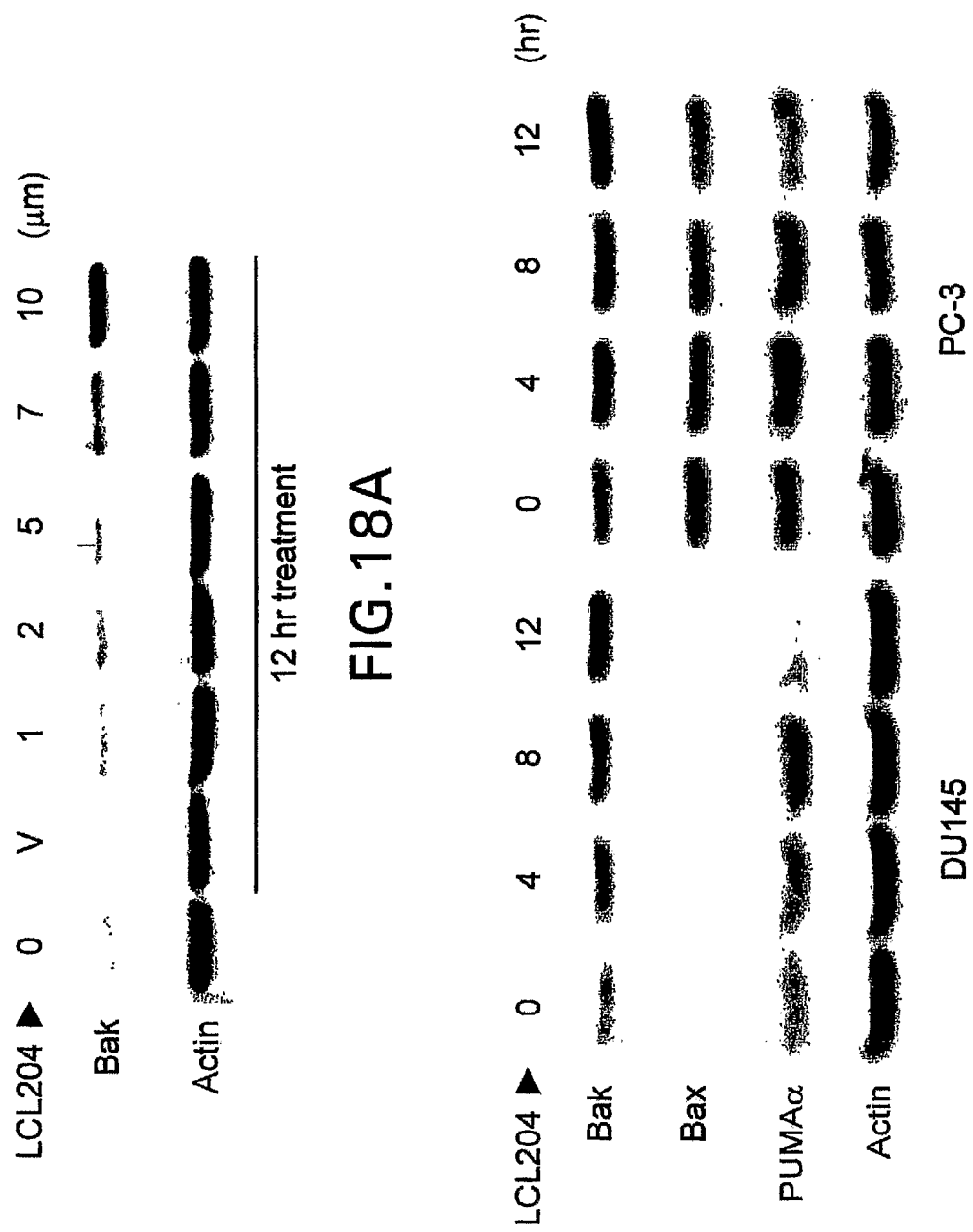

LCL204 induces Bak activation and up-regulates p53 family members. The potential roles for pro-apoptotic Bcl-2 family members in LCL204-induced apoptosis were investigated. Compared to vehicle (V) control, a concentration-dependent up-regulation of Bak protein levels in DU145 cells was detected following a 12-hour treatment with increasing concentrations of LCL204 (FIG. 18A). This process was also time-dependent, as both DU145 and PC-3 cells accumulated Bak protein over a 12-hour LCL204 (10 µM) treatment (FIG. 18B). Interestingly, despite being highly homologous to Bak, Bax protein levels were unaffected in PC-3 cells following the same LCL204 treatment (FIG. 18B). Correlative to Bak up-regulation was the BH3-only protein, PUMA. PUMA was up-regulated in DU145 cells after eight hours treatment and earlier (four hours) in PC-3 cells (FIG. 18B). Activation of Bak was confirmed using confocal microscopy to visualize formation of Bak mitochondria-associated clusters. Formation of Bak foci along the mitochondria is a hallmark of apoptosis (Nechushtan, et al., J Cell Biol, 153: 1265-1276., 2001). Control cells showed even Bak distribution (red) along the mitochondria membrane (green), appearing as yellow in the overlay (FIG. 18C). However, after 20 hours LCL204 treatment formation of Bak foci was detected on the mitochondria membrane, demonstrated by the red Bak clusters interspersed amongst the green-labeled mitochondria membrane marker, YFP-mito (FIG. 18C).

Bak, Bax, and PUMA are all described as p53-inducible genes (Miyashita, et al., Cell., 80: 293-299, 1995; Gu, et al., Oncogene., 23: 1300-1307, 2004; Nakano, et al., Mol Cell, 7: 683-694., 2001). DU145 cells harbor two mutations in the p53 gene, which still allow for 16% partial function and 13% wild-type function of the gene product (Shi, et al., Prostate., 51: 59-72, 2002). LCL204 induced p53 in DU145 cells after four hours treatment (FIG. 18D). PC-3 cells, however, are p53$^{null}$ due to a frame shift mutation that results in a stop codon. While there is no detectable p53 in these cells, p73β induction was detected after only two hours of LCL204 treatment (FIG. 18D). The same isoform of p73 was not detected in DU145 cells. Both cell lines showed similar patterns of Bak up-regulation, while PC-3 cells had an earlier and more pronounced PUMA up-regulation than DU145. Thus, the affects of LCL204 on Bak protein levels occur independent of p53 or p73 expression, while that of PUMA may require p53 or p73 involvement.

LCL204-induced molecular events involve JNK and p38 MAPK targets. The roles of JNK and p38 MAPK were investigated following LCL204 treatment.

Figure 19A:
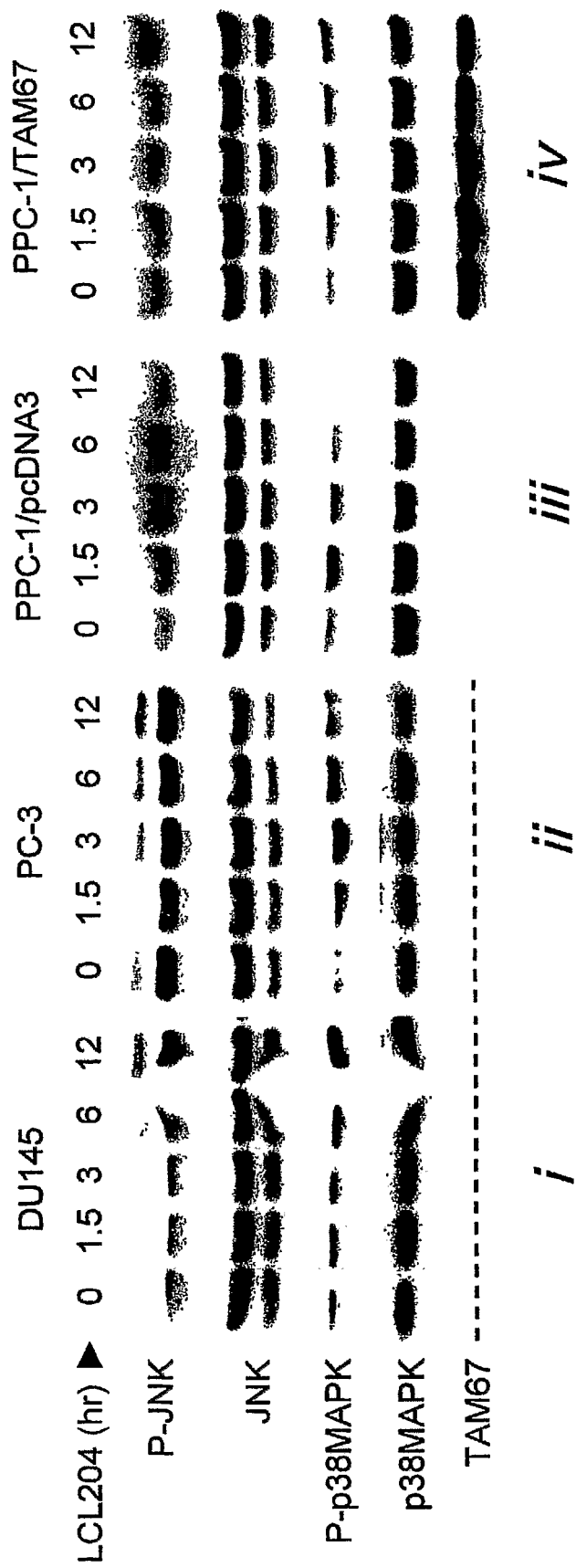

LCL204 was found to induce phosphorylation and activation of JNK in both DU145 and PC-3 cells in a time-dependent manner, beginning as early as three hours after treatment and continuing up to 12 hours later (FIG. 19A). Similar results were found when examining p38 MAPK phosphorylation. However, p38 MAPK phosphorylation was much earlier in PC-3 cells than in DU145 (FIG. 19A). In order to better characterize JNK and p38 MAPK involvement, PPC-1 cells were used to stably transfected with a dominant-negative mutant of c-Jun (TAM67), which inhibits AP-1 function (Brown, et al., Oncogene, 9: 791-799., 1994). PPC-1/pcDNA3 cells had a rapid and long-lived JNK activation, while PPC-1/TAM67 cells showed a slower activation of JNK (FIG. 19A). Similar results were found with p38 MAPK, where LCL204 induced rapid phosphorylation by 90 minutes in vector control cells but was less apparent in TAM67-expressing cells. These results indicate that neutralizing AP-1 function have a limiting effect on upstream stress kinases.

Figure 19B:
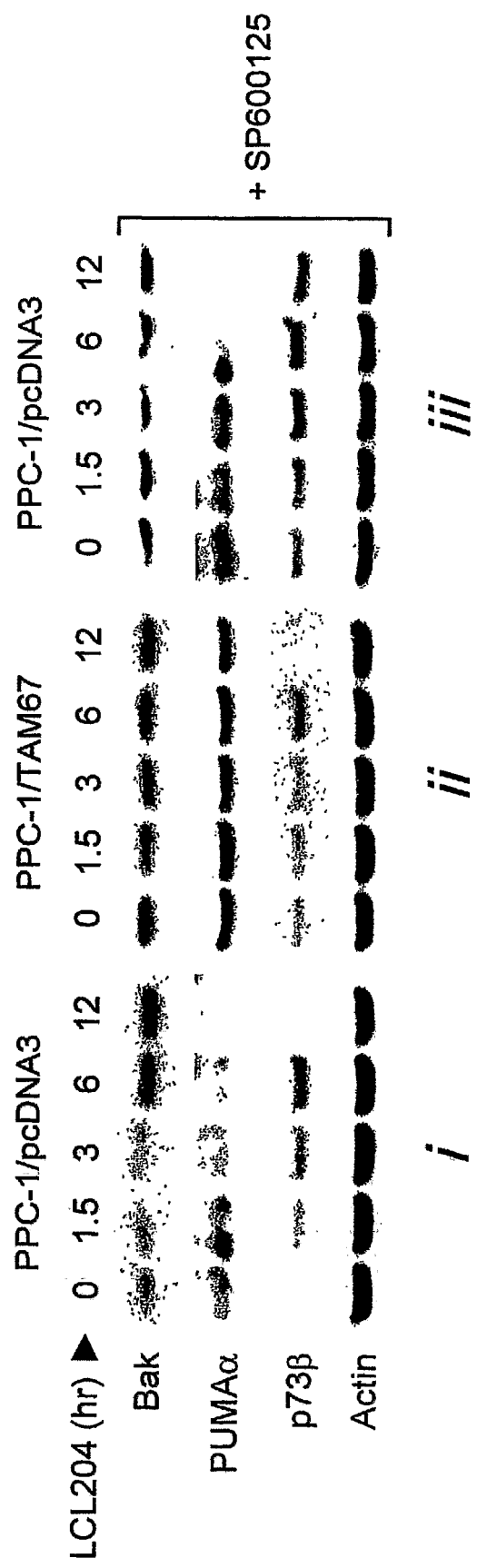

TAM67 expression also delayed Bak induction remarkably when compared to vector control cells (FIG. 19B, i, ii). Treating vector control cells with LCL204 in the presence of the JNK inhibitor, SP600125, mimicked these results (FIG. 19B, iii). Both transfectants showed differences in PUMA expression levels following LCL204 treatment. Control cells showed a rapid and transient induction of PUMA after 90 minutes treatment, while in TAM67-expressing cells, PUMA levels only marginally increased at the same time point (FIG. 19B, i, ii). SP600125 also delayed this induction until approximately 6 hours of treatment (FIG. 19B, iii). PPC-1 cells are reportedly derived from PC-3 cells (Sobel, et al., J Urol, 173: 342-359., 2005). As such, there is no detectable p53 protein in these cells (data not shown). Similar to PC-3 cells, a time-dependent p73β induction was detected in PPC-1/pcDNA3 cells following LCL204 treatment (FIG. 19B, i). PPC-1/TAM67 cells also showed an increase in p73, although to a lesser extent (FIG. 19B, ii). While the JNK inhibitor affected LCL204-induced Bak and PUMA changes, it did not affect p73 induction (FIG. 19B. iii). Therefore, JNK/AP-1 function is important for up-regulation of Bak and PUMA in response to LCL204 treatment, but not for that of p73.

Figure 19C:
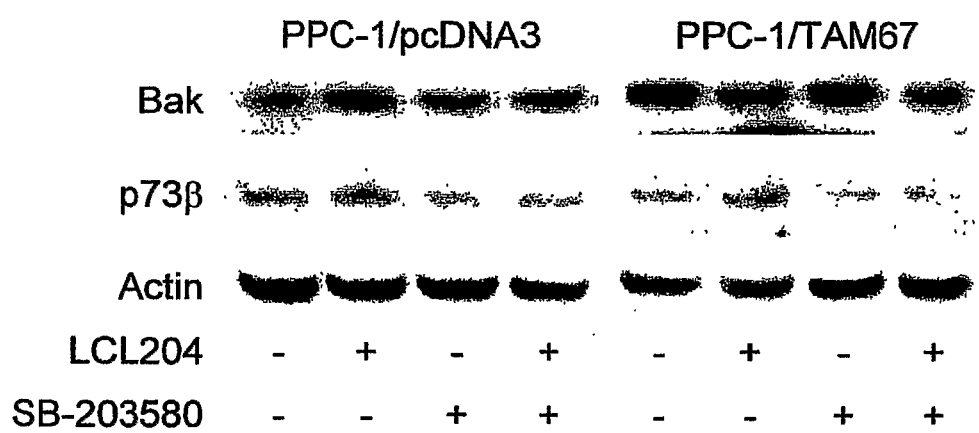

The relationship between this SAPK and p73 induction was investigated. Treating PPC-1/pcDNA3 cells with LCL204 (7.5 µM) for 5 hours caused an up-regulation of both Bak and p73 levels (FIG. 19C). In the same experiment, PPC-1/TAM67 cells showed faulty up-regulation of Bak but similar up-regulation of p73. Interestingly, in both cell lines, treatment with the p38 MAPK inhibitor SB-203580 alone for the same duration lowered basal p73 levels (FIG. 19C). This inhibitor also blocked the LCL204-induced p73 up-regulation. At the same time, inhibiting p38 MAPK did not appear to block LCL204-mediated effects on Bak protein levels. These results implicate p38 MAPK as a necessary component to mediate LCL204-induced p73 accumulation but not for the same of Bak.

Figure 19D:
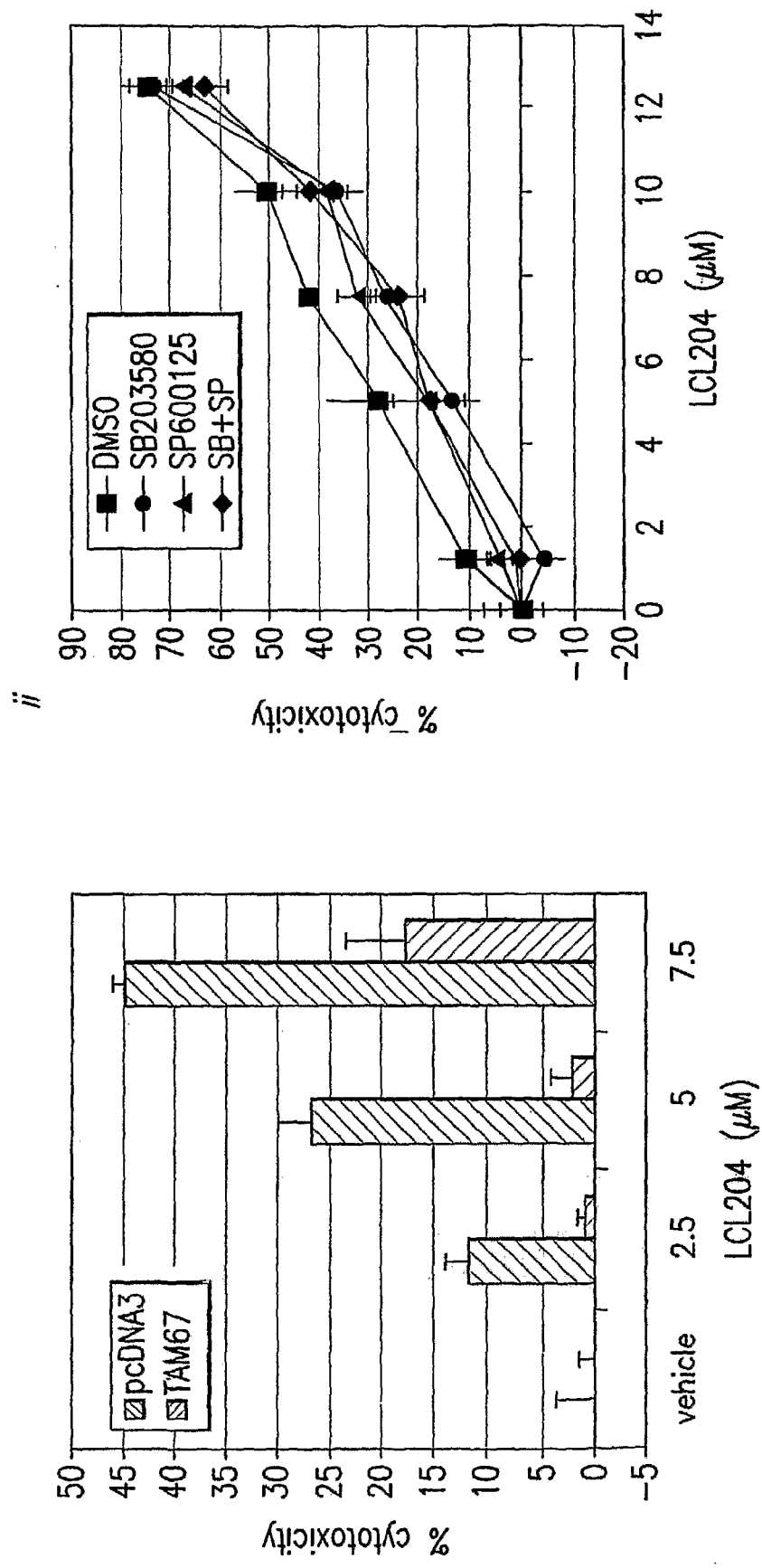

Finally, TAM67 transfectants were more resistant to LCL204 in response to 12 hours LCL204 treatment when compared to vector control cells (FIG. 19D, i). Furthermore, in PPC-1/pcDNA3 cells, both SB-203580 and SP600125 inhibited cell killing to a similar extent (FIG. 19D,ii). However, inhibiting JNK and p38 MAPK simultaneously did not offer more protection from LCL204 cell death than either inhibitor alone. Therefore, both JNK and p38 MAPK are active components of the LCL204-induced apoptotic pathway.

7.3 Discussion

The lysosome and its constituents serve as effective targets for new cancer therapeutics. When treating DU145 cells with LCL204, transient ceramide elevation was detected. The initial rise in ceramide is due to the pharmacological inhibition of AC by LCL204. During lysosomal destabilization both AC and ASMase are degraded, which leads to the corresponding fall of ceramide levels back to baseline. It should be noted that despite the transient nature of ceramide elevation, LCL204 is a much more potent inducer of cell death than B13 in vitro. This is due to the loss of lysosomal stability and function induced by LCL204. Thus, LCL204 affects multiple pathways including lysosomal function and ceramide regulation. Furthermore, the apoptotic consequences of LCL204-induced lysosomal rupture could not be reproduced with other agents that strictly alter lysosomal pH such as bafilomycin A1 or $NH_4Cl$. This indicates that the hydrophobic lipid structure of LCL204 may be necessary for exerting these effects.

The fact that over 40% of PCa tumors over-express the acid ceramidase gene is significant in regards to ceramide levels in tumors (Seelan, et al., Genes, Chromosomes & Cancer., 29: 137-146, 2000). This finding creates an additional benefit of LCL204 as a cancer therapeutic due to the proteolytic degradation of AC induced by this molecule. AC/ASMase degradation is not likely caused by a generalized conversion of cathepsin B from its pro- to active form, as there is a high level of basal active cathepsin B in DU145 cells. The tricyclic antidepressant desipramine is known to induce degradation of ASMase, which can be blocked using the protease inhibitor leupeptin (Hurwitz, et al., Biological Chemistry Hoppe Seyler, 375: 447-450, 1994). LCL204 induces a conformational change in ASMase, which is anchored within the lysosomal membrane. This was thought to result in exposure of proteolytic cleavage site(s) to the lysosomal lumen, allowing for its degradation by lysosomal proteases.

The early and transient PUMA up-regulation induced by LCL204 was also affected by inhibiting JNK/AP-1. The extent of PUMA increase in PPC-1/TAM67 cells was much less compared to controls. Also, SP600125 delayed LCL204-induced PUMA induction in PPC-1/pcDNA3 cells. Therefore, JNK/AP-1 function appears critical for induction of Bak and may also play a lesser role in PUMA regulation following LCL204 treatment.

FIG. 20 represents a summary of the molecular events induced by LCL204. LCL204 causes lysosomal function to rapidly deteriorate due to elevation of pH and is accompanied by changes in ceramide levels and degradation of AC and ASMase. This is accompanied by translocation of cathepsins to the cytosol and activation of SAPKs. p38 MAPK activation is necessary for p73 induction, while JNK/AP-1 activation results in the induction of Bak, and enhancement of PUMA and of p73. These proteins act in concert to induce mitochondria depolarization and apoptosis. Due to the multiple pathways induced by LCL204, targeting one pathway component at a time is insufficient to inhibit cell death, making it a potent cytotoxic agent for destroying cancer cells.

8. Example

Combined Apoptotic Signaling Ligand/Ceramide Analog Therapy

The present invention provides the first description for the synergistic effect of combining gene therapy and ceramide modulators in treatment of prostate cancer.

Pilot studies in the inventors' laboratory have demonstrated that direct intra-tumor injection of up to $5 \times 10^9$ MOI of AdGFPFasL was safe in a 25 gm nude mouse, which is equivalent to $1.36 \times 10^{13}$ particles in a 150-pound human. Safety is a potential issue when using FasL in gene therapy due to FasL's toxic effect on the liver. To ameliorate this safety concern, an adenoviral vectors with prostate-restricted expression that can be administered systemically to mice without side effects has been developed as described in Rubinchik et al., (2001) *Molecular Therapy* 4, 416-26, Lowe et al., (2001) *Gene Therapy* 8, 1363-71.

These new improved vectors can be injected intravenously in mice without ill effects, which is direct evidence that using FasL as a therapeutic molecule in vivo is a reasonable possibility if mouse safety data translates to humans. Further, these vectors are designed to be regulated by doxycycline providing for a second level of control. If a patient should experience an adverse reaction, to FasL expression, addition or withdrawal of doxycycline (depending upon the virus) will stop production of FasL, which is surmised to allow the patient to recover.

The viruses described in Rubinchik et al. had been used under in vivo conditions to treat prostate cancer xenografts.

Following administration of 1.5×10⁹ pfu of AdGFPFasL to PPC1 (prostate cancer) xenografts, 60% of tumors regress or failed to grow. Since viral delivery is at most 30% efficient, complete regression of an injected tumor suggests that a bystander effect is operative. One of the limitations in PCa gene therapy is delivery of the therapeutic gene to every cell in the tumor. One way to overcome this is to amplify the response to the delivered gene by taking advantage of the bystander effect. For example, virally-expressed wild-type p53 is capable of inducing apoptosis in many types of cancer cells and is reported to have bystander activity by inducing localized FasL expression which recruits neutrophils infiltration that is believed to play a critical role in the bystander mechanism. In practice, the bystander effect, if activated, will result in regression of a solid tumor in spite of the physician's inability to deliver, by virus or liposome, a therapeutic gene to every cell. In vitro or in vivo bystander activity has been demonstrated for FasL, TRAIL and p53. In the DU145 model of prostate cancer, the inventors determined that resistance to the induction of apoptosis through the Fas receptor signaling pathway is due to overexpression of apoptotic resistance genes including cFLIPs (Hyer et al., Cancer Biology and Therapy 1(4): 405-410, 2002). The inventors' further demonstrated that expression of a FasL-GFP fusion gene overcomes resistance in infected cells, kills the cell apoptotically, and produces apoptotic vesicles that also can signal Fas to induce apoptosis in adjacent cells (i.e. bystander activity). However, expression of apoptotic resistance genes in some cancers, including in the DU145 model, make the cells relatively insensitive to vesicle-mediated bystander activity. To overcome this, a number of different chemotherapeutic drugs and other small molecules were examined for their effect on apoptotic resistance mechanisms. Doxorubicin (0.2 µg/ml) decreases expression of cFLIP protein without a concomitant decrease in levels of FLIP mRNA. This decrease in protein levels may be due to proteasomal degradation or a translational block. Under these conditions, a 20% increase in sensitivity of apoptotic vesicles is observed with 0.2 µg/ml doxorubicin. However, 0.2 µg/ml doxorubicin is itself toxic to DU145 cells at 48-72 hours, which in this case, obscures the role of the bystander vesicles in promoting apoptosis.

LCL102, a ceramidase inhibitor, which acts to increasing intracellular ceramide levels by elevating ceramide, were tested in this system. This molecule was highly efficient at activating cell death in DU145 cells at nontoxic doses if combined with AdGFPFasL virus at MOIs achievable in vivo. DU145 cells growing in 96 well plates at 1×10⁴ cells/well are treated with either media alone or LCL102 at 2 uM for 48 hours followed by AdGFPFasL for 24 hours at the MOI (5-80). Cell death is assayed by the MTS assay. At 2 uM LCL102 and 5MOI of virus, cell death is amplified 4-fold compared to LCL102 alone (FIG. 14).

Figure 12B:
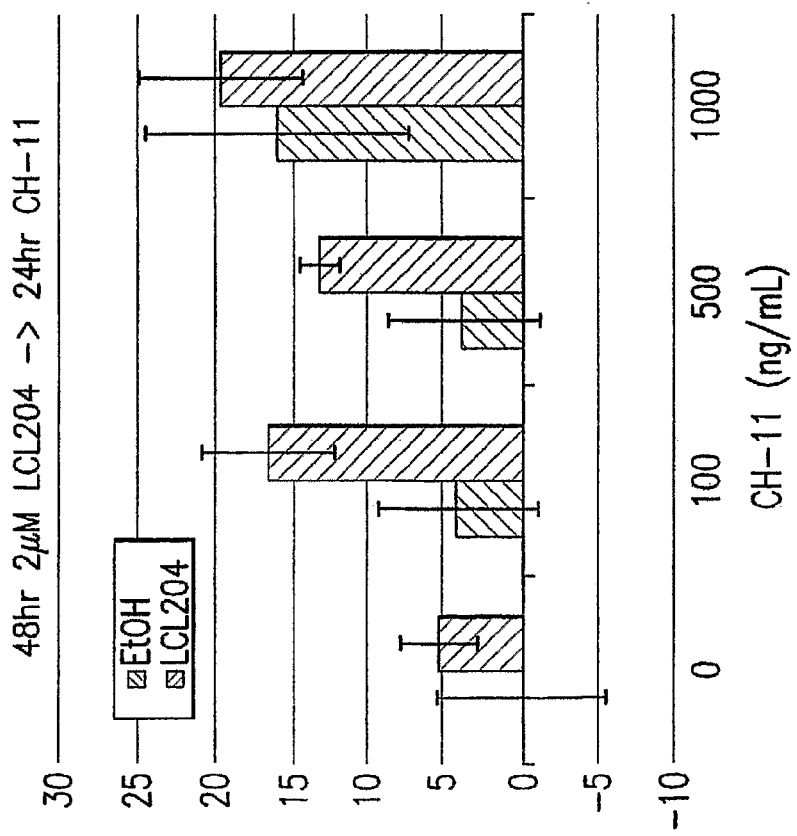
Figure 12A:
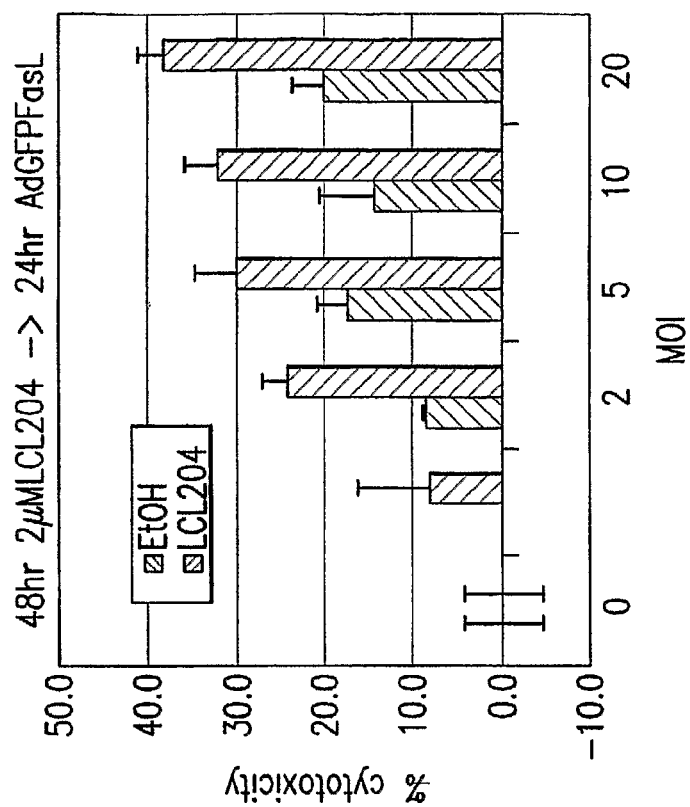

Treating these cells with sub-toxic doses of another compound, LCL204 (2 µM) in combination with the AdGFPFasL virus at low MOIs (which are achievable in vivo) resulted in up to a 10-fold increase in cancer cell death (FIG. 12A). This was likely due to the down-regulation of anti-apoptotic proteins cFLIP$_S$, Survivin, cIAP-1, and RIP via activation of the proteasome (FIG. 12B). Caspase 8 was unaffected. Activation of apoptosis appeared to be through multiple mechanisms including cathepsin D, the mitochondria and activation of NFκβ. This suggests that LCL204-induced ceramide elevation acts downstream of caspase 8 to push the cells into a pro-apoptotic state, leaving them more susceptible to AdGFPFasL-induced apoptosis. LCL204 was not modifying viral infectivity.

Figure 13B:
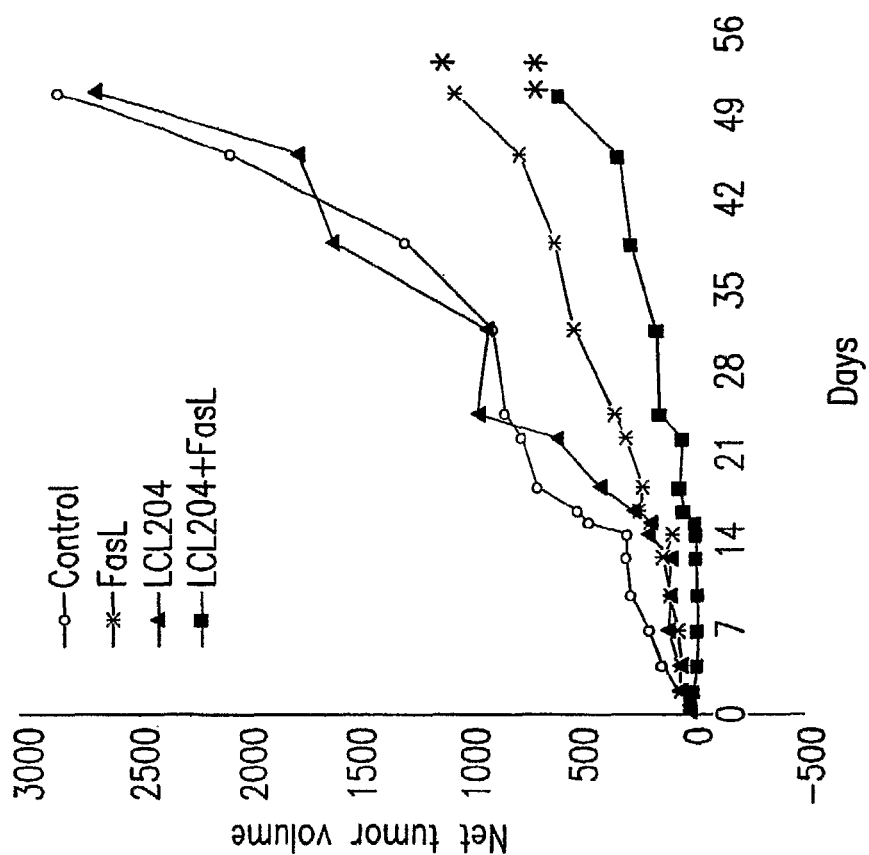
Figure 13A:
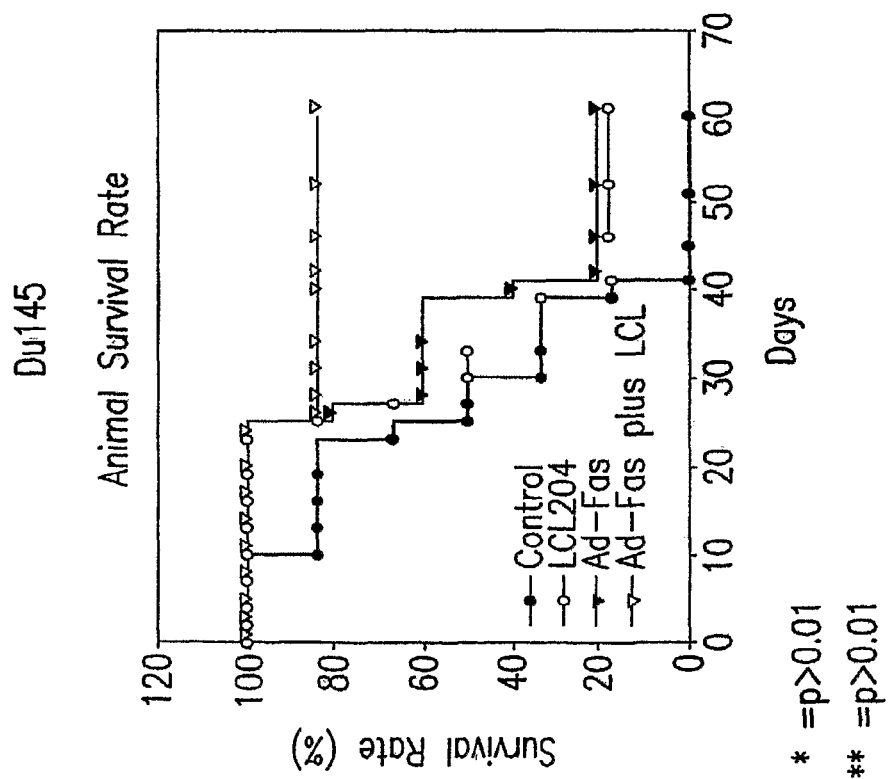
Figure 15B:
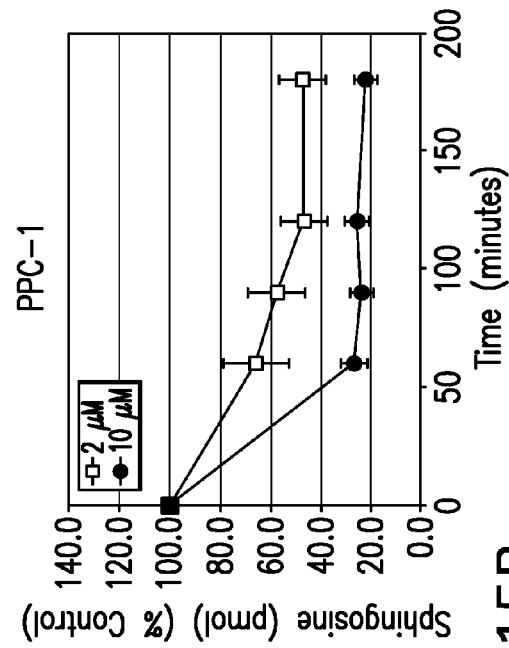
Figure 15D:
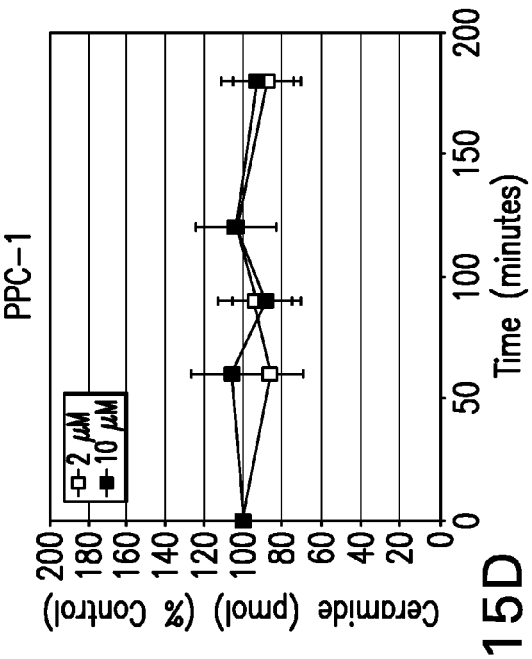
Figure 15A:
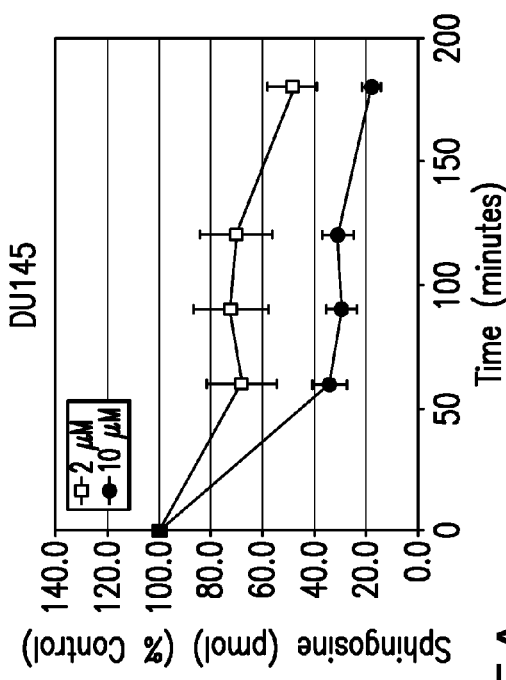
Figure 15C:
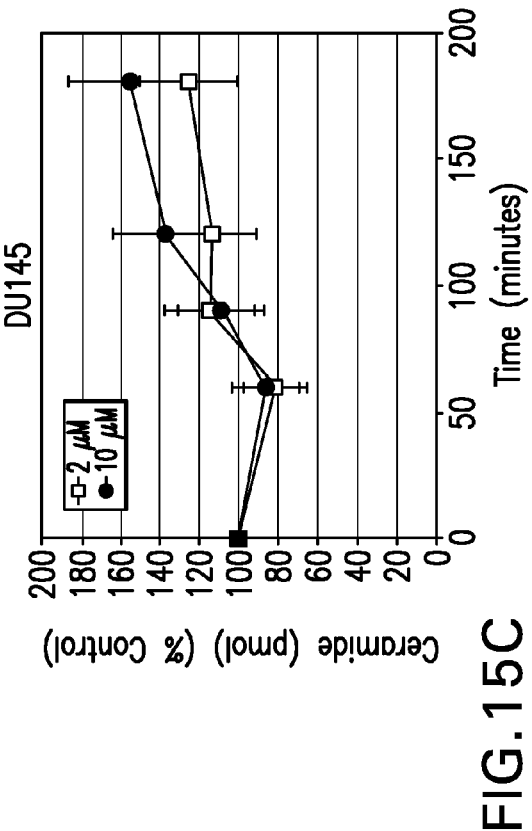

One of the problems with cancer gene therapy as it is currently practiced is the issue of delivery of gene therapy vectors to every tumor cell in order to effect death of the tumor. As described above, this limitation was overcome by showing that it is possible to induce a bystander effect in prostate cancer cells using the AdGFPFasL virus. However, certain types of cells lines including DU145 are relative to highly resistant to the exogenous application of either FasL, the monoclonal antibodies that are FasL agonists, or the bystander vesicles. The inventors devised a model of molecular cell killing in a solid tumor in which only perhaps up to 30% of the cells are infected by the virus. Since the ceramide analogs of the invention are acid CDase inhibitors which sensitize the cells to this type of cell death, an in vivo experiment in which prostate cancer xenografts, in this case DU145 cells, were grown in nude mice and treated sequentially with the acid Cdase inhibitor LCL204 followed by the AdGFP-FasL virus. FIG. 13A clearly demonstrates the efficacy of this approach. For example, FIG. 13B demonstrates that virus by itself has little effect on overall growth rate of these tumors. FIGS. 13 A and B demonstrate that LCL204 has some modest effects when administered systemically to the animal but yet the tumors continue to grow. FIGS. 13A and B show that the combination of the two molecules and clearly demonstrates efficacy in this combination therapy and FIG. 13B is a vehicle control. The LCL204 was administered at 0, 72 and 144 hours and the virus (1×10⁹ pfu) at 10 and 82 hours. The importance of this is two-fold. First, orthotopic administration of the AdGFPFasL virus does not result in any systemic toxicity as judged by these experiments. Secondly, the administration of up to 75 mg/kg of LCL204 has no observable effect on the animal. When combined, these two molecules effectively reduce the tumor burden and yet at the same time leave the animal in overall good health.

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed:
1. A compound of formula:

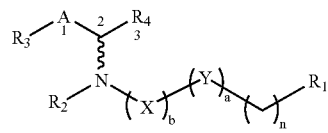

and pharmaceutically acceptable salts thereof, wherein:
$R_1$ is —SH, —NH$_2$, —Cl, —Br, —I, —C(O)OH, —C(O)NH$_2$, —NH(C=NH)NH$_2$, —NH(R$_2$), or —N-heterocycle having from 5 to 6 atoms in the ring;
$R_2$ is —H or —(C$_1$-C$_6$)alkyl;
$R_3$ is -phenyl optionally substituted with one or more —R$_5$;
$R_4$ is —(C$_1$-C$_6$)alkyl, —SH, —NH$_2$, —CH$_2$Cl, —CH$_2$Br, —CH$_2$I, —C(O)OH, or —C(O)NH$_2$;
$R_5$ is —(C$_1$-C$_6$)alkyl, —F, —Cl, —Br, —I, —NH(R$_{2a}$), —NO$_2$, or an amide of formula

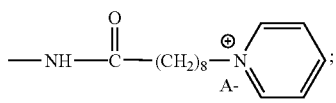

$R_{2a}$ is —H or —($C_1$-$C_6$)alkyl;
X is —$CH_2$—, —CH(($C_1$-$C_6$)alkyl)—, or —C(S)-;
Y is —$CH_2$—, —C(O)—, —N(H)—, or —O—;
A is —CH(OH)—;
a is 0 or 1;
b is 1;
n is an integer from 8 to 22; and
$A^-$ is a pharmaceutically acceptable counter-anion.

2. A compound of formula:

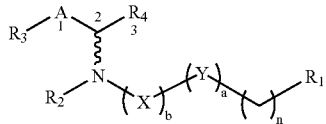

and pharmaceutically acceptable salts thereof, wherein:
$R_1$ is H, —OH, —SH, —$NH_2$, —Cl, —Br, —I, —C(O)OH, —C(O)$NH_2$, —NH(C=NH)$NH_2$, —NH($R_2$), or —N-heterocycle having from 5 to 6 atoms in the ring;
$R_2$ is —H or —($C_1$-$C_6$)alkyl;
$R_3$ is -phenyl substituted with one or more $R_5$;
$R_4$ is —H, —($C_1$-$C_6$)alkyl, —$CH_2$(OH), —SH, —$NH_2$, —$CH_2$Cl, —$CH_2$Br, —$CH_2$I, —C(O)OH, or —C(O)$NH_2$;
$R_5$ is

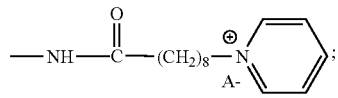

X is —$CH_2$—, —CH(($C_1$-$C_6$)alkyl)—, —C(O)—, or —C(S)-;
Y is —$CH_2$—, —C(O)—, —N(H)—, or —O—;
A is —$CH_2$—or —CH(OH)—;
a is 0 or 1;
b is 0 or 1;
n is an integer from 2 to 22; and
$A^-$ is a pharmaceutically acceptable counter-anion.

3. The compound of claim 2, wherein X is —C—(O)— or —C—(S)-.

4. The compound of claim 2 or 3, wherein $R_1$ is:

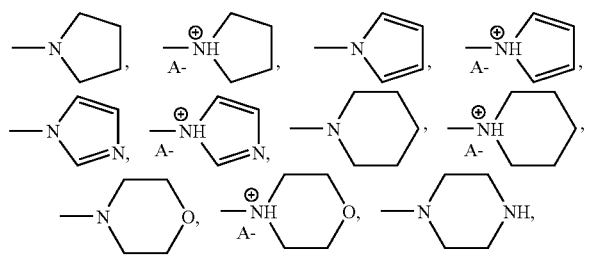

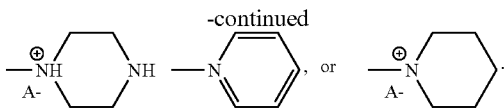

5. The compound of claim 4, wherein A– is selected from the group consisting of $F^-$, $Cl^-$, $Br^-$, $I^-$, acetate, propanoate, $PO_4^{3-}$, $PO_4H^{2-}$, $PO_4H^{2-}$, $OH^-$, oxalate, and tartrate.

6. The compound of claim 3, wherein Y is —N(H)—.

7. A compound of the formula:

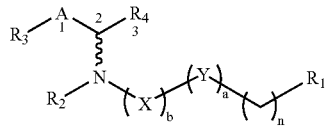

and pharmaceutically acceptable salts thereof, wherein:
$R_1$ is —OH, —SH, —$NH_2$, —Cl, —Br, —I, —C(O)OH, —C(O)$NH_2$, —NH(C=NH)$NH_2$, —NH($R_2$), or —N-heterocycle having from 5 to 6 atoms in the ring;
$R_2$ is —H or —($C_1$-$C_6$)alkyl;
$R_3$ is phenyl optionally substituted with one or more —$R_5$;
$R_4$ is —H, —($C_1$-$C_6$)alkyl, —$CH_2$(OH), —SH, —$NH_2$, —$CH_2$Cl, —$CH_2$Br, —$CH_2$I, —C(O)OH, —C(O)$NH_2$;
$R_5$ is —($C_1$-$C_6$)alkyl, —F, —Cl, —Br, —I, —NH($R_{2a}$), —$NO_2$, or an amide of formula

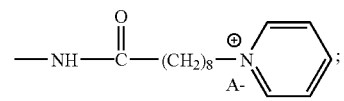

$R_{2a}$ is —H or —($C_1$-$C_6$)alkyl;
X is —C(O)—or —C(S)-;
Y is —$CH_2$—, —N(H)—, or —O—;
A is —$CH_2$—or —CH(OH)—;
a is 1;
b is 1;
n is an integer from 2 to 22; and
A—is a pharmaceutically acceptable counter-anion.

8. The compound of claim 7, wherein $R_1$ is:

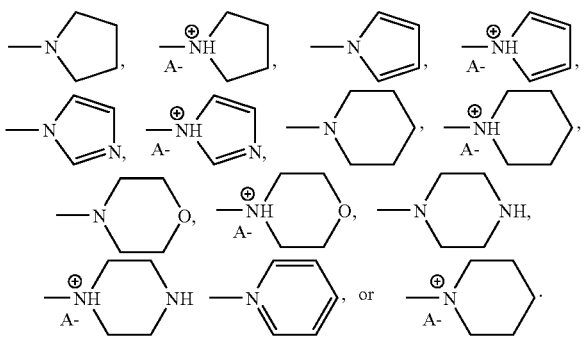

9. The compound of claim 7, wherein the compound is selected from:

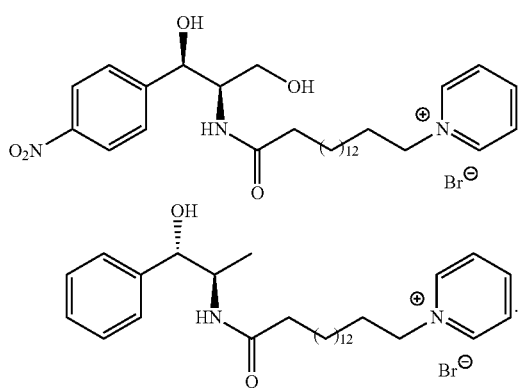 and

10. A compound of the formula:

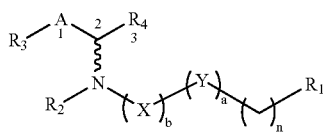

and pharmaceutically acceptable salts thereof, wherein:
$R_1$ is —SH, —$NH_2$, —Cl, —Br, —I, —C(O)OH, —C(O)$NH_2$, —NH(C=NH)$NH_2$, —NH($R_2$), or —N-heterocycle having from 5 to 6 atoms in the ring;
$R_2$ is —H or —($C_1$-$C_6$)alkyl;
$R_3$ is -phenyl optionally substituted with one or more —$R_5$;
$R_4$ is —($C_1$-$C_6$)alkyl, —$CH_2$(OH), —SH, —$NH_2$, —$CH_2$Cl, —$CH_2$Br, —$CH_2$I, —C(O)OH, or —C(O)$NH_2$;
$R_5$ is —($C_1$-$C_6$)alkyl, —F, —Cl, —Br, —I, or an amide of formula

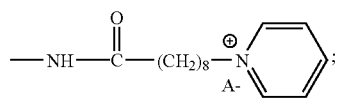

X is —$CH_2$—, —CH(($C_1$-$C_6$)alkyl)—, or —C(S)-;
Y is —$CH_2$—, —C(O)—, —N(H)—, or —O—;
A is —$CH_2$- or —CH(OH)—;
a is 0 or 1;
b is 1;
n is an integer from 8 to 22; and
$A^-$ is a pharmaceutically acceptable counter-anion.

11. The compound of claim 1, wherein $R_1$ is:

[structures]

12. The compound of claim 11, wherein A– is selected from the group consisting of $F^-$, $Cl^-$, $Br^-$, $I^-$, acetate, propanoate, $PO_4^{3-}$, $PO_4H_2^-$, $PO_4H^{2-}$, $OH^-$, oxalate, and tartrate.

13. The compound of claim 1 or 10, wherein $R_3$ is phenyl substituted with one or more —$R_5$, wherein $R_5$ is —($C_1$-$C_6$) alkyl, —F, —Cl, —Br, —I, or an amide of formula

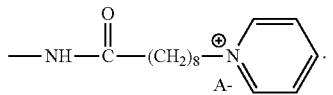

* * * * *